United States Patent

Beall et al.

[11] Patent Number: 5,730,996
[45] Date of Patent: Mar. 24, 1998

[54] INTERCALATES AND EXPOLIATES FORMED WITH ORGANIC PESTICIDE COMPOUNDS AND COMPOSITIONS CONTAINING THE SAME

[75] Inventors: Gary W. Beall, McHenry; Semeon Tsipursky, Lincolnwood, both of Ill.; Katherine R. Turk, Twin Lakes, Wis.

[73] Assignee: Amcol International Corporation, Arlington Heights, Ill.

[21] Appl. No.: 652,756

[22] Filed: May 23, 1996

[51] Int. Cl.$^6$ .................................................. A01N 25/10
[52] U.S. Cl. .................. 424/405; 424/406; 424/409; 424/410; 424/411; 424/417; 424/421; 424/484; 424/489
[58] Field of Search .................................. 424/405, 406, 424/409–411, 417, 421, 484, 489

[56] References Cited

U.S. PATENT DOCUMENTS

| | | | |
|---|---|---|---|
| 2,875,119 | 2/1959 | Trademan et al. | 424/421 |
| 2,923,659 | 2/1960 | Ziegler et al. | 424/421 |
| 3,308,018 | 3/1967 | Gier et al. | 424/410 |
| 3,419,460 | 12/1968 | Ure | 161/162 |
| 3,419,517 | 12/1968 | Hedrick et al. | 260/37 |
| 3,515,626 | 6/1970 | Duffield | 161/162 |
| 3,773,708 | 11/1973 | Takahashi et al. | 260/41 R |
| 3,795,650 | 3/1974 | Burns | 260/33.4 R |
| 3,912,532 | 10/1975 | Simone | 106/308 N |
| 3,920,442 | 11/1975 | Albert et al. | 71/92 |
| 3,929,678 | 12/1975 | Laughlin et al. | 252/526 |
| 4,125,411 | 11/1978 | Lyons | 106/291 |
| 4,210,572 | 7/1980 | Herman et al. | 260/404 |
| 4,251,576 | 2/1981 | Osborn et al. | 428/331 |
| 4,400,485 | 8/1983 | Mukamal et al. | 524/444 |
| 4,431,755 | 2/1984 | Weber et al. | 523/203 |
| 4,434,075 | 2/1984 | Mardis et al. | 252/315.2 |
| 4,472,538 | 9/1984 | Kamigaito et al. | 523/202 |
| 4,500,670 | 2/1985 | McKinley et al. | 524/445 |
| 4,546,145 | 10/1985 | Kishida et al. | 524/780 |
| 4,600,744 | 7/1986 | Libor et al. | 524/446 |
| 4,613,542 | 9/1986 | Alexander | 428/290 |
| 4,624,982 | 11/1986 | Alexander | 524/446 |
| 4,739,007 | 4/1988 | Okada et al. | 524/789 |

(List continued on next page.)

FOREIGN PATENT DOCUMENTS

| | | |
|---|---|---|
| 0 205 281 A3 | 12/1986 | European Pat. Off. |
| 0 335 653 A1 | 10/1989 | European Pat. Off. |

(List continued on next page.)

OTHER PUBLICATIONS

C. W. Francis, "Adsorption of Polyvinylpyrrolidone on Reference Clay Minerals", Soil Science, vol. 115, No. 1, 1973, pp. 40–54.

A. Usuki, et al., "Synthesis of nylon 6–clay hybrid", J. Mater. Res., vol. 8, No. 5, May 1993, pp. 1179–1184.

Y. Kojima, et al., "Mechanical Properties Of Nylon 6–Clay Hybrid", J. Meter. Res., vol. 8, No. 5, May 1993, pp. 1185–1189.

(List continued on next page.)

*Primary Examiner*—Neil S. Levy
*Attorney, Agent, or Firm*—Marshall, O'Toole, Gerstein, Murray & Borun

[57] ABSTRACT

Intercalates formed by contacting an activated layered material, e.g., an activated phyllosilicate, with an intercalant pesticide to intercalate an intercalant pesticide between adjacent platelets of the layered material is disclosed. Sufficient intercalant pesticide is sorbed between adjacent platelets to expand the adjacent platelets to a spacing of at least about 5 Å (as measured after water removal to a maximum of 5% by weight water) up to about 100 Å, and preferably in the range of about 10 to about 45 Å, so that, if desired, the intercalate can be exfoliated into individual platelets. The intercalate can be combined with an organic liquid to form a viscous composition for delivery of a pesticide compound. Alternatively, the intercalate can be exfoliated prior to combination with the organic liquid. The intercalated complex also can be admixed with solid particles to provide a granular, dust, or wettable powder pesticide composition.

48 Claims, 29 Drawing Sheets

U.S. PATENT DOCUMENTS

| | | | |
|---|---|---|---|
| 4,789,403 | 12/1988 | Rice | 106/417 |
| 4,798,766 | 1/1989 | Rice | 428/404 |
| 4,810,734 | 3/1989 | Kawasumi et al. | 523/216 |
| 4,842,651 | 6/1989 | Ravet et al. | 106/487 |
| 4,889,885 | 12/1989 | Usuki et al. | 524/443 |
| 4,894,411 | 1/1990 | Okada et al. | 524/710 |
| 4,920,171 | 4/1990 | Hutton, Jr. et al. | 524/446 |
| 5,032,546 | 7/1991 | Giannelis et al. | 501/3 |
| 5,032,547 | 7/1991 | Giannelis et al. | 501/3 |
| 5,091,462 | 2/1992 | Fukui et al. | 524/504 |
| 5,102,948 | 4/1992 | Deguchi et al. | 524/789 |
| 5,164,440 | 11/1992 | Deguchi et al. | 524/444 |
| 5,164,460 | 11/1992 | Yano et al. | 624/445 |
| 5,204,078 | 4/1993 | Tateyama et al. | 423/331 |
| 5,206,284 | 4/1993 | Fukui et al. | 524/504 |
| 5,229,451 | 7/1993 | Carter et al. | 524/493 |
| 5,230,893 | 7/1993 | Gotou et al. | 424/409 |
| 5,248,720 | 9/1993 | Deguchi et al. | 524/444 |
| 5,326,500 | 7/1994 | Friedman et al. | 252/378 |
| 5,340,558 | 8/1994 | Friedman et al. | 423/328.1 |
| 5,385,776 | 1/1995 | Maxfield et al. | 428/297 |
| 5,391,437 | 2/1995 | Miyasaka et al. | 528/425.5 |
| 5,414,042 | 5/1995 | Yasue et al. | 524/789 |
| 5,428,094 | 6/1995 | Tokoh et al. | 524/379 |
| 5,506,046 | 4/1996 | Andersen et al. | 524/446 |
| 5,508,072 | 4/1996 | Andersen et al. | 524/446 |

FOREIGN PATENT DOCUMENTS

| | | |
|---|---|---|
| 0 358 415 A1 | 3/1990 | European Pat. Off. . |
| 0 479 031 A1 | 4/1992 | European Pat. Off. . |
| 1146668 | 3/1969 | United Kingdom . |
| WO 93/04117 | 3/1993 | WIPO . |
| WO 93/04118 | 3/1993 | WIPO . |

OTHER PUBLICATIONS

K. Suzuki, et al., "Preparation Of Delaminated Clay Having A Narrow Micropore Distribution In The Presence Of Hydroxyaluminum Cations And Polyvinyl Alcohol", Clays and Clay Minerals, vol. 36, No. 2, 1988, pp. 147–152.

R. Levy, et al., "Interlayer Adsorption of Polyvinylpyrrolidone On Montmorillonite", Journal of Colloid and Interface Science, vol. 50, No. 3, Mar. 1975, pp. 442–450.

D.J. Greenland, "Adsorption Of Polyvinyl Alcohols By Montmorillonite", Journal of Colloid Science, 18, (1963) pp. 647–664.

R.A. Vaia, et al., "Synthesis and Properties of Two–Dimensional Nanostructures by Direct Intercalation of Polymer Melts in Layered Silicates", Chem. Mater. 1993, 5, pp. 1694–1696.

R.A. Vaia, et al., "New Polymer Electrolyte Nanocomposites: Melt Intercalation of Poly(ethylene oxide) in Mica–Type Silicates", Advanced Materials 1995, 7, No. 2, pp. 154–156.

A. Akelah, et al., "Synthesis and Characterization of Epoxyphilic montmorillonites", Clay Minerals (1994) 29, pp. 169–178.

C.E. Clapp, et al., "Adsorption Studies Of A Dextran On Montmorillonite", Trans. 9th Int. Cong. Soil Sci., 1968, vol. 1, pp. 627–634.

H.G.G. Dekking, "Preparation And Properties Of Some Polymer–Clay Compounds", Clays and Clay Minerals, 1964, 12, pp. 603–616.

A. Usuki, et al., "Characterization and Properties of Nylon 6—Clay Hybrid", (source and date unknown), pp. 651–652.

G.W. Brindley, et al., "Preparation And Solvatio Properties Of Some Variable Charge Montmorillonites", Clay and Clay Minerals, 1971, vol. 18, pp. 399–404.

A. Okada, et al., "A Solid State NMR Study On Crystalline Forms Of Nylon 6", Journal of Applied Polymer Science, (1989), vol. 37, pp. 1363–1371.

A. Usuki, et al., "Swelling Behavior Of Montmorillonite Cation Exchanged For ω–Amino Acids by ε–Caprolactam, J. Mater. Res., vol. 8, No. 5, May 1993, pp. 1174–1178.

Y. Kojima, et al., "One–Pot Synthesis Of Nylon 6–Clay Hybrid", Journal of Polymer Science: Part A: Polymer Chemistry, vol. 31, (1993), pp. 1755–1758.

Y. Kojima, et al., "Fine Structure Of Nylon–6–Clay Hybrid", Journal of Polymer Science: Part B: Polymer Physics, vol. 32 (1994), pp. 625–630.

B.K.G. Theng, "Clay–Polymer interactions: Sumary And Perspectives", Clays and Clay Minerals, vol. 30, No. 1 (1982) pp. 1–9.

Sugahara et al., "Clay–organic nano–composite; preparation of a kaolinitepoly(vinylpyrrolidone) intercalation compound," Journal of the Ceramic Society of Japan, International Edition, vol. 100, No. 4, Apr. 1, 1996, pp. 420–423.

Ogawa et al., "Preparation of montmorillonite–polyacrylamide intercalation compounds and the water absorbing property," Clay Science, vol. 7, 1989, Tokyo, Japan, pp. 243–251.

Wu et al., "Structural, thermal, and electrical characterization of layered nanocomposites derived from sodium–montmorillonite and polyethers." Chemical Abstract, vol. 119, No. 4, Jul. 26, 1993, Columbus, Ohio, US, Abstract No. 31017r.

Chemical Abstracts, vol. 118, No. 26, Jun. 28, 1993, Columbus, O., Abstract #257609b.

Yano et al., "Synthesis and properties of polyimide–clay hybrid," Polymer Preprints, ACS, Apr. 1991, pp. 65–66.

Giannelis et al., "Synthesis and processing of ceramics: Scientific issues," Materials Research Society Symposium Proceedings, vol. 249 (1992), pp. 547–558.

FIG. 1  ⊖ Na  ⊖ Mg  ○ Al  ○x○ ⌀ SI

INTERCALATES AND EXFOLIATES FORMED WITH ORGANIC PESTICIDE COMPOUNDS AND COMPOSITIONS CONTAINING THE SAME

FIELD OF THE INVENTION

The present invention is directed to intercalated pesticides manufactured by intercalation of one or more organic pesticide compounds between planar layers of a swellable layered material. More particularly, the present invention is directed to intercalates having at least one layer of organic pesticide compound sorbed on the internal surfaces of adjacent layers of the planar platelets of a layered material, such as a phyllosilicate, preferably a smectite clay, to expand the interlayer spacing to at least about 5 Å, preferably at least about 10 Å, more preferably to at least about 20 Å, and most preferably to at least about 30 Å, up to about 100 Å, or disappearance of periodicity. The intercalated layered materials have at least one layer of pesticide compound sorbed on the internal surfaces between adjacent layers of the planar platelets of the layered material. The resulting intercalates are a combination of organophilic and hydrophilic, and, if desired, can be exfoliated to individual platelets. The intercalates or exfoliates can be combined with an organic solvent to form a viscous pesticide composition or a thixotropic gel.

BACKGROUND OF THE INVENTION AND PRIOR ART

Calcined clays traditionally have been used as carriers for granular pesticides. Granular pesticides having a calcined clay carrier are limited because such carriers can accommodate no more than about 10% by weight of a pesticide. The amount of pesticide is limited because the pesticide merely enters the pore structure of the calcined clay. When the available sites in the pore structure are filled, then no further pesticide can be held by the calcined clay. If the available surface area of the carrier was greater, then the amount of pesticide in a granular product could be increased up to about 30% to 40% by weight of the pesticide granule.

It also is well known that phyllosilicates, such as smectite clays, e.g., sodium montmorillonite and calcium montmorillonite, can be treated with organic molecules, such as organic ammonium ions, to intercalate organic molecules between adjacent, planar silicate layers, for bonding the organic molecules with a polymer to intercalate the polymer between the layers, thereby substantially increasing the interlayer (interlaminar) spacing between the adjacent silicate layers. The thus-treated, intercalated phyllosilicates, having interlayer spacings of at least about 10 Å and up to about 100 Å, then can be exfoliated, i.e., the silicate layers are separated, e.g., mechanically, by high shear mixing. The individual silicate layers, when admixed with a matrix polymer, before, after or during the polymerization of the matrix polymer, e.g., a polyamide—see U.S. Pat. Nos. 4,739,007; 4,810,734; and 5,385,776—have been found to substantially improve one or more properties of the polymer, such as mechanical strength and/or high temperature characteristics.

Examples of such prior art composites, also called "nanocomposites," are disclosed in published PCT disclosure WO 93/04118 and U.S. Pat. No. 5,385,776, disclosing the admixture of individual platelet particles derived from intercalated layered silicate materials, with a polymer to form a polymer matrix having one or more properties of the matrix polymer improved by the addition of the exfoliated intercalate. As disclosed in WO 93/04118, the intercalate is formed (the interlayer spacing between adjacent silicate platelets is increased) by adsorption of a silane coupling agent or an onium cation, such as a quaternary ammonium compound, having a reactive group which is compatible with the matrix polymer. Such quaternary ammonium cations are well known to convert a highly hydrophilic clay, such as sodium or calcium montmorillonite, into an organophilic clay capable of sorbing organic molecules.

A publication that discloses direct intercalation (without solvent) of polystyrene and poly(ethylene oxide) in organically modified silicates is Richard A. Vaia et al., "Synthesis and Properties of Two-Dimensional Nanostructures by Direct Intercalation of Polymer Melts in Layered Silicates," Chem. Mater., 5:1694–1696(1993). Also, as disclosed in Richard A. Vaia et al., "New Polymer Electrolyte Nanocomposites: Melt Intercalation of Poly(Ethylene Oxide) in Mica-Type Silicates," Adv. Materials, 7, No. 2: (1985), pp. 154–156, poly(ethylene oxide) can be intercalated directly into sodium (Na) montmorillonite and lithium (Li) montmorillonite by heating to 80° C. for 2–6 hours to achieve a d-spacing of 17.7 Å. The intercalation is accompanied by displacing water molecules, disposed between the clay platelets, with polymer molecules. Apparently, however, the intercalated material could not be exfoliated and was tested in pellet form. It was quite surprising to one of the authors of these articles that exfoliated material could be manufactured in accordance with the present invention.

Previous attempts to intercalate polyvinylpyrrolidone (PVP), polyvinyl alcohol (PVA) and poly(ethylene oxide) (PEO) between montmorillonite clay platelets met with little success. As described in Levy et al., "Interlayer Adsorption of Polyvinylpyrrolidone on Montmorillonite," Journal of Colloid and Interface Science, Vol. 50, No. 3, March 1975, pages 442–450, attempts were made to sorb PVP (40,000 average M.W.) between monoionic montmorillonite clay platelets (Na, K (potassium), Ca (calcium), and Mg (magnesium)) by successive washes with absolute ethanol, and then attempting to sorb the PVP by contact with 1% PVP/ethanol/water solutions, with varying amounts of water ($H_2O$), via replacing the ethanol solvent molecules that were sorbed in washing (to expand the platelets to about 17.7 Å). Only the sodium montmorillonite had expanded beyond a 20 Å basal spacing (e.g., 26 Å and 32 Å), at 5+% $H_2O$, after contact with the PVP/ethanol/$H_2O$ solution. It was concluded that the ethanol was needed to initially increase the basal spacing for later sorption of PVP, and that water did not directly affect the sorption of PVP between the clay platelets (Table II, page 445), except for sodium montmorillonite. The sorption was time consuming and difficult and met with little success.

Further, as described in Greenland, "Adsorption of Polyvinyl Alcohols by Montmorillonite," Journal of Colloid Sciences, Vol. 18, pages 647–664 (1963), polyvinyl alcohols containing 12% residual acetyl groups could increase the basal spacing by only about 10 Å due to the sorbed polyvinyl alcohol (PVA). As the concentration of polymer in the intercalant polymer-containing solution was increased from 0.25% to 4%, the amount of polymer sorbed was substantially reduced, indicating that sorption might only be effective at polymer concentrations in the intercalant polymer-containing composition on the order of 1% by weight polymer, or less. Such a dilute process for intercalation of polymer into layered materials would be exceptionally costly in drying the intercalated layered materials for separation of intercalate from the polymer carrier, e.g., water, and, therefore, apparently no further work was accomplished toward commercialization.

In accordance with one embodiment of the present invention, intercalates are prepared by contacting a phyllosilicate either with water, or with an aqueous solution of a water-soluble polymer and/or a water-miscible organic solvent, like an alcohol, followed by contact with a monomeric organic pesticide compound or a solution of a pesticide compound. Typically, the pesticide compound has a polar organic moiety, such as a carbonyl functionality, like, for example, a carboxylic acid, or salt thereof, an ester, an amide, an aldehyde, a ketone, or a mixture thereof. The pesticide also can contain other polar organic moieties in addition to, or in place of, the carbonyl functionality, such as, for example, a sulfur-oxygen moiety, a phosphorus-oxygen moiety, a cyano moiety, or a nitro moiety. If the intercalate is prepared using an aqueous solution of a water-soluble polymer and/or a water-miscible organic solvent, then nonpolar pesticides, like chlordane and lindane, can be intercalated between clay platelets.

The addition of a pesticide or pesticide solution displaces the water and water-soluble polymer, if present, disposed between the clay platelets of the intercalate. The pesticide, therefore, displaces the water and water-soluble polymer between the clay platelets. The intercalated pesticide then is dried to remove the water, and pelletized to provide a granular pesticide containing up to 40% by weight of a pesticide.

In accordance with an important feature of the present invention, best results are achieved by using an aqueous solution of a water-soluble polymer, like polyvinylalcohol, and/or a water-miscible organic solvent, to first intercalate, i.e., activate, the clay, then using an organic pesticide compound having at least one polar organic moiety, and preferably a carbonyl functionality, in a concentration of at least about 2%, preferably at least about 5%, more preferably at least about 10%, by weight, based on the weight of organic pesticide compound and carrier (e.g., water, an organic solvent for the pesticide compound, or a mixture thereof) to achieve better sorption of the organic pesticide compound between phyllosilicate platelets. If the pesticide is a solid at intercalating temperature, it can be dissolved in a solvent. If the pesticide is a liquid compound at intercalating temperature, the pesticide can be intercalated between phyllosilicate platelets without using a solvent.

Regardless of the concentration of organic pesticide compound in a solvent, a water-soluble polymer:layered material ratio of at least 1:20, preferably at least 1:10, more preferably at least 1:4, and most preferably about 1:2, by weight, achieves efficient intercalation of the organic pesticide compound between adjacent platelets of the layered material. A water-miscible organic solvent can be used in place of the water-soluble polymer. It has been theorized that water, or aqueous solution of water-soluble polymer, intercalates between the clay layers to activate the clay, then the organic pesticide compound displaces the water and water-soluble polymer and is bonded to the silicate platelets via chelation-type bonding with the exchangeable cation, or via electrostatic or dipole/dipole bonding. The sorption of the water and/or water-soluble polymer, causes separation or added spacing between adjacent silicate platelets. An extrusion process accelerates intercalation of the pesticide between activated clay platelets.

For simplicity of description, all organic pesticide compounds are hereinafter termed an "intercalant pesticide." The water-soluble polymers are hereinafter termed an "intercalant polymer." In this manner, the water-soluble polymers, and subsequently the organic pesticides, are sufficiently sorbed to increase the interlayer spacing of the phyllosilicate in the range of about 5 Å to about 100 Å, preferably at least about 10 Å, for easier and more complete exfoliation, if desired, in a commercially viable process, regardless of the particular phyllosilicate or intercalant pesticide.

In accordance with the present invention, it has been found that a phyllosilicate, such as a smectite clay, that has been activated with water or an aqueous solution of a water-soluble polymer and/or a water-miscible organic solvent, can be intercalated by sorption of organic pesticide compounds having a polar moiety, like carbonyl functionality, to provide bonding of the polar moiety to the internal surfaces of the layered material by a mechanism selected from the group consisting of ionic complexing, electrostatic complexing, chelation, hydrogen bonding, dipole/dipole interaction, Van Der Waals forces, and any combination thereof. Such bonding between the polar moieties of one or two intercalant pesticide molecules and the metal cations bonded to the inner surfaces of the phyllosilicate platelets provides adherence between the organic pesticide molecules and the platelet inner surfaces of the layered material. Activation of the clay and sorption and bonding of a platelet metal cation between two electronegative atoms of the intercalant pesticide molecules, like oxygen, sulfur, or nitrogen, for example, increases the interlayer spacing between adjacent silicate platelets or other layered material to at least about 5 Å, preferably to at least about 10 Å, and more preferably at least about 20 Å, and most preferably in the range of about 30 Å to about 100 Å. In addition, if a water-soluble polymer is used to activate the phyllosilicate, the intercalant polymer provides sufficient interlayer spacing such that pesticides lacking a polar group can be intercalated into the clay.

The intercalated clay containing a pesticide, i.e., intercalated pesticide product, can be used directly as a pesticide product. The intercalated pesticide also can be used as the active ingredient in a granular, dust, or wettable powder pesticide composition by admixture of the solid pesticide intercalant with ingredients well known in the art.

Such intercalated pesticides also easily can be exfoliated, if desired, into individual phyllosilicate platelets before or during admixture with a liquid carrier or solvent, for example, one or more monohydric alcohols, such as methanol, ethanol, propanol, and/or butanol, polyhydric alcohols, such as glycerols and glycols, e.g., ethylene glycol, propylene glycol, butylene glycol, glycerine, and mixtures thereof, aldehydes, ketones, carboxylic acid esters, amines, hydroxyethers, like ethylene glycol monobutyl ether, glycol ether esters, like cellosolve acetate, aromatic or aliphatic hydrocarbons, and other organic solvents, like DMSO, DMF, or HMPA. The exfoliated platelets can be used for delivery of any active hydrophobic or hydrophilic organic pesticide compound, such as a contact or a systemic pesticide compound, dissolved or dispersed in the carrier or solvent to provide either a solid, as a granular, dust, or wettable powder, or a thixotropic composition.

DEFINITIONS

Whenever used in this specification, the terms set forth shall have the following meanings:

"Layered material" shall mean an inorganic material, such as a smectite clay mineral, that is in the form of a plurality of adjacent, bound layers and has a thickness, for each layer, of about 3 Å to about 50 Å, preferably about 10 Å.

"Platelets" shall mean individual layers of the layered material.

"Intercalate" or "Intercalated" shall mean a layered material that includes a water-soluble polymer or an organic pesticide compound disposed between adjacent platelets of the layered material to increase the interlayer spacing between the adjacent platelets to at least about 5 Å, preferably at least about 10 Å.

"Intercalated Pesticide Product" shall mean an intercalated clay containing a pesticide.

"Intercalation" shall mean a process for forming an intercalate.

"Intercalant Pesticide" shall mean a pesticide compound having a polar moiety that is sorbed between platelets of the layered material and complexes with the platelet surfaces to form an intercalate.

"Intercalant Polymer" shall mean a water-soluble polymer that is sorbed between platelets of the layer material, expands the space between the platelet materials, and complexes with the platelet surfaces to form an intercalate.

"Intercalating Carrier" shall mean a carrier comprising water with or without an organic solvent used together with an intercalant pesticide to form an intercalating composition capable of achieving intercalation of the layered material.

"Intercalating Composition" shall mean a composition comprising an intercalant pesticide, an intercalating carrier for the intercalant pesticide, and a layered material.

"Exfoliate" or "Exfoliated" shall mean individual platelets of an intercalated layered material so that adjacent platelets of the intercalated layered material can be dispersed individually throughout a carrier material, such as a solid carrier, water, an alcohol or glycol, or any other organic solvent.

"Exfoliation" shall mean a process for forming an exfoliate from an intercalate.

SUMMARY OF THE INVENTION

In brief, the present invention is directed to intercalates, and to exfoliates therefrom, formed by contacting a layered phyllosilicate with water or an aqueous solution of a water-soluble polymer and/or a water-miscible organic solvent, and with an organic pesticide (i.e., intercalant pesticide), typically having at least one polar moiety, to sorb or intercalate the intercalant pesticide, or mixture of intercalant pesticides, between adjacent phyllosilicate platelets. Sufficient intercalant pesticide is sorbed between adjacent phyllosilicate platelets to expand the spacing between adjacent platelets (interlayer spacing) to a distance of at least about 5 Å, preferably to at least about 10 Å (as measured after water removal, to a maximum water content of 5% by weight, based on the dry weight of the layered material) and more preferably in the range of about 20 Å to about 45 Å. The intercalate, after drying, contains up to about 40% by weight pesticide. If desired, the intercalate can be exfoliated easily, sometimes naturally, i.e., without shearing. At times, the intercalate requires shearing that can be accomplished easily, e.g., when mixing the intercalate with an organic solvent carrier, such as an organic hydrocarbon, the platelets are obtained by exfoliation of the intercalated phyllosilicate.

The intercalant pesticide has an affinity for the phyllosilicate so that it expels water and intercalant polymer, is sorbed between silicate platelets, and is maintained associated with the silicate platelets in the interlayer spaces, even after exfoliation. In accordance with the present invention, the intercalant pesticide typically includes a polar moiety, for example a carbonyl functionality, like a carboxylic acid, to be sufficiently bound between clay platelets by a mechanism selected from the group consisting of ionic complexing, electrostatic complexing, chelation, hydrogen bonding, dipole/dipole interactions, Van Der Waals forces, and any combination thereof. However, the pesticide can be free of a polar moiety if the phyllosilicate first is activated by contact with an aqueous solution of a water-soluble polymer, i.e., an intercalant polymer.

Such bonding, via metal cations of the phyllosilicate sharing electrons with two electronegative atoms of one intercalant pesticide molecule or with two adjacent intercalant pesticide molecules, to an inner surface of the phyllosilicate platelets provides adherence between the pesticide molecules and the platelet inner surfaces of the layered material. The electronegative atoms can be, for example, oxygen, sulfur, nitrogen, and combinations thereof. Atoms having a sufficient electronegativity to bond to metal cations on the inner surface of the platelets preferably have an electronegativity of at least 2.0, and more preferably at least 2.5 on the Pauling Scale. A "polar moiety" or "polar group" is defined as a moiety having two adjacent atoms that are bonded covalently and preferably have a difference in electronegativity of at least 0.5 electronegativity units on the Pauling Scale. Intercalant pesticides having a polar moiety have sufficient affinity for the phyllosilicate platelets to maintain sufficient interlayer spacing for exfoliation, without the need for coupling agents or spacing agents, such as the onium ion or silane coupling agents disclosed in the above-mentioned prior art. Intercalant pesticides lacking a polar moiety enter the space between two adjacent platelets because of the relatively large spacing provided by an intercalant polymer during activation of the clay.

A schematic representation of the charge distribution on the surfaces of a sodium montmorillonite clay is shown in FIGS. 1–3. As shown in FIGS. 2 and 3, the location of surface Na (sodium) cations with respect to the location of $O_x$ (oxygen), Mg (magnesium), Si (silicon), and Al (aluminum) atoms (FIGS. 1 and 2) results in a clay surface charge distribution as schematically shown in FIG. 3. The positive-negative charge distribution over the entire clay surface provides for excellent dipole-dipole attraction of pesticide compounds having a polar moiety on the surfaces of the clay platelets.

Intercalate-containing and/or exfoliate-containing compositions can be in the form of a solid, or a viscous liquid or stable thixotropic gel, that is not subject to phase separation. Either form can be used to deliver the active pesticide compound. In either form, the layered material is activated, then intercalated by contact with an intercalant pesticide, by mixing and/or extruding, to intercalate the pesticide between adjacent phyllosilicate platelets, and finally, optionally, separating (i.e., exfoliating) the intercalated layered material into individual platelets.

The amount of water and intercalant polymer used during the activation process varies, depending upon the amount of shear imparted to the layered material during contact with the intercalant pesticide and solvent. In one method, the layered material is pug milled or extruded at a water content (with or without a water-soluble polymer) of about 25% by weight to about 50% by weight water, preferably about 35% to about 40% by weight water, based on the dry weight of the layered material, e.g., clay. Typically, a water-miscible organic solvent is present to assist the water activate the clay. An organic solvent often is not present if a water-soluble polymer is used.

In another method, the clay and water (or aqueous solution of intercalant polymer and/or water-miscible organic solvent) are slurried, with at least about 25% by weight water, preferably at least about 65% by weight water, based on the dry weight of the layered material, e.g., preferably less than about 20% by weight clay in water, based on the total weight of layered material and water, more preferably less than about 10% layered material in water, with the subsequent addition of about 2% by weight to about 90% by weight intercalant pesticide, based on the dry weight of the layered material, after activation of the clay.

Activation of the clay and sorption of the intercalant pesticide should be sufficient to achieve expansion of adjacent platelets of the layered material (when measured dry) to an interlayer spacing of at least about 5 Å, preferably to a spacing of at least about 10 Å, more preferably a spacing of at least about 20 Å, and most preferably a spacing of about 30 Å to about 45 Å. To achieve intercalates that can be exfoliated easily using the pesticide intercalants disclosed herein, the weight ratio of intercalant pesticide to layered material, preferably a water-swellable smectite clay such as sodium bentonite, in the intercalating composition should be at least about 1:20, preferably at least about 1:12 to 1:10, more preferably at least about 1:4, and most preferably about 1:3. It is preferred that the concentration of intercalant pesticide, based on the total weight of intercalant pesticide plus intercalant carrier (i.e., water plus any organic liquid solvent) is at least about 15% by weight, more preferably at least about 20% by weight, intercalant pesticide, for example about 20% to about 90% by weight intercalant pesticide, based on the weight of intercalant pesticide plus intercalant carrier during intercalation.

The intercalates of the present invention are increased in interlayer spacing step-wise. If the phyllosilicate is contacted with an intercalant polymer-containing or an intercalant pesticide-containing composition containing less than about 16% by weight intercalant polymer or pesticide, e.g., 10% to about 15% by weight, based on the dry weight of the phyllosilicate, a monolayer width of intercalant polymer or pesticide is sorbed (i.e., intercalated) between the adjacent platelets of the layered material. A monolayer of intercalant intercalated between platelets increases the interlayer spacing to about 5 Å to less than about 10 Å. When the amount of intercalant pesticide, or intercalant polymer, is in the range of about 16% to less than about 35% by weight, based on the weight of the dry layered material, the intercalant is sorbed in a bilayer, thereby increasing the interlayer spacing to about 10 Å to about 16 Å. At an intercalant pesticide, or intercalant polymer, loading of about 35% to less than about 55% intercalant, based on the dry weight of the layered material contacted, the interlayer spacing is increased to about 20 Å to about 25 Å, corresponding to three layers of intercalant sorbed between adjacent platelets of the layered material. At an intercalant loading of about 55% to about 80% intercalant, based on the dry weight of the layered material, the interlayer spacing will be increased to about 30 Å to about 35 Å, corresponding to 4 and 5 layers of intercalant sorbed (i.e., intercalated) between adjacent platelets of the layered material.

Such interlayer spacings have never been achieved by direct intercalation of intercalant polymers or intercalant pesticides, without prior sorption of an onium or silane coupling agent, and provides easier and more complete exfoliation for, or during, incorporation of the platelets into a carrier or solvent, to provide unexpectedly viscous liquid compositions for delivery of an active pesticide that is dispersed in the carrier or solvent. Such compositions, especially the high viscosity thixotropic gels, are particularly useful pesticide compositions because the environmental and toxicological dangers associated with spills and spill clean-up of liquid pesticides are overcome. The thixotropic, high viscosity gels are easy to confine and collect if spilled. In addition, the thixotropic gels can be dissolved or dispersed in an appropriate solvent by a pesticide applicator to provide a spray solution.

After exfoliation of the intercalates, the platelets of the intercalate are predominantly completely separated into individual platelets and the originally adjacent platelets no longer are retained in a parallel, spaced disposition, but are free to move as predominantly individual intercalant pesticide-coated (either continuously or discontinuously) platelets throughout a carrier or solvent material to maintain viscosity and thixotropy of the carrier material. The predominantly individual phyllosilicate platelets, having their platelet surfaces complexed with intercalant pesticide molecules, are randomly, homogeneously and uniformly dispersed, predominantly as individual platelets, throughout the carrier or solvent to achieve new and unexpected viscosities in the carrier/platelet compositions even after addition of additional active organic compounds, such as a second pesticide or a pesticide adjuvant, for administration of the intercalant pesticide and additional active organic compounds from the composition.

As recognized, the thickness of the exfoliated, individual platelets (about 10 Å) is relatively small compared to the size of the flat opposite platelet faces. The platelets have an aspect ratio in the range of about 200 to about 2,000. Dispersing such finely divided platelet particles into an organic liquid carrier imparts a very large area of contact between carrier and platelet particles, for a given volume of particles, and a high degree of platelet homogeneity in the composition. Platelet particles of high strength and modulus, dispersed at sub-micron size (nanoscale), impart a higher viscosity to an organic liquid carrier than do comparable loadings of conventional particles of micron size.

BRIEF DESCRIPTION OF THE DRAWINGS

FIG. 1 is a schematic representation of a top view (ab-projection) of two layers of sodium montmorillonite clay showing the upper oxygen atoms of silicon tetrahedral sheet with sodium cations in hexagonal holes and octahedral cations of aluminum and magnesium;

FIGS. 15 and 16 are x-ray diffraction patterns, respectively, of wet and dry samples of Example #9a;

FIGS. 23 and 24 are x-ray diffraction patterns, respectively, of wet and dry samples of Example #12a;

DETAILED DESCRIPTION OF THE PREFERRED EMBODIMENTS

Figure 2:
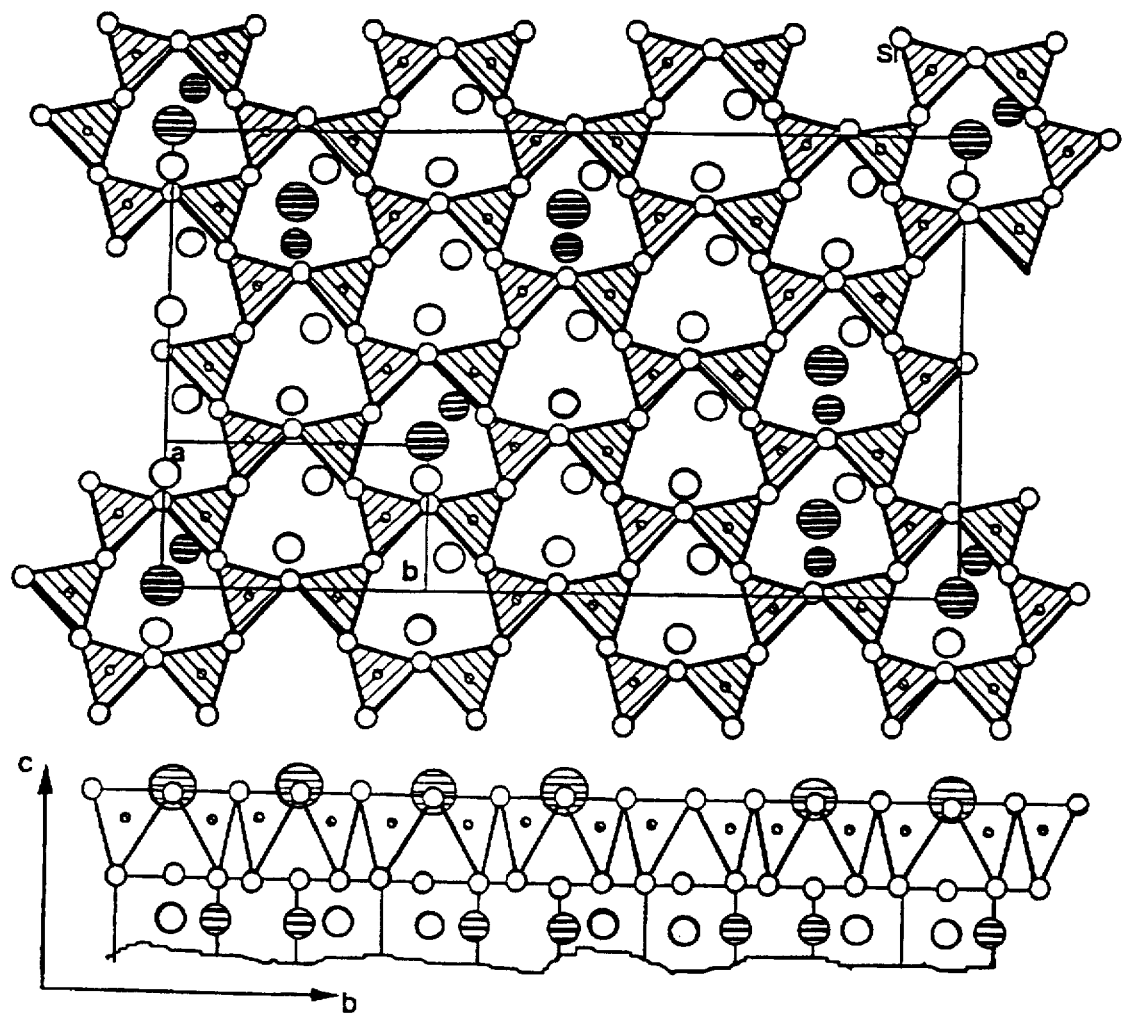
FIG. 2 is a side view (bc-projection) of the schematic representation of two smectite layers FIG. 1.

To form the intercalated and, optionally, exfoliated pesticides of the present invention, the layered material, e.g., the phyllosilicate, is activated, i.e., swelled or intercalated, by water, an intercalant polymer, a water-miscible organic solvent, or mixture thereof, followed by sorption of an intercalant pesticide. In accordance with a preferred embodiment of the present invention, the activated phyllosilicate includes at least 4% by weight water, up to about 5,000% by weight water, based on the dry weight of the phyllosilicate, preferably about 7% to about 100% water, more preferably about 25% to about 50% by weight water, prior to or during contact with the intercalant pesticide to achieve sufficient intercalation, especially if the pesticide intercalate will be exfoliated. Preferably, the phyllosilicate includes at least about 4% by weight water before contact with the intercalant pesticide for efficient intercalation.

The amount of intercalant pesticide in contact with the phyllosilicate, especially for efficient exfoliation, should provide an intercalant pesticide/phyllosilicate weight ratio (based on the dry weight of the phyllosilicate) of at least about 1:20, preferably at least about 3:20, and more preferably about 4–14:20, to provide efficient sorption and complexing (i.e., intercalation) of the intercalant pesticide between the platelets of the layered material, e.g., phyllosilicate. Intercalation of the intercalant pesticide, especially nonpolar intercalant pesticides, is facilitated by using an intercalant polymer and water to activate the phyllosilicate.

The intercalant pesticides are introduced in the form of a solid or liquid composition (neat or aqueous, with or without a polar or nonpolar organic solvent, e.g., an aliphatic hydrocarbon, such as heptane) having an intercalant pesticide concentration of at least about 2%, preferably at least about 5%, more preferably at least about 10%, and most preferably at least about 50% to about 100% by weight intercalant pesticide, based on the weight of the pesticide compound and carrier, for intercalant pesticide sorption. The intercalant pesticide can be added as a solid with the addition to the layered material/intercalant pesticide blend of about 20% water, preferably at least about 30% water to about 5,000% water or more, based on the dry weight of layered material.

Preferably about 30% to about 50% water, more preferably about 30% to about 40% by weight water, based on the dry weight of the layered material, is used when extruding or pug milling, so that less water is sorbed by the intercalate, thereby necessitating less drying energy after intercalation. The pesticide intercalants can be introduced into the spaces between every layer, nearly every layer, or at least a predominance of the layers of the layered material such that the platelet particles, if subsequently exfoliated, are preferably predominantly less than about 5 layers in thickness, more preferably, predominantly about 1 or 2 layers in thickness, and most preferably, predominantly single platelets.

Any swellable layered material that sufficiently sorbs the intercalant pesticide to increase the interlayer spacing between adjacent phyllosilicate platelets to at least about 10 Å (when the phyllosilicate is measured dry) can be used in the practice of this invention. Useful swellable layered materials include phyllosilicates, such as smectite clay minerals, e.g., montmorillonite, particularly sodium montmorillonite, magnesium montmorillonite and/or calcium montmorillonite, nontronite, beidellite, volkonskoite, hectorite, saponite, sauconite, sobockite, stevensite, svinfordite, vermiculite, and the like. Other useful layered materials include micaceous minerals, such as illite and mixed layered illite/smectite minerals, such as rectorite, tarosovite, ledikite and admixtures of illites with the clay minerals named above.

Other layered materials having little or no charge on the layers can be used in this invention provided they can be intercalated with the intercalant pesticides to expand their interlayer spacing to at least about 5 Å, preferably at least about 10 Å. Preferred swellable layered materials are phyllosilicates of the 2:1 type having a negative charge on the layers ranging from about 0.15 to about 0.9 charges per formula unit and a commensurate number of exchangeable metal cations in the interlayer spaces. Most preferred layered materials are smectite clay minerals such as montmorillonite, nontronite, beidellite, volkonskoite, hectorite, saponite, sauconite, sobockite, stevensite, and svinfordite.

As used herein the "interlayer spacing" refers to the distance between the internal faces of the adjacent layers as they are assembled in the layered material before any delamination (i.e., exfoliation) takes place. The interlayer spacing is measured when the layered material is "air dry," i.e., contains 3–10% by weight water, preferably about 3–6% by weight water, e.g., 5% by weight water based on the dry weight of the layered material. The preferred clay materials generally include interlayer cations such as $Li^+$ (lithium), $Na^+$, $Ca^{+2}$ (calcium), $K^+$ (potassium) $M^{+2}$, $NH_4^+$ (ammonium), and the like, including mixtures thereof.

In accordance with a preferred embodiment of the present invention, the phyllosilicate is contacted with an aqueous solution of an intercalant polymer to provide a sufficient spacing between adjacent platelets to permit intercalation of polar and/or nonpolar pesticides. The intercalant polymer should be water soluble (herein defined as sufficiently soluble such that at least 0.1 gram of the polymer will dissolve per 100 grams of distilled water at 25° C.). In accordance with a preferred embodiment of the present invention, the intercalant polymer includes a functionality selected from the group consisting of a carbonyl, carboxyl, hydroxyl, amine, amide, ether, ester, sulfate, sulfonate, sulfinate, sulfamate, phosphate, phosphonate, phosphinate, or an aromatic ring to be sufficiently complexed or bound to the platelet surfaces of the layered material. Such intercalant polymers have sufficient affinity for the phyllosilicate platelets to provide sufficient interlayer spacing for exfoliation, e.g., about 5 Å to about 100 Å, preferably about 10 Å to about 50 Å, and to maintain attachment to the surfaces of the platelets, without the need for coupling agents or spacing agents, such as the onium ion or silane coupling agents disclosed in the above-mentioned prior art.

Sorption of the intercalant polymer should be sufficient to achieve expansion of adjacent platelets of the layered material (when measured dry, i.e., having a maximum of about 5% by weight water) to an interlayer spacing of at least about 5 Å, preferably a spacing of at least about 10 Å, more preferably a spacing of at least about 20 Å, and most preferably a spacing of about 30–45 Å. To achieve intercalates that easily incorporate a nonpolar pesticide or that can be exfoliated easily using the preferred water-soluble polymer intercalants disclosed herein, such as polyvinylpyrrolidone, polyvinyl alcohol, and mixtures thereof, the weight ratio of intercalant polymer to layered material, preferably a water-swellable smectite clay such as sodium bentonite, in the intercalating composition contacting the phyllosilicate should be at least about 1:20, preferably at least about 1:12 to 1:10, more preferably at least about 1:4, and most preferably about 1:3 to about 1:2. It is preferred that the concentration of polymer, based on the total weight of intercalant polymer plus intercalant carrier (water plus any organic liquid solvent) is at least about 15% by weight, more preferably at least about 20% by weight polymer, for example about 20%–30% to about 90% by weight polymer, based on the weight of polymer plus intercalant carrier (water plus any organic solvent) during intercalation.

In accordance with a preferred embodiment of the present invention, the combination of layered material and aqueous solution containing an intercalant polymer includes at least about 4% by weight water, up to about 5000% by weight water, based on the dry weight of the phyllosilicate, preferably about 7% to about 100% water, more preferably about 25% to about 50% by weight water, prior to or during contact with the intercalant polymer to achieve sufficient polymer intercalation. Preferably, the phyllosilicate includes at least about 4% by weight water before contact with the polymer for efficient intercalation. The amount of intercalant polymer in contact with the phyllosilicate for efficient exfoliation, should provide efficient sorption and complexing (intercalation) of the polymer between the platelets of the layered material, preferably about 16 to about 70 percent by weight intercalant polymer, based on the dry weight of the layered silicate material.

The preferred intercalant polymers are water-soluble and are added in the form of a solid or liquid (neat or aqueous solution or dispersion, with or without a liquid organic solvent, e.g., alcohol) having an intercalant polymer concentration of at least about 2%, preferably at least about 5%, more preferably at least about 50% to about 100%, by weight intercalant polymer, based on the dry weight of the layered material, for intercalant polymer sorption. The polymer can be added as a solid with the addition to the layered material/polymer blend of at least about 20% water, preferably at least about 30% water to about 5000% water or more, based on the dry weight of the layered material, with or without another solvent for the intercalant polymer, preferably about 30% to about 50% water, more preferably about 30% to about 40%. The intercalant polymer can be introduced into the spaces between every layer, nearly every layer, or at least a predominance of the layers of the layered material such that the subsequently exfoliated platelet particles are preferably, predominantly less than about 5 layers in thickness, more preferably, predominantly about 1 or 2 layers in thickness, and most preferably, predominantly single platelets.

The amount of intercalant polymer intercalated into the swellable layered materials useful in this invention, in order that nonpolar pesticide compounds can intercalate in the layered material, and such that the layered material can be easily exfoliated or delaminated into individual platelets, can vary substantially between about 10% and about 80%, based on the dry weight of the layered silicate material. In the preferred embodiments of the invention, amounts of intercalants polymers employed, with respect to the dry weight of layered material being intercalated, preferably range from about 8 grams of intercalant polymer/100 grams of layered material (dry basis), preferably at least about 10 grams of polymer/100 grams of layered material, to about 80 to about 90 grams intercalant polymer/100 grams of layered material. More preferred amounts are from about 20 grams intercalant polymer/100 grams of layered material to about 60 grams intercalant polymer/100 grams of layered material (dry basis).

The polymer intercalants are introduced into (i.e., sorbed within) the interlayer spaces of the layered material in one of two ways. In a preferred method of intercalating, the layered material and an intercalant polymer or intercalant polymer/water solution, or intercalant polymer, water and an organic solvent, are intimately mixed, e.g., by extrusion or pug milling. To achieve sufficient intercalation for exfoliation, the layered material/intercalant polymer blend contains at least about 8%, preferably at least about 10%, by weight intercalant polymer, based on the dry weight of the layered material. The intercalating carrier (preferably water, with or without an organic solvent) can be added by first solubilizing or dispersing the intercalant polymer in the carrier, or the dry intercalant polymer and relatively dry phyllosilicate (preferably containing at least about 4% by weight water) can be blended and the intercalating carrier added to the blend, or to the phyllosilicate prior to adding the dry intercalant polymer. In every case, it has been found that surprising sorption and complexing of intercalant polymer between platelets is achieved at relatively low loadings of intercalating carrier, especially water, e.g., at least about 4% by weight water, based on the dry weight of the phyllosilicate. When intercalating the phyllosilicate in slurry form (e.g., 900 pounds water, 100 pounds phyllosillicate, 25 pounds polymer) the amount of water can vary from a preferred minimum of at least about 30% by weight water, with no upper limit to the amount of water (the phyllosilicate intercalate is easily separated from the intercalating composition).

Alternatively, the intercalating carrier, e.g., water, with or without an organic solvent, can be added directly to the phyllosilicate prior to adding the intercalant polymer, either dry or in solution. Sorption of the intercalant polymer molecules can be performed by exposing the layered material to dry or liquid intercalant polymer compositions containing at least about 2%, preferably at least about 5%, by weight intercalant polymer, more preferably at least about 50% intercalant polymer, based on the dry weight of the layered material. Sorption can be aided by exposure of the intercalating composition to heat, pressure, ultrasonic cavitation, or microwaves.

In accordance with another method of intercalating the intercalant polymer between the platelets of the layered material and exfoliating the intercalate, the layered material, containing at least about 4% by weight water, preferably about 10% to about 15% by weight water, is blended with an aqueous solution of a water-soluble intercalant polymer in a ratio sufficient to provide at least about 8% by weight, preferably at least about 10% by weight, intercalant polymer, based on the dry weight of the layered material. The blend then preferably is extruded for faster intercation of the polymer with the layered material.

The preferred intercalant polymers are water-soluble, such as polyvinylpyrrolidone (PVP) having a repeating structure (I) as follows:

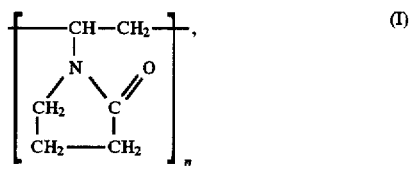

wherein n is a number from 2 to about 1500. The water-solubility of PVP can be adjusted according to (1) the degree of hydrolysis of the polyvinylpyrrolidone, and (2) by forming a metal salt of PVP, such as sodium or potassium. PVP can be hydrolyzed to the structure (II):

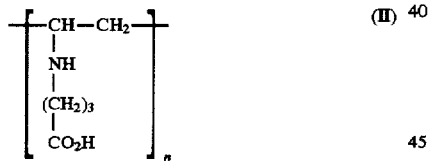

and the PVP, or copolymers of vinylpyrrolidone and a vinyl amide of γ-amine butyric acid, can be intercalated in the salt form, e.g., sodium or potassium polyvinylpyrrolidone polymers. Preferred PVP intercalants, and the following PVP derivatives, have a weight average molecular weight in the range of about 210 to about 100,000 or more, more preferably about 1,000 to about 40,000.

Other suitable water-soluble vinyl polymers include poly(vinyl alcohol)

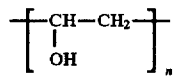

The polyvinyl alcohols (PVA) function best when they are essentially fully hydrolyzed, e.g., 5% or less acetyl groups, preferably 1% or less residual acetyl groups. A lower molecular weight PVA functions best, e.g., a weight average molecular weight of about 2,000 to about 10,000, but higher molecular weight PVA also functions, e.g., up to about 100,000.

The polyacrylic acid polymers and copolymers, and partially or fully neutralized salts, e.g., metal salts, are also suitable, having monomer units:

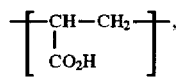

and are commercially available as CARBOPOL resins from B. F. Goodrich and PRIMAL resins from Rohm & Haas. Light cross-linking is acceptable, as long as water solubility is retained. Weight average molecular weights for the polyacrylic polymers and copolymers described above and below of about 10,000 or less, e.g., about 200 to about 10,000, intercalate more easily, but higher molecular weight polymers, up to about 100,000 or more, also function.

Other water-soluble derivatives of, and substituted, polyacrylic acids also are useful as intercalant polymers in accordance with the present invention, such as poly(methacrylic acid) (PMAA), having a repeating monomeric structure:

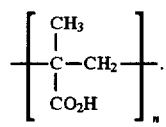

Similar water-soluble polymers and copolymers that are suitable in accordance with the present invention include poly(methacrylamide), or PMAAm, having a general repeating monomeric structure:

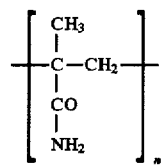

Poly(N,N-dimethylacrylamide), having the gener-al repeating monomeric structure:

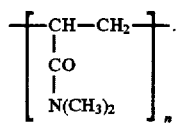

Poly(N-isopropylacrylamide), or PIPAAm, having the general repeating monomeric structure:

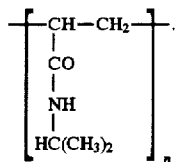

Poly(N-acetamidoacrylamide) having a general repeating monomeric structure:

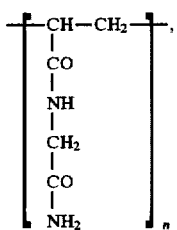

and poly(N-acetmidomethacrylamide) having a general repeating monomeric structure:

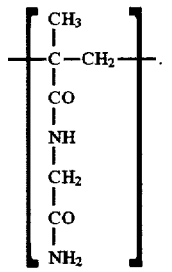

Water-soluble copolymers including any one or more of the above-described acrylic polymers also are useful in accordance with the principles of the present invention, including the acrylic interpolymers of polyacrylic acid and poly (methacrylic acid), polyacrylic acid with poly-(methacrylamide), and polyacrylic acid with methacrylic acid.

Other suitable water-soluble polymers include polyvinyloxazolidone (PVO) and polyvinylmethyloxazolidone (PVMO), having the general repeating monomeric structures:

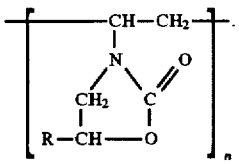

PVO: R = H
PVMO: R = CH₃

Also suitable are polyoxypropylene-polyoxyethylene block polymers that conform to the formulas:

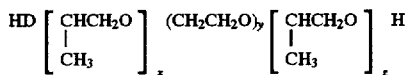

and

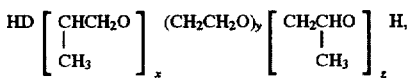

wherein x and z are each an integer in the range of about 4 to about 30, and y is an integer in the range of about 4 to about 100, for example Meroxapol 105, Meroxapol 108, Meroxapol 171, Meroxapol 172, Meroxapol 174, Meroxapol 178, Meroxapol 251, Meroxapol 252, Meroxapol 254, Meroxapol 255, Meroxapol 258, Meroxapol 311, Meroxapol 312, and Meroxapol 314.

Other suitable water-soluble/water-dispersible intercalant polymers include, but are not limited to, polyacrylamide and copolymers of acrylamide, acrylamide/sodium acrylate copolymer, acrylate/acrylamide copolymer, acrylate/ammonium methacrylate copolymer, acrylate/diacetoneacrylamide copolymers, acrylic/acrylate copolymers, adipic acid/dimethylaminohydroxypropyl diethylenetriamine copolymer, ammonium acrylate copolymers, ammonium styrene/acrylate copolymers, ammonium vinyl acetate/acrylate copolymers, AMP acrylate/diacetoneacrylamide copolymers, AMPD acrylate/diacetoneacrylamide copolymers, butyl benzoic acid/phthalic anhydride/trimethylolethane copolymer, cornstarch/acrylamide/sodium acrylate copolymer, diethylene glycolamine/epichlorohydrin/piperazine copolymer, dodecanedioic acid/cetearyl alcohol/glycol copolymers, ethylene/vinyl alcohol copolymer, ethyl ester of polyethyl-enimines (such as hydroxyethyl/PEI-1000 and hydroxyethyl PEI- 1500), isopropyl ester of PVM/MA copolymer, melamine/formaldehyde resin, methacryloyl ethyl betaine/methacrylate copolymers, methoxy PEG-22/dodecyl glycol copolymer, octadecene/maleic anhydride copolymer, octylacrylamide/acrylate/butylaminoethyl methacrylate copolymers, octyl-acrylamide/acrylate copolymers, PEG/dodecyl glycol co-polymers, polyethyleneimines (such as PEI-7, PEI-15, PEI-30, PEI-45, PEI-275, PEI-700, PEI-1000, PEI-1500, and PEI-2500), phthalic anhydride/glycerin/glycidyl decanoate copolymer, metal salts of acrylic and polyacrylic acid, polyaminopropyl biguanide, polymeric quaternary ammonium salts (such as polyquaternium-1, polyquaternium-2, poly-quaternium-4, polyquaternium-5, polyquaternium-6, polyquaternium-7, polyquaternium-8, polyquaternium-9, poly-quaternium-10, polyquaternium-11, polyquaternium-12, polyquaternium-13, polyquaternium-14, and polyquaternium-15), polyvinyl imidazolinium acetate, potassium polyacrylate, sodium polyacrylate, metal salts of PVM/MA copolymers, (e.g., Li, K, Na, Ru, Ce salts), PVP/eicosene copolymers, PVP/ethyl methacrylate/methacrylic acid copolymer, PVP/hexadecene copolymer, PVP/VA copolymer, PVP/vinyl acetate/itaconic acid copolymer, sodium acrylate/vinyl alcohol copolymers, sodium $C_4$–$C_{12}$ and other metal salts of olefin/maleic acid copolymers, sodium polymethacrylate, sodium polystyrene sulfonate, sodium styrene/acrylate/PEG-10 dimaleate copolymer, water-soluble esters and ethers of cellulose, sodium styrene/PEG-10 maleate/nonoxynol-10 maleate/acrylate copolymer, starch/acrylate/acrylamide copolymers, styrene/acrylamide copolymer, styrene/acrylate/ammonium methacrylate copolymer, styrene/maleic anhydride copolymer, styrene/PVO copolymer, sucrose benzoate/sucrose acetate isobutyrate/butyl benzyl phthalate copolymer, sucrose benzoate/sucrose acetate isobutyrate/butyl benzylphthalate/methyl methacrylate copolymer, urea/-formaldehyde prepolymers, urea/melamine/formaldehyde prepolymers, vinyl acetate/crotonic acid copolymers, vinyl alcohol copolymers, and mixtures thereof. Other water-soluble polymeric polyols and polyhydric alcohols, such as polysaccharides, also are suitable as polymer intercalants.

After contact between the layered material and water or the aqueous solution of intercalant polymer and/or water-miscible organic solvent, the resulting composition typically is a paste. An intercalant pesticide, either neat or in solution, then is added to the paste. The water and intercalant polymer activated the layered material such that the intercalant pesticide now intercalates between surfaces of the layered material. The pesticide is added as a liquid or as a solid to the activated layered material, and the resulting mixture typically is extruded to facilitate intercalation of the intercalant pesticide. Alternatively, the layered material, water, optional polymer and organic solvent, and intercalant pesticide all can be admixed, then extruded.

The amount of intercalant pesticide intercalated into the activated layered material varies substantially between about 0.01% and about 40%, and preferably between about 0.1% and 30%, based on the dry weight of the layered silicate material. The amount of intercalated pesticide generally is an amount sufficient for the pesticide to perform its intended function. However, high percentages of pesticide can be intercalated to provide a concentrated intercalated pesticide that is subsequently diluted with a liquid or solid carrier to provide a pesticide composition. The amount of intercalant pesticide intercalated into the layered material, therefore, can be substantially greater than the maximum of about 10% by weight pesticide applied to calcined clays.

In preferred embodiments of the invention, the amount of intercalant pesticides employed, with respect to the dry weight of layered material being intercalated, ranges from about 0.1 grams of intercalant pesticide:100 grams of layered material (dry basis), preferably at least about 1 gram of intercalant pesticide:100 grams of layered material to about 40 grams intercalant pesticide:100 grams of layered material. More preferred amounts are from about 5 grams intercalant pesticide/100 grams of layered material to about 30 grams intercalant pesticide/100 grams of layered material (dry basis). To achieve sufficient intercalation for exfoliation, the layered material/intercalant pesticide blend contains at least about 8% by weight, and preferably at least about 10%, by weight intercalant pesticide, based on the dry weight of the layered material.

The intercalant pesticides are introduced into (i.e., sorbed within) the interlayer spaces of the layered material in one of two ways. In a preferred method, the intercalant pesticide is dissolved in a solvent, and the intercalant pesticide solution is admixed with the layered material either before or after the layered material has been activated by contact with water or an aqueous solution of an intercalant polymer and/or water-miscible organic solvent. In an alternative method, the pesticide is added in a neat form to the activated layered material. The resulting mixture is extruded or pug milled to form an intercalated compo-sition comprising the activated layered material and an intercalant pesticide. The resulting mixture typically is a paste that, after pesticide intercalation, is dried, then pelletized to form a pesticide composition.

The intercalant pesticide carrier (i.e., water, an organic solvent, or a mixture thereof) can be added by first solubilizing or dispersing the intercalant pesticide in the carrier, or a dry intercalant pesticide and relatively dry phyllosilicate (preferably containing at least about 4% by weight water) can be blended and the intercalating carrier added to the blend, or to the phyllosilicate prior to adding the dry intercalant pesticide. In every case, it has been found that surprising sorption and complexing of intercalant pesticide between platelets is achieved at relatively low loadings of intercalating carrier, especially water, e.g., at least about 4% by weight water, based on the dry weight of the phyllosilicate. When intercalating the phyllosilicate in slurry form, the amount of water can vary from a preferred minimum of at least about 30% by weight water, with no upper limit to the amount of water in the intercalating composition (the phyllosilicate intercalate is easily separated from the intercalating composition).

Alternatively, the intercalating carrier can be added directly to the phyllosilicate prior to adding the intercalant pesticide, either dry or in solution. Sorption of the intercalant pesticide molecules can be performed by exposing the layered material to dry or liquid intercalant pesticides in the intercalating composition containing at least about 0.01%, preferably at least about 0.1%, more preferably at least about 1%, intercalant pesticide, based on the dry weight of the layered material. Sorption can be aided by exposure of the intercalating composition to heat, pressure, ultrasonic cavitation, or microwaves.

In accordance with another method of intercalating the intercalant pesticide between the platelets of the layered material, and optionally exfoliating the intercalate, the layered material, containing at least about 4%, and preferably about 10% to about 15%, by weight water, is blended with an intercalant pesticide in a ratio sufficient to provide at least about 8% by weight, preferably at least about 10% by weight intercalant pesticide, based on the dry weight of the layered material. The blend then preferably is extruded for faster intercalation of the intercalant pesticide with the layered material.

An intercalant pesticide having a polar moiety has an affinity for the phyllosilicate so that it is sorbed between, and is maintained associated with the surfaces of the silicate platelets, in the interlayer spaces, and after exfoliation. Pesticides lacking a polar moiety can be intercalated into a layered material that previously has been activated with water and a water-soluble polymer.

In accordance with the present invention, the intercalant pesticide preferably includes a polar moiety, like a carbonyl functionality, to be sufficiently bound, as theorized herein, by a mechanism selected from the group consisting of ionic complexing, electrostatic complexing, chelation, hydrogen bonding, dipole/dipole interaction, Van Der Waals forces, and any combination thereof. Such bonding, via the metal cations of the phyllosilicate sharing electrons with electronegative atoms of a polar moiety of one intercalant pesticide molecule or of two adjacent intercalant pesticide molecules, to an inner surface of the phyllosilicate platelets provides adherence between the polar moiety and the platelet inner surfaces of the layered material. Such intercalant pesticides have sufficient affinity for the phyllosilicate platelets to maintain sufficient interlayer spacing for exfoliation, without the need for coupling agents or spacing agents, such as the onium ion or silane coupling agents disclosed in the above-mentioned prior art. In pesticides lacking a polar moiety, the water-soluble polymer separates the platelets of the layered material a sufficient amount to allow the pesticides to intercalate between adjacent layers. The pesticide, either containing or lacking a polar moiety, displaces water and the water-soluble polymer from the space between adjacent layers of the layered material.

Figure 3:
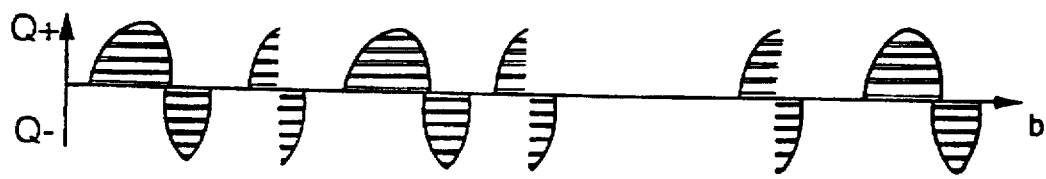
FIG. 3 is a schematic representation of the charge distribution on the surfaces of sodium montmorillonite clay platelets showing the distribution of positive and negative charges on the clay platelet surfaces as a result of the natural disposition of the Na, Mg, Al, Si, and O atoms of the clay shown in FIGS. 1 and 2.

As shown in FIGS. 1–3, the disposition of surface $Na^+$ ions with respect to the disposition of O, Mg, Si, and Al atoms, and the natural clay substitution of $Mg^{+2}$ cations for $Al^{+3}$ cations, leaving a net negative charge at the sites of substitution, results in a clay surface charge distribution as shown in FIG. 3. This alternating positive to negative surface charge over spans of the clay platelets surfaces, and on the clay platelet surfaces in the interlayer spacing, provide for excellent dipole-dipole attraction of pesticide molecules having a polar moiety for intercalation of the clay, and, after optional exfoliation, for bonding of such polar pesticide molecules on the platelet surfaces.

In accordance with an important feature of the present invention, the intercalated phyllosilicate can be manufactured in a concentrated form, e.g., up to 40%, preferably 1–30%, intercalant pesticide, by weight, and 10–90%, preferably 20–80%, intercalated phyllosilicate, by weight, and can be dispersed in an organic solvent and exfoliated, before or after addition to the solvent, to a desired platelet loading.

Pesticides useful in the present invention include insecticides, herbicides, acaricides, growth regulators, rodenticides, defoliants, fungicides, larvacides, nematocides, repellents, and other compounds capable of repelling, mitigating, or destroying undesirable and objectionable plants and animals. Preferred pesticides are organic compounds having at least one polar moiety. Polarity of the moiety results from two adjacent atoms that are covalently bonded, wherein a first atom having a low electronegativity is bonded to a second atom having a higher electronegativity. The difference in electronegativity between the two atoms (e.g., preferably at least about 0.5 electronegativity units) creates a charge differential between the first and second atoms, i.e., polarity. The first atom of lower electronegativity generally has an electronegativity of at least 2, the second atom of higher electronegativity has an electronegativity preferably at least 0.5 electronegativity units greater than the first atom, and typically is an atom such as oxygen, sulfur, or nitrogen.

The polar moiety of the organic pesticide compound often is a carbonyl moiety, such as in a carboxylic acid or salt thereof, an ester, an amide, an anhydride, a ketone, or an aldehyde. However, the polar moiety also can be cyano, nitro, thiocarbamate, amino, carbamic, phosphate, thiophosphate, sulfoxide, carboximide, urea, sulfone, phosphorothioate, phosphorodithioate, thiourea, dithiocarbamate, phosphoramidodi-thioate, methylsulfonyl, phosphonate, sulfamide, phosphoramide, sulfonate, dithiocarbonate, hydroxyl, sulfate, sulfinate, sulfamate, or phosphinate moieties, for example. The polar moiety also can be other moieties containing a combination of sulfur and oxygen atoms, or a combination of phosphorus and oxygen atoms.

Organic pesticide compounds containing one or more polar moieties are particularly suitable for use as intercalant pesticides in accordance with the present invention. However, pesticides lacking a polar group also can be used in the intercalant pesticide when an intercalant polymer is used to activate the layered material. The following are nonlimiting examples of pesticides useful in the present invention. The lists are intended to set forth examples of useful pesticides and are not intended to limit the pesticides that can be used in the present invention.

FUNGICIDES

Allyl alcohol, anilazine, triadimenol, benomyl, benquinox, bunema, captafol, captan, carbendazim, carboxin, chinosol, chloroneb, chlorothalonil, cycloheximide, dazomet, dicloran, dichlofluanid, dichlone, dimethirimol, dinocap, manzeb, dithianon, dodemorph, dodine, drazoxolon, edinfenphos, fenaminosulf, fenapanil, fentiazon, ferbam, folpet, fongarid, guazatine, hymexazol, iprodione, kasugamycin, maneb, MEMC, methylthiophenate, metiram, nabam, neo-asozin, o-phenylphenol, PMA, oxycarboxin, parinol, PCNB, phosethyl, piperalin, polyoxin, procymidone, propineb, propazine, propionic acid, prothiocarb, pyracarbolid, pyrazophos, thiabendazole, thiophanate, thiram, tolylfluanid, triadimefon, tridemorph, triforine, triphenyltin acetate, validamycin A, vinclozolin, vondozeb, zineb, chloranil, ziram, 8-quinolinol, CDEC, metam, glyodin, 2,6-bis[dimethylaminomethyl]cyclohexanone, hexachloroacetone, bromoacetyl bromide, picloram, benalaxyl, blasticidin S, bupirimate, buthiobate, chinomethionate, chlozolinate, cymoxanil, cyproconazole, dithianon, ethirimol, etridazole, fenarimol, fenpiclonil, fenpropidin, fenpropimorph, fentin, flusilazole, flutriafol, flutolanl, fuberidazole, furalaxyl, imazalil, imibenconazole, iprobenphos, isoprothiolane, mancozeb, mepronil, methfuroxam, metsulfovax, myclobutanil, nuarimol, ofurace, oxadixyl, polyoxin B, polyoxin D, prochloraz, procymidone, propiconazole, pyroquilon, quintozene, tebucanazole, tetraconazole, triarimol, tricyclazole, triforine, and mixtures thereof, and in mixture with other pesticides. Salts and esters of these fungicides also can be used as the pesticide.

HERBICIDES

Acifluorfen, alachlor, alanap, alloxydim, ametryn, amitrol, asulam, atrazine, azide, barban, benazolin, benefin, bensulide, bentazone, benthiocarb, benzoylprop, benzthiazuron, bifenox, acetochlor, acrolein, benazolin, buthidazole, allidochlor, bromacil, bromofenoxin, bromoxynil, butachlor, butralin, buturon, butylate, chlometoxynil, chloramben, chlorbromuron, chlorfenprop, chloridazon, chlorotoluron, chloroxuron, chlorpropham, chlorthiamid, CNP, crotoxyphos, cycloate, cyprazine, 2,4-D, dalapon, 2,4-DB, DCPA, 2,4-DEP, desmedipham, 2,4-DP, desmetryn, diallate, dicamba, dichlobenil, dichlorprop, diethatyl, difenoxuron, diclofop, dimexano, dinitramine, dinoseb, dinoterb, diphenamid, dipropetryn, diquat, diuron, endothall, erbon, ethofumesate, fenac, fenuron, flamprop, fluchloralin, EPTC, pentachlorophenol, fluometuron, fluorodifen, flurecol, glyphosate, glyphosine, hexazinone, ioxynil, isopropalin, isoproturon, karbutilate, lenacil, linuron, MCPA, MCPB, mecoprop, medinoterb, methazole, methoprotryne, metobromuron, metolachlor, metoxuron, metribuzin, molinate, monalide, monlinuron, monuron, naptalam, neburon, nitralin, nitrofen, norea, norflurazon, oryzalin, oxadiazon, paraquat, pebulate, penoxalin, perfluidone, phenisopham, phenmedipham, picloram, procyazine, profluralin, prometon, prometryn, pronamide, propachlor, propanil, propazine, propham, secbumeton, siduron, silvex, simazine, swep, 2,4,5-T, 2,3,6-TBA, tebuthiuron, terbacil, terbumeton, terbuthylazine, terbutol, terbutryn, tetrafluoron, triallate, trietazine, trifluralin, vernolate, 1-naphthaleneacetic acid, N-m-tolylphthalamic acid, ethyl-1-naphthalene acetate, chloroacetic acid, trichloroacetic acid, p-chloromandelic acid, dimethylamino-2,3,5-triiodobenzoate, 2-naphthoxyacetic acid, phenoxyacetic acid, 2-phenoxypropionic acid, o-chlorophenoxy acetic acid, p-chlorophenoxy acetic acid, MCPA, silvex, MCPB, p-bromophenoxy acetic acid, dimethylamino-4[2,4-dichlorophenoxy]butryate, 3-indolebutyric acid, 3-indoleacetic acid, 3-indolepropionic acid, gibberellic acid, N,N-dimethylsuccinamic acid, 2-furanacrylic acid, endothal, 1-naphthaleneacetamide, CDAA, N-methyl-N-1-naphthylacetamide, N-1-naphthyl acetamide, 2-[3-chlorophenoxy]propionamide, noruron, linuron, siduron, metobromuron, terbacil, chloroxuron, aminotriazole, cyanazine, chlorflurenol, chlorsulfuron, cyanazine, cyometrinil, 3,6-dichloropicolinic acid, dichlofop, difenzoquat, diphenamid, ethaflualin, ethepon, flurazole, flurenol, fluridone, fosamine, isouron, mefluidide, 1,8-naphthalic anhydride, napropamide, pyrazon, thoibencarb, anilazine, diphenatrile, N-[2,4-dichlorophenoxy)acetyl-DL-methionine, daminozide, pyrazon, ethoxyquin, propham, EPTC, S-carboxymethyl-N,N-dimethyldicarbamate, phosphan, merphos, ethephon, tricamba, amiben, MCPD, glufosinate, indole-3-butyric acid, β-naphthoxyacetic acid, triclopyr, 9-undecylenic acid, oxyflurofen, dinitrocresol, flurtamone, diflufenican, difunon, fomesafen, clethodim, sethoxydim, haloxyfop, tralkoxydim, fenoxaprop, fluazifop, phaseolotoxin, rhizobitoxine, barban, ethephon, tetcyclacis, mepiquat chloride, ancymidol, uniconzaole, paclobutrazol, diquatop, pendimethalin, karbutilate, asulam, clopyralid, fluroxypyr, chlorimuron, chlorsulfuron, metsulfuron, buthidazole, imazamethabenz, imazapyr, imazaquin, imazethapry, isoxaben, cinmethylin, ethofumesate, and mixtures thereof, and in mixture with other pesticides. Several of the herbicides listed above are acid compounds. In addition to the acid form of such herbicides, esters (e.g., esters derived from $C_1$–$C_{12}$ alcohols) and salts (e.g., amine, potassium, lithium, and sodium salts) of these herbicides can be used as the intercalant pesticide.

INSECTICIDES AND ACARICIDES

Acephate, aldicarb, aldoxycarb, aldrin, d-trans allethrin, allyxycarb, aminocarb, amitraz, azinphos, azinphos, azocyclotin, azothoate, bendiocarb, benzomate, binapacryl, bomyl, BPMC, bromophos, bromophos-ethyl, bromopropylate, butacarb, butocarboxim, chlordane, chlordecone, heptachlor, lindane, methoxychlor, toxaphene, butoxicarboxim, carbaryl, carbofuran, carbophenothion, cartap, chloridimeform, chlorfenethol, chlorfenvinphos, chlormephos, chlorobenzilate, chloropropylate, chlorphoxim, chlorpyrifos, chlorthiophos, coumaphos, CPMC, crufomate, cryolite, cyanofenphos, cyanophos, cyhexatin, cypermethrin, cythioate, DDT, DDVP, demeton, demeton-S-methyl, dialifor, diazinon, dicofol, dicrotophos, dieldrin, dienochlor, diflubenzuron, dimefox, dimethoate, dimethrin, dinobuton, dioxacarb, dioxathion, disulfoton, DNOC, d-phenothrin, endosulfan, enfrin, EPN, ethiofencarb, ethion, ethoate, ethoprop, etrimfos, famphur, fenbutatin-oxide, fenitrothion, fenson, fensulfothion, fenthion, fenvalerate, fonofos, formetanate hydrochloride, formothion, fosthietan, hydroprene, isofenphos, isoxathion, isothioate, malathion, mecarbam, mecarphon, menazon, meobal, mephosfolan, mercaptodimethur, methamidophos, methidathion, methomyl, methoprene, MIPC, mirex, monocrotophos, MTMC, naled, nicotine, omethoate, oxamyl, oxydemeton-methyl, oxydisulfoton, parathion, permethrin, phenthoate, phorate, phosalone, phosmet, phosphamidon, phoxim, pirimicarb, pirimiphos, plifenate, profenofos, promecarb, propargite, propetamphos, propoxur, prothiophos, prothoate, quinalphos, resmethrin, ronnel, ryania, salithion, schradan, sulfotepp, sulprofos, temephos, TEPP, terbufos, tetrachlorvinphos, tetradifon, tetramethrin, tetrasul, thiocyclam-hydrogenoxalate, thiometon, thioquinox, triazophos, trichloronate, trichloron, vamidothion, melvinphos, TEPP, trichlorofon, O,O-dimethyl phosphorochloriodothioate, methyl parathion, demeton O, dicapthon, O,O-diethylphosphorochloridothioate, propham, matacil, m[1-ethylpropyl]phenylmethylcarbamate & m[1-ethylpropyl] phenylmethylcarbamate (mixture), pyrethrum, benzyl thiocyanate, rotenone, eugenol, and mixtures thereof, and in mixture with other pesticides. Salts and esters of these insecticides also can be used as the intercalant pesticide.

MISCELLANEOUS PESTICIDES

Aminozide, ancymidol, anthraquinone, brodifacoum, bromadiolone, butoxy polypropylene glycol, carbon tetrachloride, chloflurecol-methyl ester, chlormequat chloride, chlorophacinone, chloropicrin, chlorphonium, chlonitralid, coumachlor, coumafuryl, crimidine, cyoxmetril, deet, diazacosterol hydrochloride, dibutyl phthalate, ethyl hexanediol, dichlofenthion, difenacoum, dikegulac sodium, diphenylamine, ethephone, fenamiphos, fluoroacetamide, glyoxime, gossyplure, heliotropin acetal, kinoprene, maleic hydrazine, mepiquat-chloride, metaldehyde, metamsodium, naphthalene acetamide, 1-naphthaleneacetic acid, nitrapyrin, pyriminal, scillirosid, sesamex, sulfoxide, trifenmorph, triprene, warfarin, and mixtures thereof, and in mixture with other pesticides. Salts and esters of these pesticides also can be used as the intercalant pesticide.

In accordance with another embodiment of the present invention, the intercalates can be exfoliated, then used as a pesticide or a component in a pesticide composition, or dispersed in a solvent or carrier to provide a viscous or thixotropic pesticide composition. In either case, the pesticide composition can include various optional components and additives commonly employed in pesticide compositions. Such optional components include fillers, wetting agents, synergists, colorants, dispersants, emulsifiers, anti-caking agents, defoamers, dedusting agents, sequestering agents, coupling agents, water-softening agents, and the like. These optional components, and appropriate amounts, are well known to those skilled in the art.

The amount of intercalated and/or exfoliated layered material included in a liquid carrier or solvent to form viscous compositions or thixotropic suitable to deliver the carrier-dissolved or carrier-dispersed pesticide, can vary widely depending on the intended use and desired viscosity of the pesticide composition. For example, relatively high amounts of intercalate, i.e., about 10% to about 30% by weight of the total composition, are used to form solvent gels having extremely high viscosities, e.g., 5,000 to 5,000,000 centipoise (cps). Extremely high viscosities, however, also can be achieved with a relatively small concentration of intercalates and/or exfoliates thereof, e.g., 0.1% to 5% by weight, by adjusting the pH of the composition to about 0 to about 6 or about 10 to about 14 and/or by heating the composition above room temperature, e.g., in the range of about 25° C. to about 200° C., preferably about 75° C. to about 100° C.

In accordance with an important feature of the present invention, compositions of the present invention containing an intercalate and/or exfoliate, and a solvent or carrier, can be manufactured in a concentrated form, e.g., as a master gel having about 10 to about 90%, preferably about 20 to about 80%, intercalate and/or exfoliated platelets of layered material and about 10 to about 90%, preferably about 20 to about 80%, carrier or solvent. The master gel can be diluted and mixed with additional carrier or solvent to reduce the viscosity of the composition to a desired level, or to reduce the pesticide concentration to an efficacious and safe level for application.

Intercalate or platelet particle loadings in the solvent or carrier are within the range of about 0.01% to about 40% by weight, preferably about 0.05% to about 20%, more preferably about 0.5% to about 10% of the total weight of the composition to significantly increase the viscosity of the composition. In general, the amount of intercalate and/or platelet particles incorporated into the carrier or solvent is less than about 30% by weight of the total composition, and preferably from about 0.01% to about 20% by weight of the composition, more preferably from about 0.01% to about 10% by weight of the composition.

The intercalates, and/or exfoliates thereof, are mixed with a carrier or solvent to produce viscous compositions including one or more pesticide compounds, such as an insecticide, dissolved or dispersed in the carrier or solvent. In accordance with an important feature of the present invention, a wide variety of pesticide compounds can be incorporated into a stable composition of the present invention. Such active compositions include insecticides, herbicides, and fungicides that act upon contact with the insect, plant, or fungus to topically destroy the pest, or are absorbed or ingested by the pest to systemically destroy the pest.

In accordance with another important feature of the present invention, a second pesticide or an optional component can be solubilized in a composition of the present invention or can be homogeneously dispersed throughout the composition as an insoluble, particulate material. In either case, pesticide compositions of the present invention are resistant to composition separation and effectively apply the pesticide compound to the desired area of application. If required for stability, a surfactant can be included in the composition, such as any disclosed in Laughlin et al. U.S. Pat. No. 3,929,678, hereby incorporated by reference. In general, the pesticide compositions of the present invention demonstrate essentially no phase separation when the second pesticide compound and/or optional components are either solubilized or dispersed as an insoluble material in the compositions.

Therefore, in accordance with an important feature of the present invention, the stable intercalated pesticide composition can include any of the generally known pesticides as the second pesticide, often in the form of a finely divided solid. In general, the amount of the second pesticide compound in the composition can range from 0%, preferably about 0.01%, to about 40%, and preferably from 0.1% to about 30%, by weight of the total composition. The amount of surfactant can range from 0%, preferably about 0.01%, to about 15% by weight of the total composition.

An optional exfoliation of the intercalated layered material typically delaminates at least about 90% by weight of the intercalated material. Exfoliation provides a more viscous composition when the intercalated pesticide is homogeneously dispersed in a carrier or solvent. Some intercalates require a shear rate that is greater than about 10 $sec^{-1}$ for relatively thorough exfoliation. The upper limit for the shear rate is not critical. In preferred embodiments of the invention, when shear is employed for exfoliation, the shear rate is greater than about 10 $sec^{-1}$ to about 20,000 $sec^{-1}$, and in more preferred embodiments, the shear rate is about 100 $sec^{-1}$ to about 10,000 $sec^{-1}$. Such intercalates exfoliate naturally or by heating, or by applying pressure, e.g., 0.5 to 60 atmospheres above standard atmospheric pressure with or without heating.

When shear is employed for exfoliation, any known method for applying a shear to the intercalant/carrier composition can be used. The shearing action can be provided by any appropriate method, as for example by mechanical means, by thermal shock, by pressure alteration, or by ultrasound, all of which are known in the art. In particularly useful procedures, the composition is sheared by mechanical means in which the intercalate, with or without the carrier or solvent, is sheared by stirrers, Banbury®-type mixers, Brabender®-type mixers, injection molding machines, long continuous mixers, extruders, and similar mechanical means. Another procedure employs thermal shock in which shearing is achieved by alternatively raising or lowering the temperature of the composition causing thermal expansions and resulting in internal stresses which cause shear. In still other procedures, shear is achieved by sudden pressure changes in pressure alteration methods, by ultrasonic techniques in which cavitation or resonant vibrations cause portions of the composition to vibrate or to be excited at different phases and thus subjected to shear. These methods of shearing are merely representative of useful methods, and any method known in the art for shearing intercalates may be used.

Shearing can be achieved by introducing the activated layered material and intercalant pesticide, or mixture thereof, at one end of an extruder (single or double screw) and receiving the sheared material at the other end of the extruder. The temperature of the layered material/intercalant pesticide composition, the length of the extruder, residence time of the composition in the extruder and the design of the extruder (e.g., single screw, twin screw, number of flights per unit length, channel depth, flight clearance, mixing zone) are several variables which control the amount of shear to be applied for exfoliation. Alternatively, the layered material can be activated and intercalated by introducing the layered material, water, water-soluble polymer, and intercalant pesticide, or a mixture thereof, at one end of the extruder.

Exfoliation is sufficiently thorough to provide at least about 80%, preferably at least about 85%, more preferably at least about 90%, and most preferably at least about 95% by weight delamination of the layers to form individual platelet particles that can be substantially homogeneously dispersed in the carrier or solvent. As formed by this process, the platelet particles dispersed in the carrier or solvent have the thickness of the individual layers plus one to five monolayer thicknesses of intercalated pesticide, or small multiples less than about 10, preferably less than about 5 and more preferably less than about 3 of the layers, and still more preferably 1 or 2 layers. In the preferred embodiments of this invention, intercalation and delamination of every interlayer space is complete so that all or substantially all individual layers delaminate one from the other to form separate platelet particles for admixture with the carrier or solvent. In one embodiment, the compositions initially include all intercalated layered material, completely without exfoliation, to provide relatively low viscosities for transportation and pumping until it is desired to increase viscosity via exfoliation. In cases where intercalation between some layers is incomplete, those layers do not delaminate in the carrier or solvent, and form platelet particles comprising layers in a coplanar aggregate.

The effect of adding nanoscale, particulate dispersed platelet particles, derived from the intercalates, into an organic liquid carrier, typically is an increase in viscosity. Pesticide compositions comprising a solvent containing a desired loading of platelets obtained from exfoliation of the intercalates and are outstandingly suitable as commercial products. Such compositions are viscous liquids or gels that resist leaking from packages and are easy to collect if spilled. The compositions according to the invention also are easily dissolved, dispersed or emulsified in an appropriate solvent by pesticide applicators, who then can apply the correct dosage of pesticide to the desired surface. Some viscous or gelled pesticide compositions can be packaged in water-soluble packaging. Such compositions resist leakage from the package if the package is damaged. Accordingly, the pesticide applicator does not come in contact with the pesticide, and accidental spillage or leakage of the pesticide is essentially eliminated.

The following are specific clay:water-soluble polymer intercalate preparations to more particularly illustrate the activation of a layered material and are not to be construed as limitations thereon. These clay-polymer intercalates constitute one form of an activated clay, and can be used as a precursor to adding the intercalant pesticide. Alternatively, water alone or an aqueous solution of a water-miscible organic solvent is added to activate the clay prior to adding the intercalant pesticide. In another embodiment, the clay is activated in the presence of an intercalant pesticide.

Preparation of Clay-PVP Complexes

Materials:
  Clay-sodium montmorillonite;
  Intercalant polymer-PVP (molecular weights of 10,000 and 40,000).

To prepare clay (sodium montmorillonite)-PVP complexes (i.e., intercalates), three different processes were used for polymer intercalation to activate the clay:

1. Mixture of a 2% PVP/water solution with a 2% clay/water suspension in a ratio sufficient to provide a polymer concentration of at least about 8% by weight, preferably at least about 10% by weight, based on the dry weight of the clay.
2. Dry clay powder (about 8% by weight moisture) was gradually added to a 2% PVP/water solution in a ratio sufficient to provide a polymer concentration of at least about 8% by weight, preferably at least about 10% by weight, based on the dry weight of the clay.
3. Dry PVP was mixed with dry clay, and the resulting mixture was hydrated with about 25 to about 50%, preferably about 35% to about 40% by weight water, based on the dry weight of the clay, and then extruded.

Mixtures 1 and 2 were agitated at room temperature for 4 hours. The clay:PVP weight ratio was varied from 90:10 to 20:80.

Figure 4:
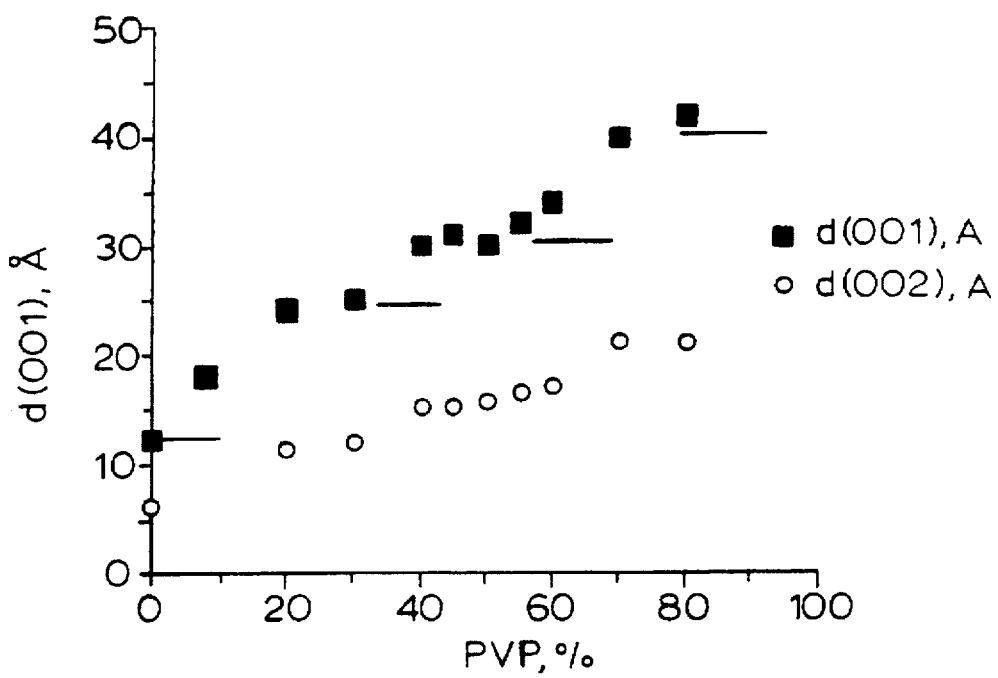
FIG. 4 is a graph plotting interlayer space for polyvinylpyrrolidone (PVP):smectite clay complexes (intercalates) showing d(001) and d(002) spacings, in Angstroms (Å), versus percentage of PVP sorbed, based on the dry weight of the smectite clay.
Figure 6:
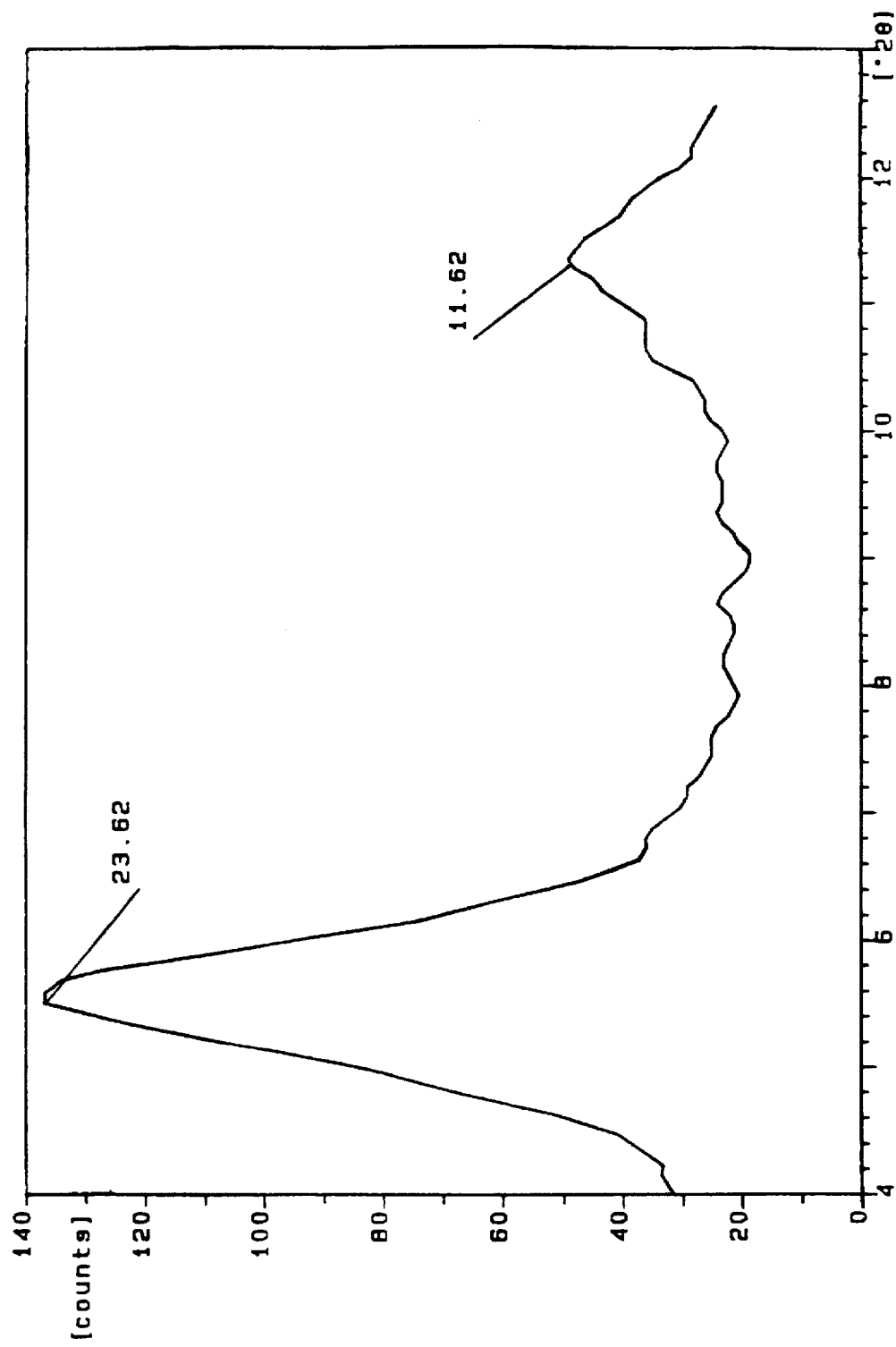
FIG. 6 is an x-ray diffraction pattern for a complex of PVP (weight average molecular weight of 10,000):sodium montmorillonite clay, in Angstroms, at a weight ratio of PVP:clay of 20:80.

The examples in Table 1 show that each method of preparation yielded a clay-PVP complex (intercalate), and that intercalation results do not depend upon a particular method of preparation (1, 2, or 3) or upon the molecular weight of the intercalant polymer (PVP), but do depend upon the ratio of clay:PVP. In Table 1, data from x-ray diffraction patterns for clay-PVP complexes with different ratios of components are summarized. The plot of this data is illustrated in FIG. 4. From this data (Table 1, FIG. 4) the stepwise character of intercalation while the polymer is being sorbed in the interlayer space between adjacent platelets of the montmorillonite clay is seen. There are increasing d(001) values from 12 Å (for clay with no sorbed PVP, i.e., FIG. 11) to a 24–25 Å spacing between adjacent clay platelets with sorption of 20–30% PVP. FIG. 6 illustrates a d(001) value of 23.62 Å for a PVP:clay weight ratio of 20:80.

Figure 10:
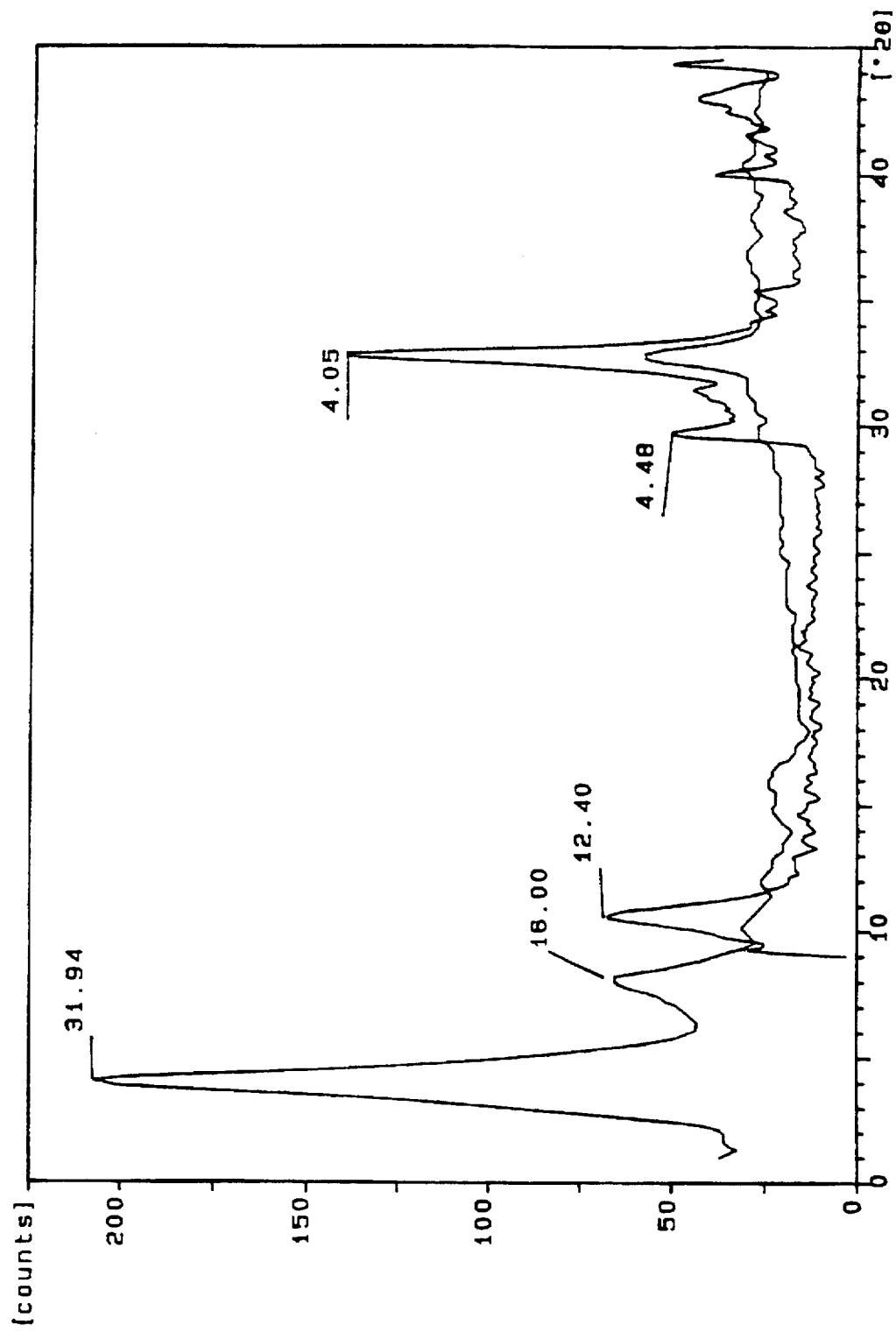
FIG. 10 is an x-ray diffraction pattern for a complex of PVP:sodium montmorillonite clay, in Angstroms, at a weight ratio of PVP:clay of 50:50 (upper pattern), and an x-ray diffraction pattern for about 100% sodium montmorillonite clay having a crystobalite impurity (lower pattern)
Figure 12:
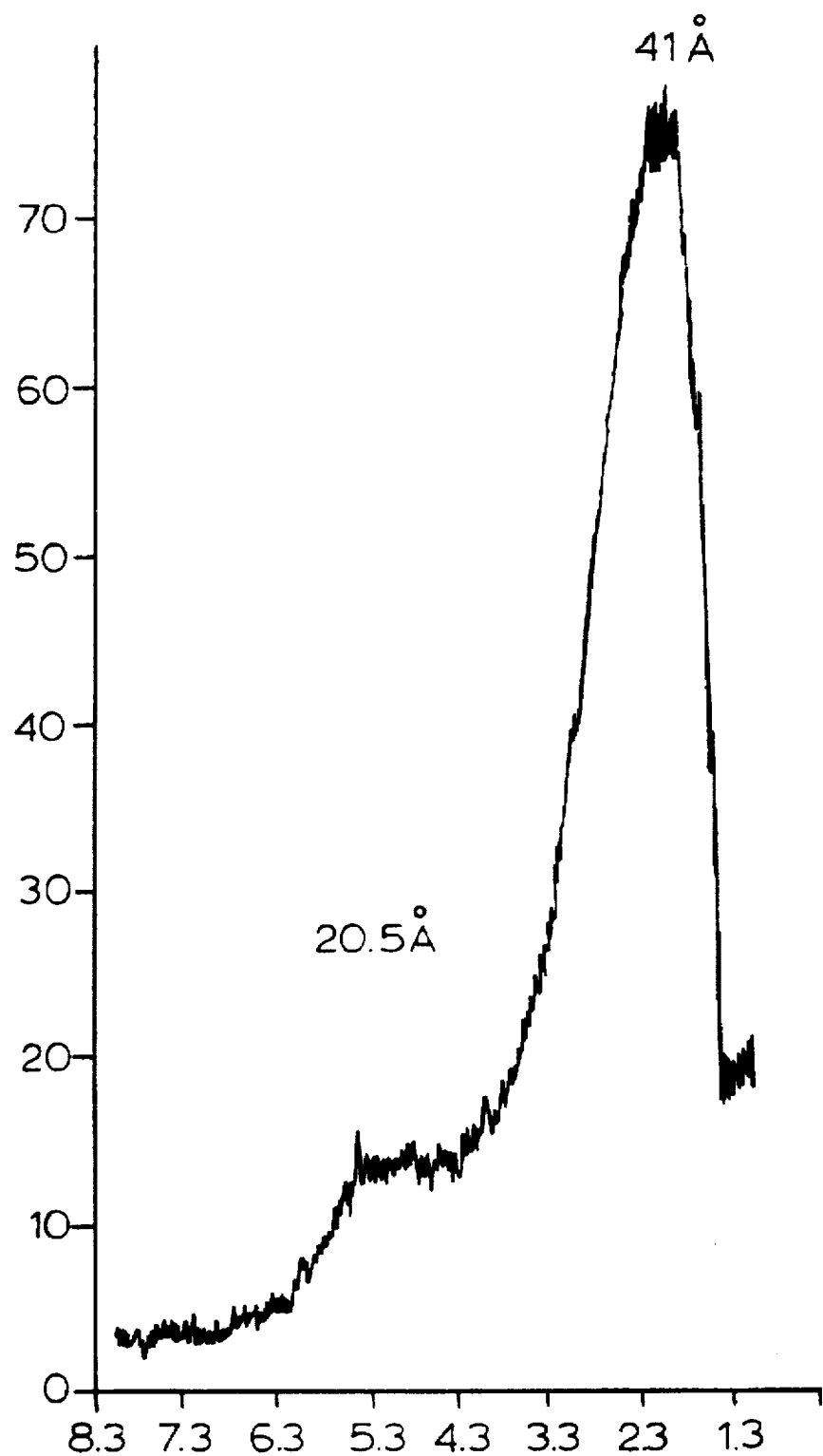
FIG. 12 is a portion of an x-ray diffraction pattern for PVP:sodium montmorillonite clay, in Angstroms, at a PVP:clay ratio of 80:20, showing a PVP:clay complex peak or d(001) spacing of about 41 Å.

The next step to 30–32 Å spacing occurs when the sorbed PVP content is increased to 40–60%. FIG. 10 illustrates a d(001) value of 31.94 Å for a PVP:clay weight ratio of 50:50. Further increasing the sorbed PVP content to 70–80% increases the d(001) values to 40–42 Å. FIG. 12 illustrates a d(001) value of 41 Å for a PVP:clay weight ratio of 80:20. There are d(002) values together with d(001) values in x-ray diffraction patterns of all intercalates obtained (Table 1, FIG. 4). This indicates the regularity of clay-PVP intercalate structures.

TABLE 1

| | PVP, %[1] | d(001), Å | d(002), Å |
|---|---|---|---|
| 1 | 0.0 | 12.4 | 6.2 |
| 2 | 10.0 | 17.5 | 8.6 |
| 3 | 20.0 | 24.0 | 11.4 |
| 4 | 30.0 | 25.0 | 12.0 |
| 5 | 40.0 | 30.0 | 15.2 |
| 6 | 45.0 | 31.0 | 15.2 |
| 7 | 50.0 | 30.0 | 15.5 |
| 8 | 55.0 | 32.0 | 16.5 |
| 9 | 60.0 | 34.0 | 17.0 |

TABLE 1-continued

| | PVP, %[1] | d(001), Å | d(002), Å |
|---|---|---|---|
| 10 | 70.0 | 40.0 | 21.0 |
| 11 | 80.0 | 42.0 | 21.0 |

[1]Percent by weight, based on the dry weight of the clay plus polymer.

Preparation of Clay-PVA Complexes

Materials:
  Clay-sodium montmorillonite;
  Intercalant polymer-PVA (degree of hydrolysis 75–99%, molecular weight 10,000).

To prepare clay (sodium montmorillonite)-PVA complexes (i.e., intercalates), three different processes were used for polymer intercalation to activate the clay:

1. Mixture of a 2% PVA/water solution with a 2% clay/water suspension in a ratio sufficient to provide a polymer concentration of at least about 8% by weight, preferably at least about 10% by weight, based on the dry weight of the clay.
2. Dry clay powder was gradually added to a 2% PVA/water solution in a ratio sufficient to provide a polymer concentration of at least about 8% by weight, preferably at least about 10% by weight, based on the weight of the clay.
3. Dry clay was moisturized with PVA/water solution to a moisture content of 25% to 80%, preferably about 35% to 40% water, and then extruded.

The mixtures 1 and 2 were agitated at room temperature for 4 hours.

The weight ratio clay:PVA was varied from 80:20 to 20:80.

Figure 5:
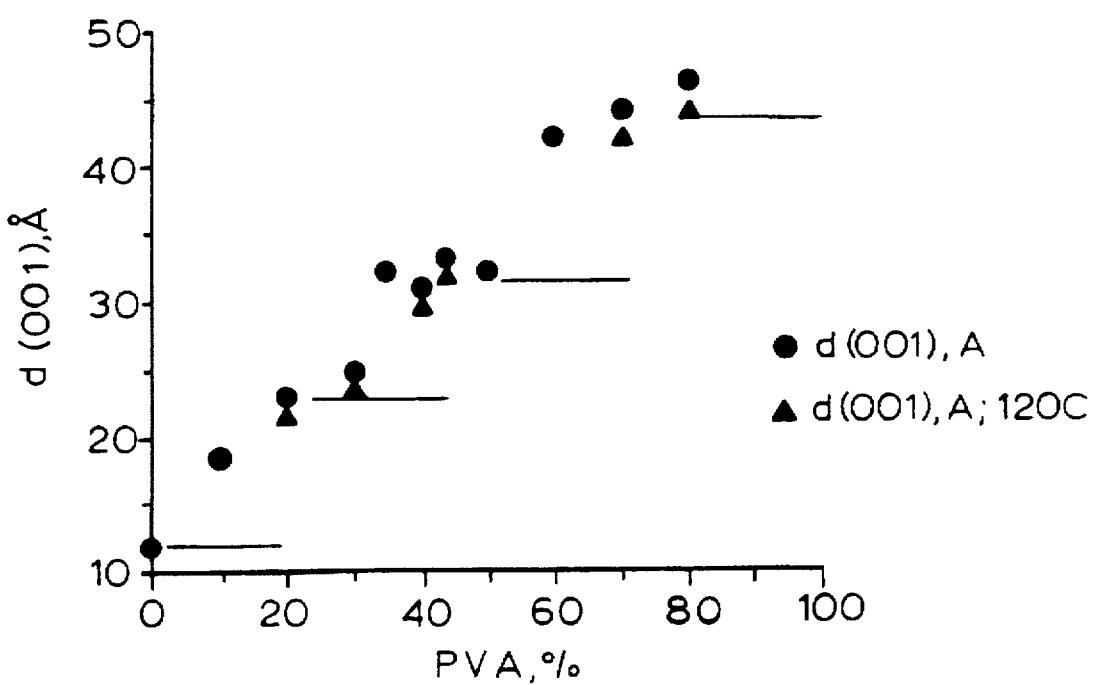
FIG. 5 is a graph plotting interlayer space for polyvinylalcohol (PVA):smectite clay complexes (intercalates) showing d(001) spacing, in Angstroms, between smectite clay platelets versus percentage of PVA sorbed, based on the dry weight of the smectite clay.
Figure 8:
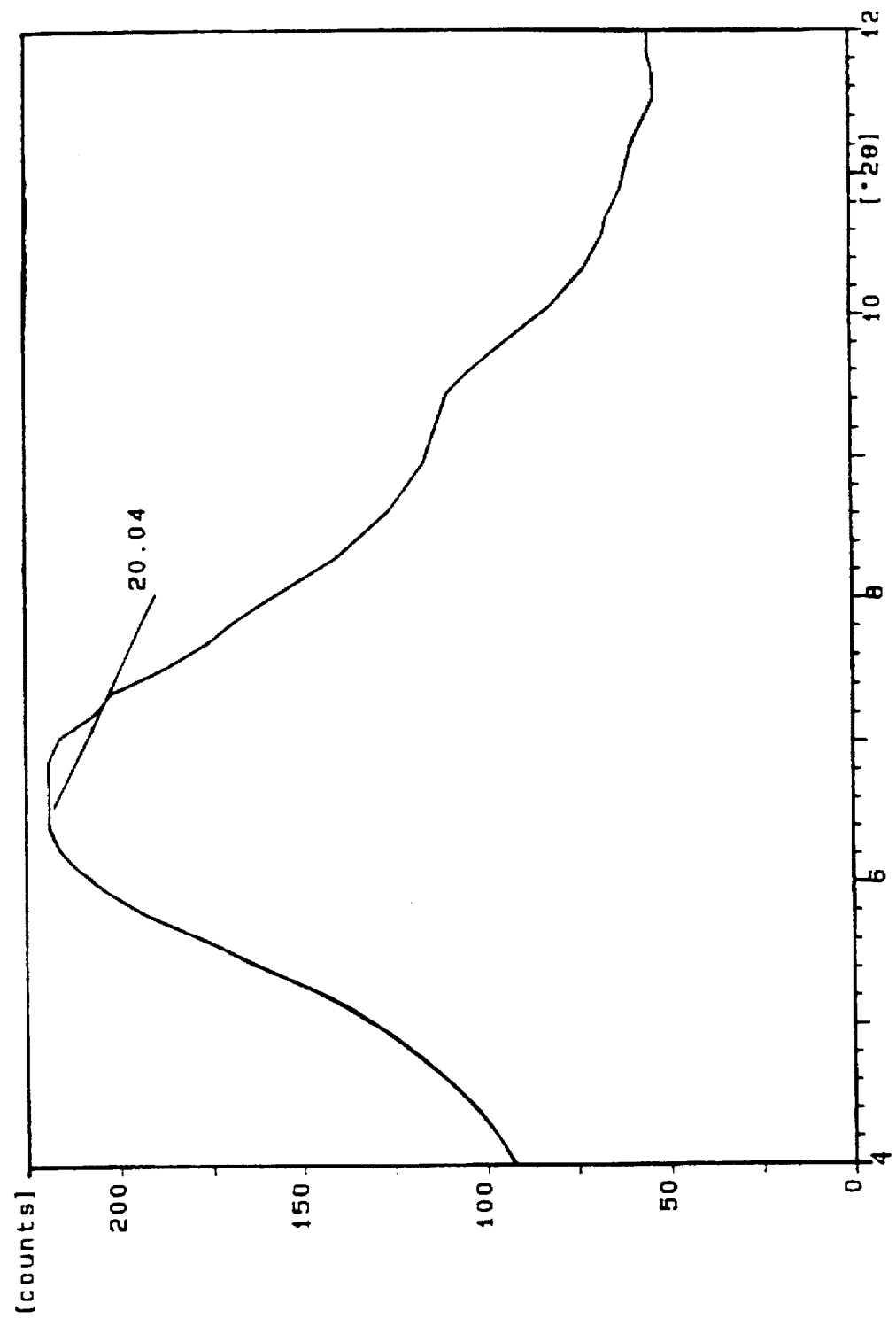
FIG. 8 is an x-ray diffraction pattern for a complex of PVA (weight average molecular weight of 15,000):sodium montmorillonite clay, in Angstroms, at a weight ratio of PVA:clay of 20:80.

Some of the intercalates were studied by x-ray diffraction. These examples show that all methods of preparation yielded the composite clay-PVA complexes (intercalates), and the results of the intercalation do not depend upon a particular method of preparation (1, 2, or 3), the molecular weight of the intercalant polymer (PVA), or the degree of hydrolysis, but do depend on the clay:PVA ratio. In Table 2 data from x-ray diffraction patterns for clay-PVA complexes with different ratios of components are summarized. A plot of this data is illustrated in FIG. 5. From this data (Table 2, FIG. 5), the stepwise character of increasing d(001) values from 12 Å (for clay with no sorbed PVA, i.e., FIG. 11) to 22–25 Å spacing between adjacent platelets with sorption of 20–30% PVA is illustrated. FIG. 8 illustrates a d(001) value of 20.04 Å for a PVA:clay weight ratio of 20:80. The next step to 30–33 Å occurs when the sorbed PVA content increases to 35–50%. A further increase of the sorbed PVA content to 60–80% increases the d(001) values to 40–45 Å.

Heating the clay-PVA intercalates at 120° C. for 4 hours did not significantly change the d(001) values (Table 2, FIG. 5). The change in d(001) value from 12.4 Å to 9.6 Å for the sample containing 0% PVA illustrates that water is expelled from the clay, the spacing between clay platelets is decreased.

TABLE 2

| PVA %[1] | d(001), Å | d(001), Å 120° C. |
|---|---|---|
| 1  | 0.0  | 12.4 | 9.6  |
| 2  | 10.0 | 17.0 | 16.8 |
| 3  | 20.0 | 23.0 | 22.0 |
| 4  | 30.0 | 25.0 | 24.0 |
| 5  | 35.0 | 32.0 | 32.0 |
| 6  | 40.0 | 31.0 | 30.0 |
| 7  | 45.0 | 33.0 | 32.0 |
| 8  | 50.0 | 32.0 | 32.0 |
| 9  | 60.0 | 42.0 | 42.0 |
| 10 | 70.0 | 44.0 | 42.0 |
| 11 | 80.0 | 45.0 | 44.0 |

[1]Percent by weight, based on the dry weight of the clay plus PVA.

Figure 7:
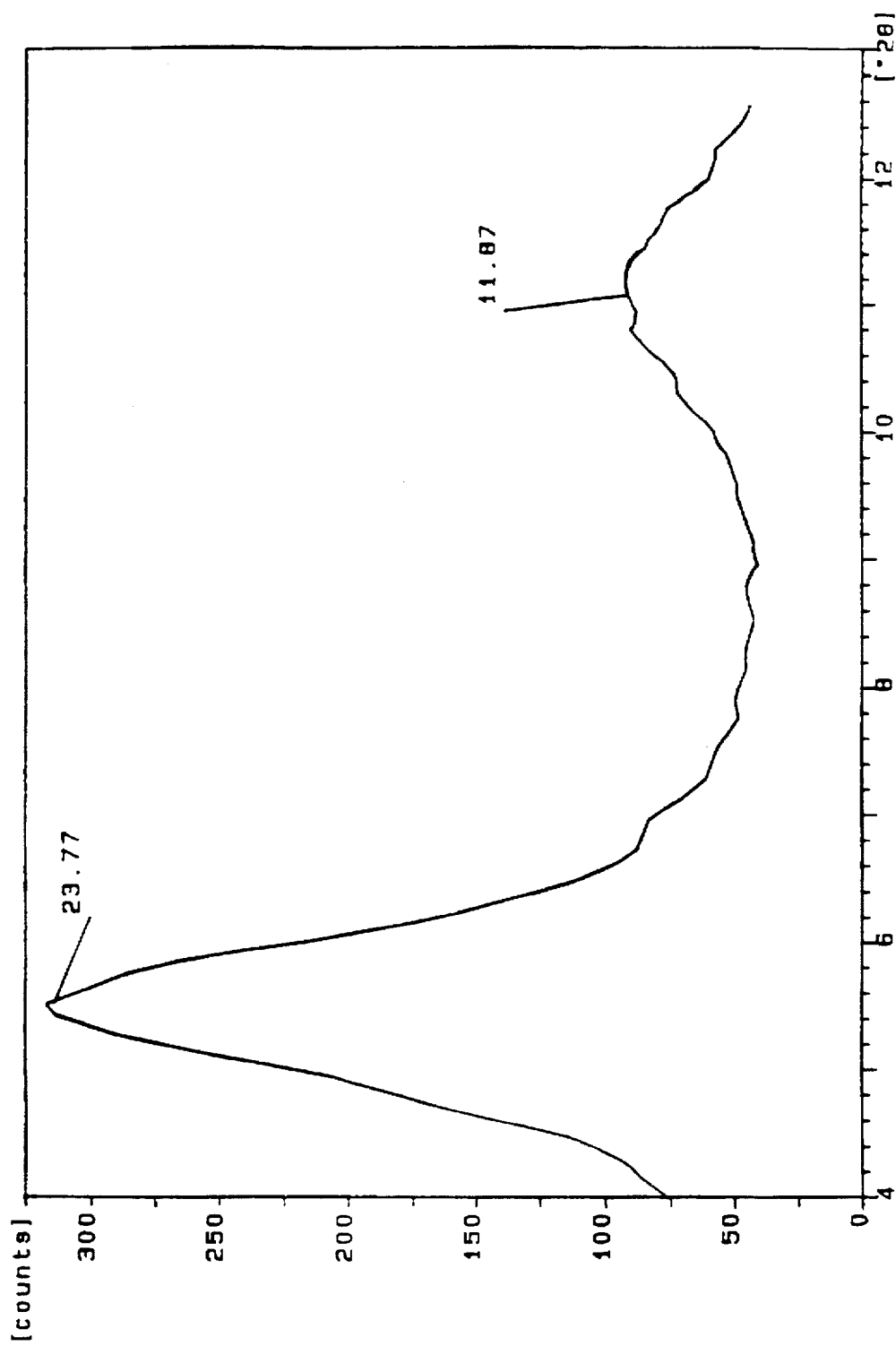
FIG. 7 is an x-ray diffraction pattern for a complex of PVP (weight average molecular weight of 40,000):sodium montmorillonite clay, in Angstroms, at a weight ratio of PVP:clay of 20:80.

Specifically, FIGS. 6 through 8 are x-ray diffraction patterns of blends of different water-soluble polymers with sodium bentonite clay. The patterns of FIGS. 6 and 7 are taken from clay intercalated with 20% by weight polyvinylpyrrolidone (weight average molecular weight 10,000 for FIG. 6; 40,000 for FIG. 7) and 80% by weight sodium bentonite clay. The blends were formed by mixing the PVP and clay from a solution of PVP and a 2% dispersion of sodium bentonite in a 1:4 ratio, respectively. As shown, the PVP:clay complexed since no d (001) smectite peak appears at about 12.4 Å (i.e., see FIG. 11 for untreated sodium bentonite clay). Similar results are shown for 20% polyvinyl alcohol, 80% sodium bentonite, as shown in FIG. 8, blended in the same way and in the same ratio. An x-ray diffraction pattern for sodium bentonite containing no additives is presented FIG. 11 for comparison.

Figure 9:
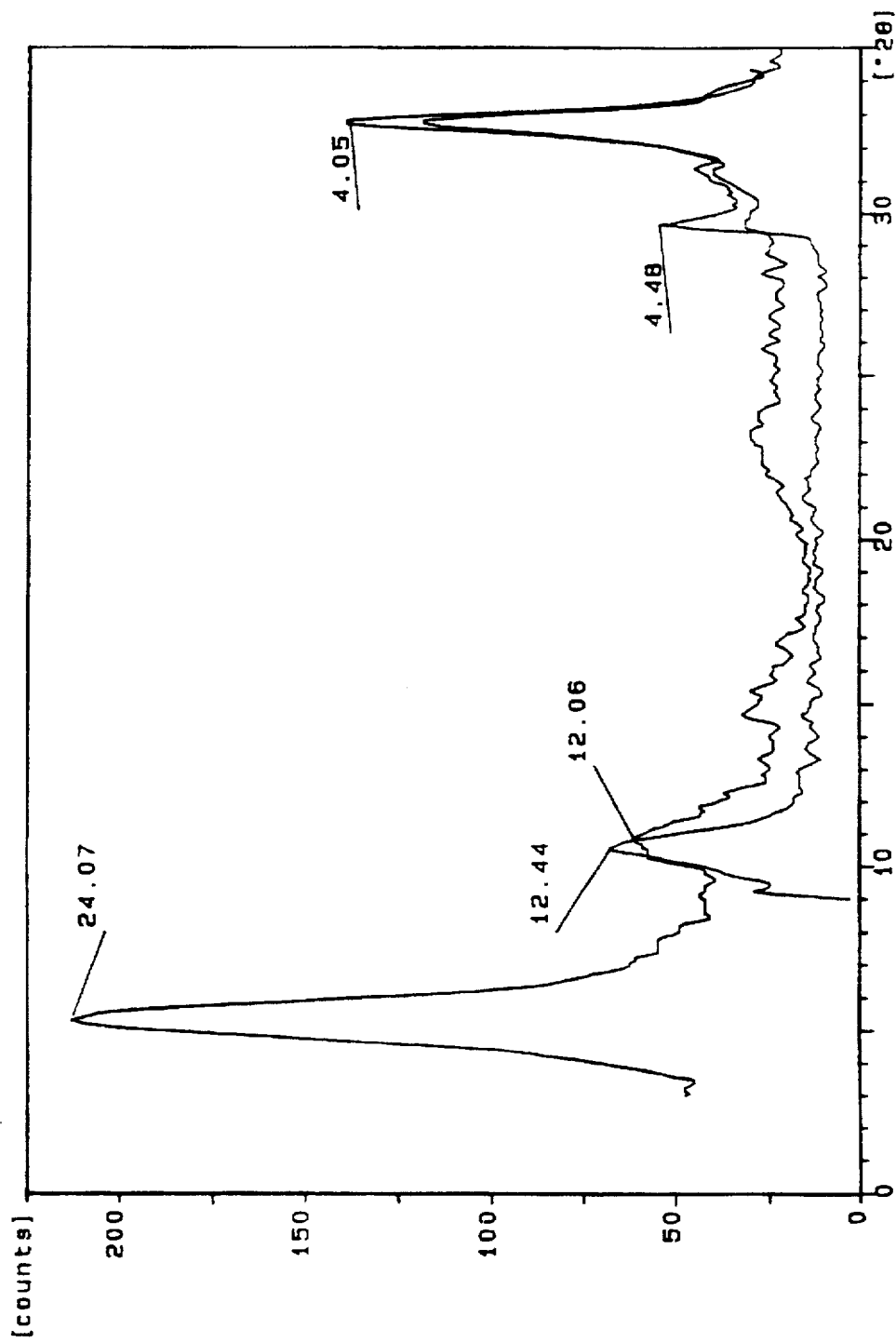
FIG. 9 is an x-ray diffraction pattern for a complex of PVP:sodium montmorillonite clay, in Angstroms, at a weight ratio of PVP:clay of 20:80 (upper pattern), and an x-ray diffraction pattern for about sodium montmorillonite clay having a crystobalite impurity (lower pattern)
Figure 11:
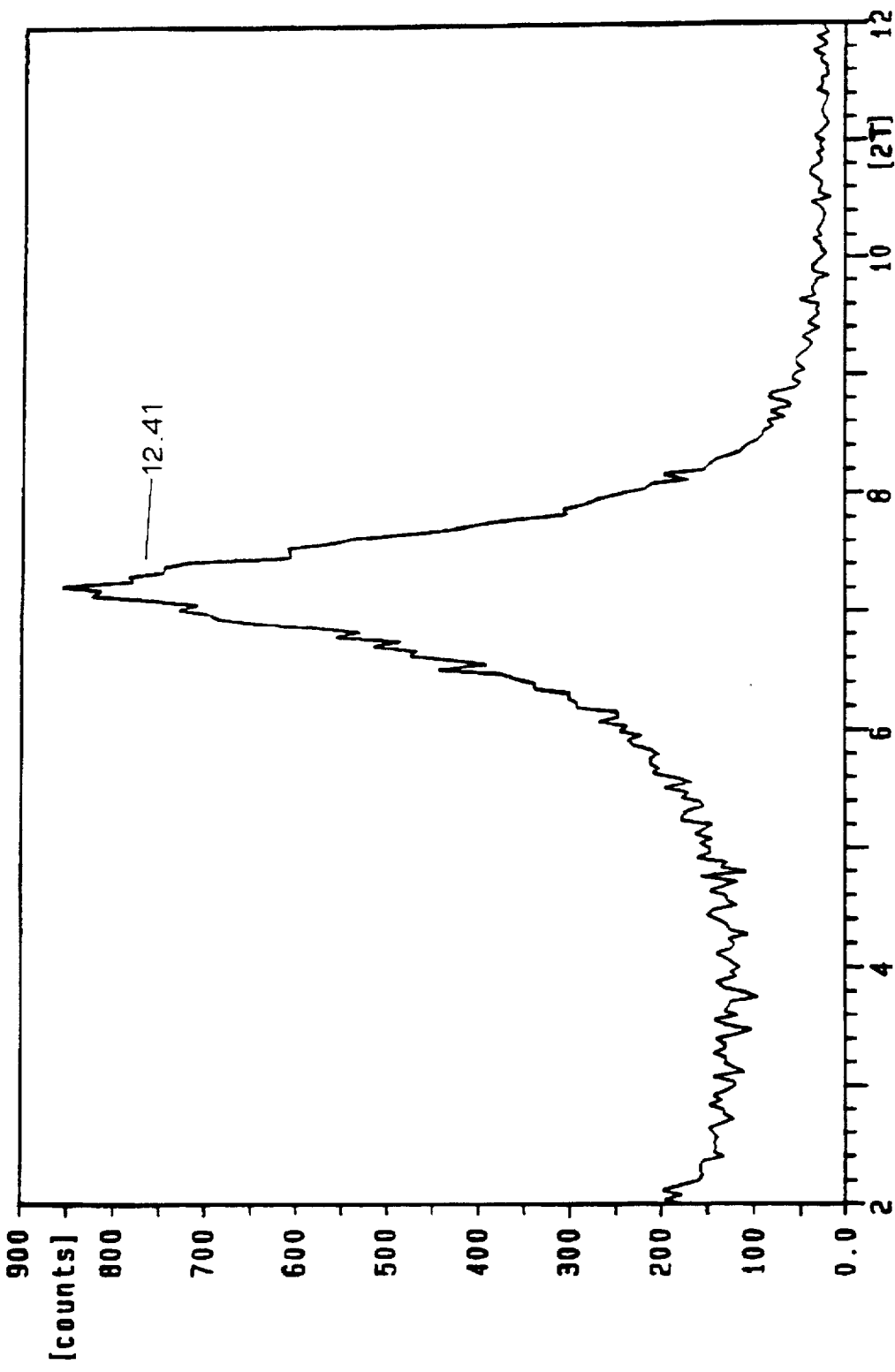
FIG. 11 is an x-ray diffraction pattern for untreated sodium montmorillonite clay, in Angstroms.

The d(001) peak of nonexfoliated (layered) and untreated sodium bentonite clay appears at about 12.4 Å, as shown in the x-ray diffraction pattern for sodium bentonite clay (containing about 10% by weight water) in FIG. 11 and in the lower x-ray diffraction patterns of FIGS. 9 and 10. FIG. 9 includes x-ray diffraction patterns of sodium bentonite clay (montmorillonite) and a PVP:clay complex that was obtained by extrusion of a blend of 20% by weight polyvinylpyrrolidone (molecular weight 10,000) and 80% by weight sodium bentonite clay (containing a crystobalite impurity, having a d-spacing of about 4.05 Å) with 35% water based on the weight of dry clay plus polymer. As shown in FIG. 9, the PVP and clay complexed since no d(001) smectite peak appears at about 12.4 Å. There are basal spacings with a d(001) peak of PVP:clay complex at about 24 Å and d(002) peak of PVP:clay complex at about 12 Å, that shows close to regular structure of this intercalated composite with a PVP:clay ratio equal to 1:4.

FIG. 10 contains x-ray diffraction patterns of sodium bentonite clay (montmorillonite) and PVP:clay complex that was obtained by extrusion of blend of 50% by weight polyvinylpyrrolidone (molecular weight 10,000) and 50% of sodium bentonite clay (containing a crystobalite impurity, having d-spacing of about 4.05 Å) with 35% water based on the weight of dry clay plus polymer. As shown in FIG. 10, the PVP:clay complexed since no d(001) smectite peak appears at about 12.4 Å. There are basal spacings with a d(001) peak of the PVP:clay complex at about 32 Å and a d(002) peak of PVP:clay complex at about 16 Å that shows close to regular structure of this intercalated composite with a PVP:clay ratio equal to 1:1. When mechanical blends of powdered sodium bentonite clay (containing about 10% by weight water) and powdered polyvinylpyrrolidone (PVP) polymer were mixed with water (about 75% by weight water), the polymer was intercalated between the bentonite clay platelets. An exothermic reaction occurred that, it is theorized, resulted from the polymer being sufficiently bonded to the internal faces of the clay platelets for exfoliation of the intercalated clay.

Treatment of the sodium bentonite with an aqueous solution of the water-soluble polymer provides an activated clay that subsequently can be intercalated with an intercalant pesticide, either containing or lacking a polar moiety. It should be noted that exfoliation of an intercalated clay did not occur unless the bentonite clay included water in an amount of at least about 4% by weight, based on the dry weight of the clay. When inter-calating in a phyllosilicate slurry, it has been found that at least about 65% by weight water, based on total weight, provides easier mixing and faster migration of the polymer and pesticide into the spaces between platelets.

It also should be noted that exfoliation can occur without shearing, i.e., the layered clay exfoliated naturally after sufficient intercalation of polymer or pesticide between the platelets of the layered bentonite, whether the intercalate was prepared using sufficient water, e.g., at least about 20% by weight, preferably about 30% to about 100% by weight, or higher, based on the dry weight of the clay, for sufficient migration of the polymer or pesticide into the interlayer spaces, and preferably also by extruding. Exfoliation should be avoided until the intercalant pesticide has contacted the activated clay.

A number of compositions were prepared containing intercalates (complexes) formed by contacting sodium bentonite clay with an activating composition comprising water and a water-soluble polymer. Sufficient sodium bentonite clay was added to the activating composition to provide a preferred weight ratio of dry clay/polymer of 4:1 (80% by weight clay/20% by weight polymer) with sufficient water such that the resulting composition contained 35 to 40% by weight water for effective extrusion of the composition through die openings of an extruder. The polymer and water are mixed with the clay to complex (intercalate) the polymer between adjacent clay platelets. The resulting polymer-intercalated clay then was contacted with an intercalant pesticide.

EXAMPLE

In general, a clay-polymer intercalate or an untreated clay are contacted with a pesticide, in the presence of water, to intercalate the pesticide between layers of the clay. Preferably, a water-miscible solvent is present in the water. An extrusion step accelerates the process of intercalating the pesticide between the clay layers. A pesticide containing a polar moiety can be intercalated into either untreated clay, a clay activated with water, or a clay-polymer intercalate. A pesticide lacking a polar moiety is intercalated into a clay-polymer intercalate. When an intercalant pesticide is added to the activated clay or the clay-polymer intercalant, the pesticide displaces the water and optional polymer from the space between adjacent clay platelets and is intercalated therein.

The following are nonlimiting examples of preparing a clay-pesticide intercalant from untreated clay.

Preparation of Clay-Herbicide Intercalates

Materials:
 Clay-sodium montmorillonite;
 Herbicide-2,4-dichlorophenoxyacetic acid (2,4-D), butyl ester To prepare clay (sodium montmorillonite)-2,4-D ester complexes (i.e., intercalates), three different processes are used for intercalation:

1. Mixture of a 2% 2,4-D butyl ester/water dispersion or emulsion with a 2% clay/water suspension in a ratio sufficient to provide a 2,4-D butyl ester concentration of at least about 8% based on the dry weight of the clay.
2. Dry clay powder (about 8% by weight moisture) is gradually added to the 2% 2,4-D butyl ester/water dispersion or emulsion in a ratio sufficient to provide a 2,4-D butyl ester concentration of at least about 8% based on the dry weight of the clay.
3. 2,4-D butyl ester (technical grade) is mixed with dry clay, the mixture is hydrated with 35 to 38% of water, based on the dry weight of the clay, and then extruded.

Mixtures 1 and 2 are agitated at room temperature for 4 hours.

The intercalation and exfoliation methods of the present invention yield clay-2,4-D butyl ester intercalates, and the results of the intercalation do not depend upon a particular method of preparation (1, 2, or 3), but do depend on the quantity of organic pesticide compound sorbed between clay platelets.

EXAMPLE

Preparation of Clay-Insecticide Intercalates

Materials:
Clay-sodium montmorillonite;
Insecticide-chlorpyrifos

To prepare clay (sodium montmorillonite)chlorpyriphos complexes (i.e., intercalates), three different processes are used for pesticide intercalation:

1. Mixture of a 2% chlorpyrifos/water dispersion with a 2% sodium montmorillonite clay/water suspension in a ratio sufficient to provide a chlorpyrifos concentration of at least about 8% based on the dry weight of the clay.
2. Dry clay powder is gradually added to a 2% chloripyrifos/water dispersion in a ratio sufficient to provide a chlorpyrifos concentration of at least about 8% based on the dry weight of the sodium montmorillonite clay.
3. Dry sodium montmorillonite clay is moisturized with chlorpyrifos/water dispersion to 20–80% by weight water, and then extruded.

The mixtures 1 and 2 are agitated at room temperature for 4 hours. The intercalation method yields a clay-chlorpyrifos intercalate regardless of the method of preparation.

In another example, a dispersion or emulsion of 30% by weight 2,4-dichlorophenoxy acetic acid (2,4-D) and 70% by weight dicamba is prepared in water, at a concentration of 45% by weight of the 2,4-D and dicamba mixture. Thirty grams of the 2,4-D/dicamba mixture is added to a 50 ml (milliliter) beaker, and while this mixture is mixed vigorously, 1.5 grams of sodium montmorillonite (i.e., POLARGEL NF from AMCOL International Corporation) is added. The weight ratio of clay to (2,4-D dicamba mixture) is—1.9. The mixture is vigorously mixed and heated for 1 hour at 85° C.

The heated mixture is allowed to cool to room temperature and the resulting product is subjected to x-ray diffraction. The x-ray diffraction pattern shows that the 2,4-D/dicamba is intercalated in the clay because the periodicity, or d(001) value, of the clay is increased from 12.4 Å, showing that 2,4-D and dicamba are intercalated between adjacent clay platelets.

All methods of the present invention used for intercalation yield clay-pesticide intercalates, and the results of the intercalation do not depend upon method of preparation (1, 2, or 3), but do depend on the quantity of pesticide sorbed between clay platelets.

The following are further illustrative and nonlimiting examples of the present invention. The following examples illustrate intercalated layer materials wherein the intercalant pesticide is α,α,α-trifluoro-2-6-dinitro-N,N-dipropyl-p-toludine, having the common name trifluralin and available from Dow Elanco, Indianapolis, Ind.

| EXAMPLE | #1 | #2 | #3 | #4 | #5 | #6 |
|---|---|---|---|---|---|---|
| Belle Yellow Clay[1] | 200[4] | | | 200 | 500 | 400 |
| PDTQ[2] Organo Clay | | 200 | 200 | | | |
| IVP (Surface Modified Clay)[3] | | | | | | |
| Deionized Water (pH 3) | 90 | | | | 150–170 | 150–170 |
| Deionized Water (normal pH) | | | | 60 | | |
| Trifluralin | 60 | 142 | 86 | 101 | 214 | 171 |
| PEG[5] | | | | 34 | | |
| PEG[6] | | | | | | |
| PVP[7] | | | | | | |
| PVA[8] | | | | | | |
| Solvent | 35[9] | 50[9] | 70[10] | | 90[9] | 43[9] |

| EXAMPLE | #7a | #7b | #8a | #8b | #9a | #9b |
|---|---|---|---|---|---|---|
| Belle Yellow Clay[1] | 400 | 200 | 200 | | | 200[4] |
| PDTQ[2] Organo Clay | | | | | | |
| IVP (Surface Modified Clay)[3] | | | | 200 | 200 | |
| Deionized Water (pH 3) | | | | | | |
| Deionized Water (normal pH) | | 70 | 170–180 | 130 | 130 | 96 |
| Trifluralin | 300 | 150 | 153 | 120 | 86 | 102 |
| PEG[5] | | | | | | |
| PEG[6] | 300 | 150 | | | | |
| PVP[7] | | | 30 | | | |
| PVA[8] | | | | | | 40 |
| Solvent | | | 38[9] | 24[9] | 22[9] | 26[11] |

| EXAMPLE | #10a | #10b | #10c | #10d | #11a | #11b | #11c |
|---|---|---|---|---|---|---|---|
| Belle Yellow Clay[1] | 300 | 300 | 200 | 200 | 200 | 200 | 200 |
| PDTQ[2] Organo Clay | | | | | | | |
| IVP (Surface Modified Clay)[3] | | | | | | | |
| Deionized Water[4] (pH 3) | 110 | | | | | | |
| Deionized Water[4] (normal pH) | | 190–210 | 130–140 | 88 | 80 | 100 | 95 |
| Trifluralin[4] | 128 | 154 | 102 | 94 | 150 | 70 | 60 |
| PEG[5] | | | | | | | |
| PEG[6] | | | | | 150 | 50 | 30 |
| PVP[7] | | | | | | | |
| PVA[8] | | 60 | 40 | 20 | | | |
| Solvent | 31[11] | 39[11] | 26[11] | 24[11] | 20[9] | 10[9] | 10[9] |

[1] an unmodified sodium bentonite clay powder having particles collected on a 325 mesh sieve (U.S. Sieve or Tyler), i.e., at least 44 microns in diameter;
[2] a sodium bentonite clay surface treated with a quaternary ammonium compound;
[3] a sodium bentonite clay surface treated with 20% by weight polyvinylpyrolidone;
[4] amounts of all ingredients are expressed as grams;
[5] polyethylene glycol, PLURACOL E-4000, available from BASF Corporation, Parsippany, NJ;
[6] polyethylene glycol, PLURACOL E-400, available from BASF Corporation, Parsippany, NJ;
[7] polyvinylpyrrolidone, PVP K-15, available from GAF Chemicals Corp., Wayne, NJ;
[8] polyvinyl alcohol, VINOL 540, available from Air Products and Chemicals, Inc., Allentown, PA;
[9] isopropyl alcohol;
[10] xylene; and
[11] ethylene glycol monobutyl ether.

X-ray diffraction patterns for wet and/or dry intercalated pesticides of Examples #1 through #11c were taken, and are presented herein as FIGS. 13–22. In FIGS. 13–30, the peak at 11.21 Å is attributed to trifluralin that is in excess or crystallized on the surface of the clay. The intercalated pesticides of Examples #1–#11c were prepared from activated clay in accordance with the methods described in the previous examples. In each example, crystallization of trifluralin on the clay was minimized because crystallized trifluralin is not available for intercalation.

Figure 13:
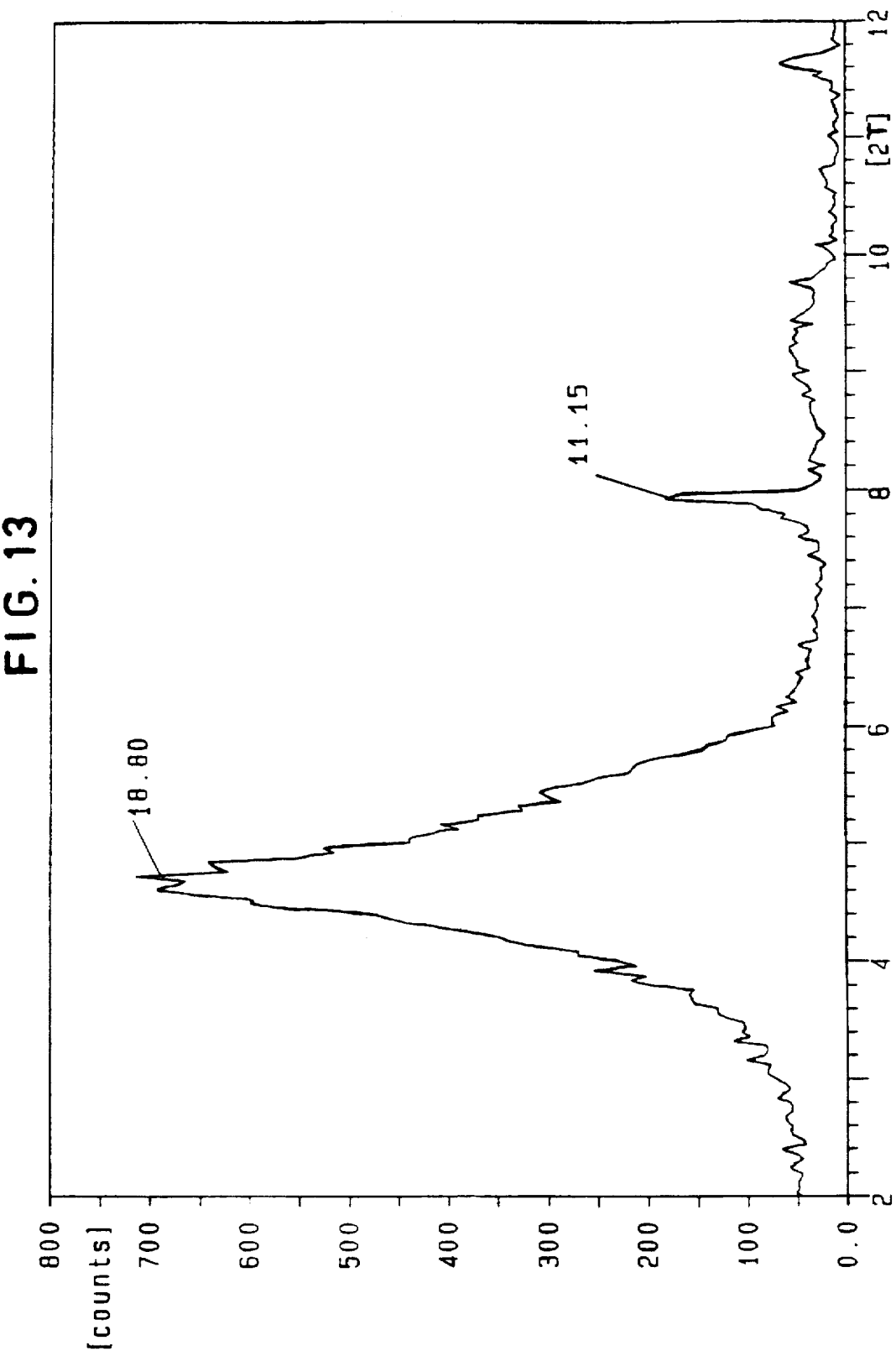
FIGS. 13 and 14 are x-ray diffraction patterns, respectively, of wet and dry samples of Example #1.
Figure 14:
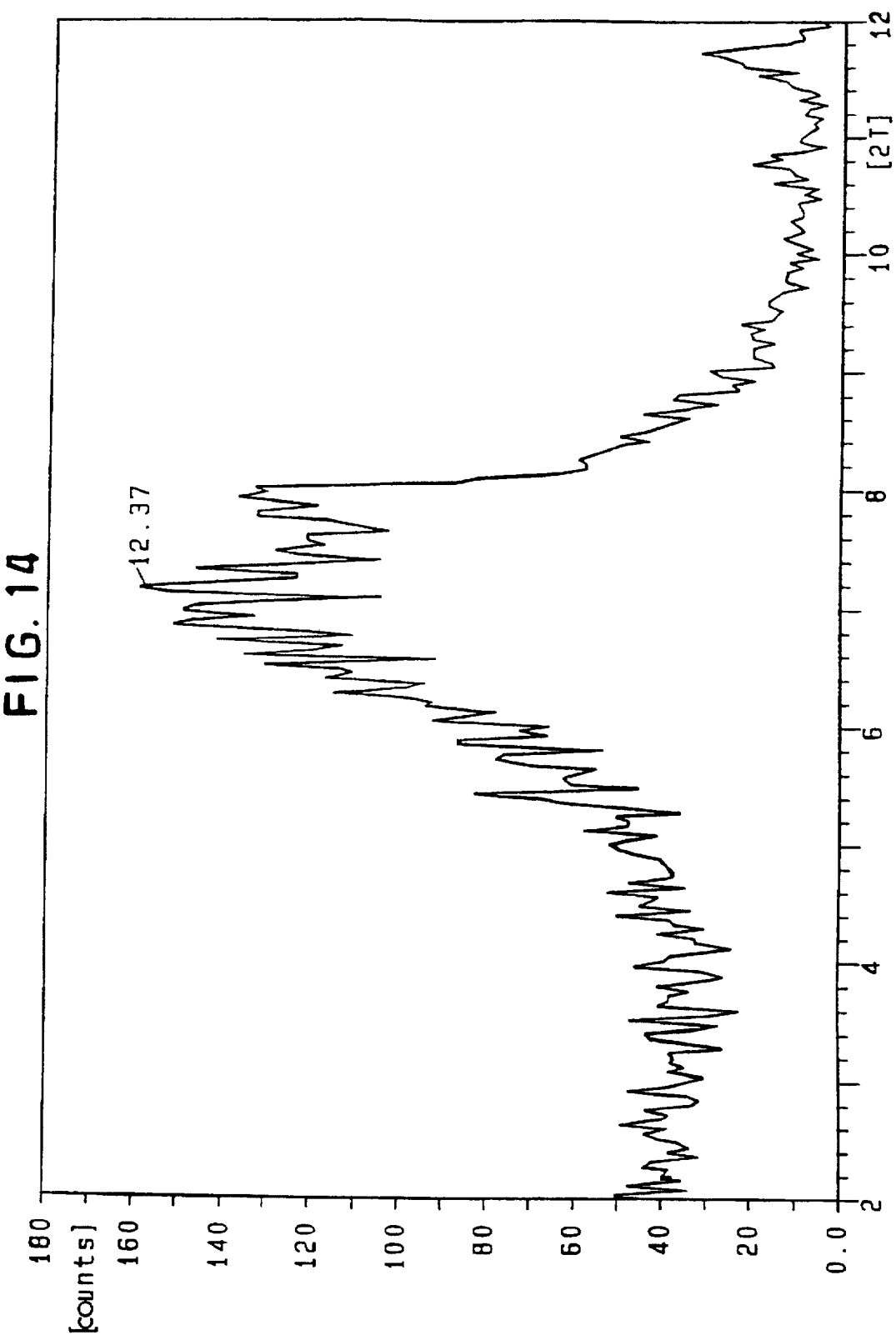

Example 1 and FIGS. 13 and 14 show that 23% trifluralin was intercalated into the clay. Attempts to intercalate trifluralin into a quaternary ammonium-treated clay failed in Examples 2 and 3.

In particular, FIG. 13 shows that the intercalated clay has a periodicity of 18.8 Å, an increase from a periodicity of 12.4 Å for untreated clay. The wet sample was dried in a vacuum oven ($10^{-3}$ torr) at 60° C. for 48–60 hours causing the trifluralin to sublimate from the clay, as illustrated in FIG. 14, i.e., periodicity of 12.37 Å. Importantly, FIG. 14 illustrates that a pesticide can be released from the intercalate to perform its intended function.

In preparing the intercalates of Examples #1–#11c, it was found that warming the activated clay/trifluralin mixture to about 40° C. to about 60° C., without vacuum, and extruding the warm mixture produces a more homogeneous intercalated product. However, because trifluralin sublimates, heating the mixture above about 60° C. to 65° C. produces a product having high amounts of crystalline trifluralin. It is envisioned that other pesticides, that do not sublimate, can be heated up to about 80° C. without adverse effects.

Examples #2 and #8a were prepared using about 40% trifluralin. Each intercalated product showed significant crystallization of trifluralin. Accordingly, the upper limit for intercalating trifluralin is about 40%, and preferably about 30%. Examples #9a, #9b, #10d, and #11c had very little visible trifluralin crystals, showing that 30% by weight trifluralin can be intercalated into an activated clay. Example #9a utilized a clay that was surface treated with polyvinylpyrrolidone, whereas the clay used in Examples #9b, #10d, and #11c had 20% PVA, 10% PVA, and 10% PEG, respectively, intercalated into the clay prior to contact with the trifluralin. Examples #9b and #10d were extruded twice. X-ray diffraction patterns for Examples #9a, #9b, #10d, and #11c are set forth in FIGS. 15–22.

Figure 15:
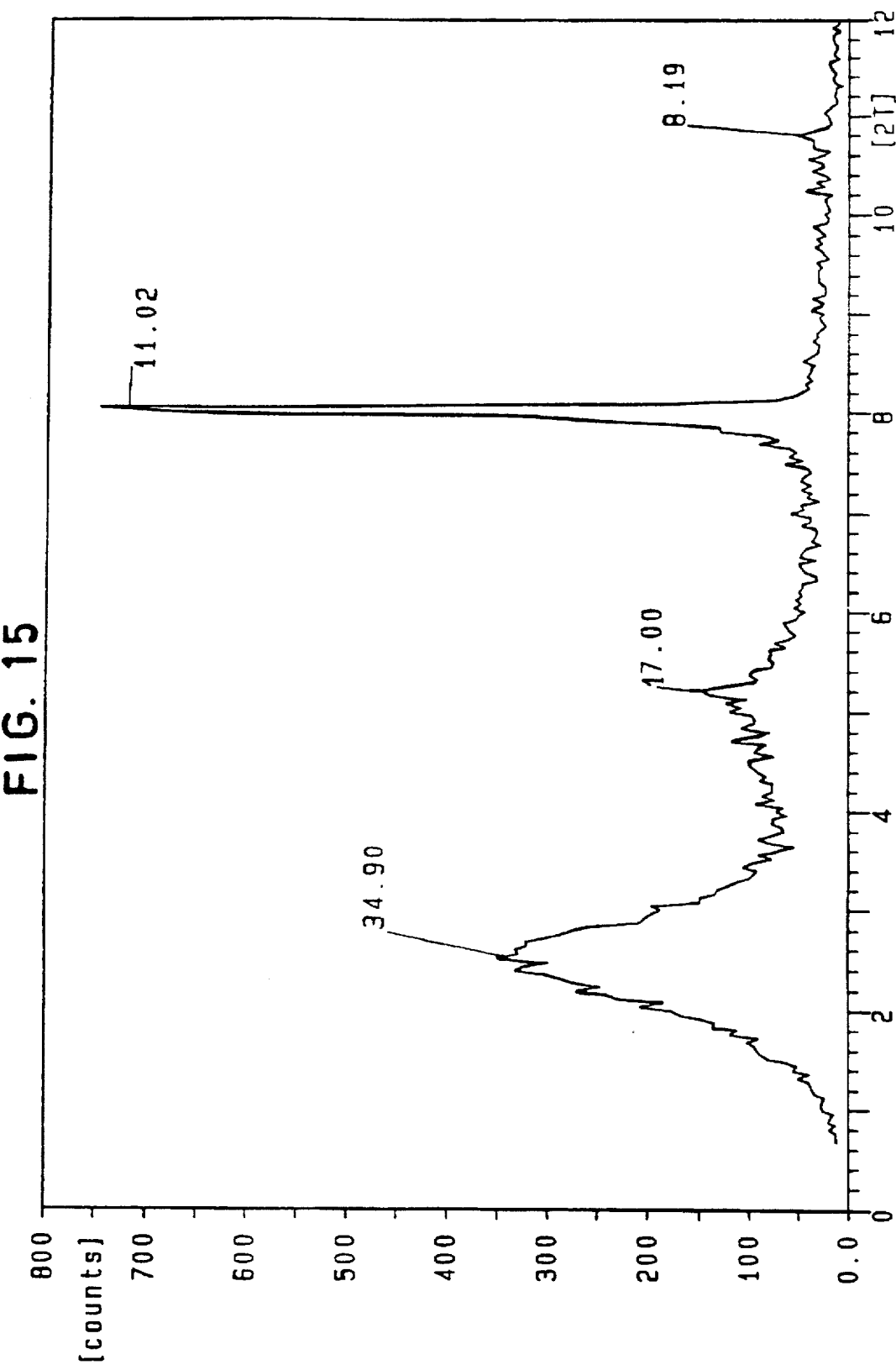
Figure 16:
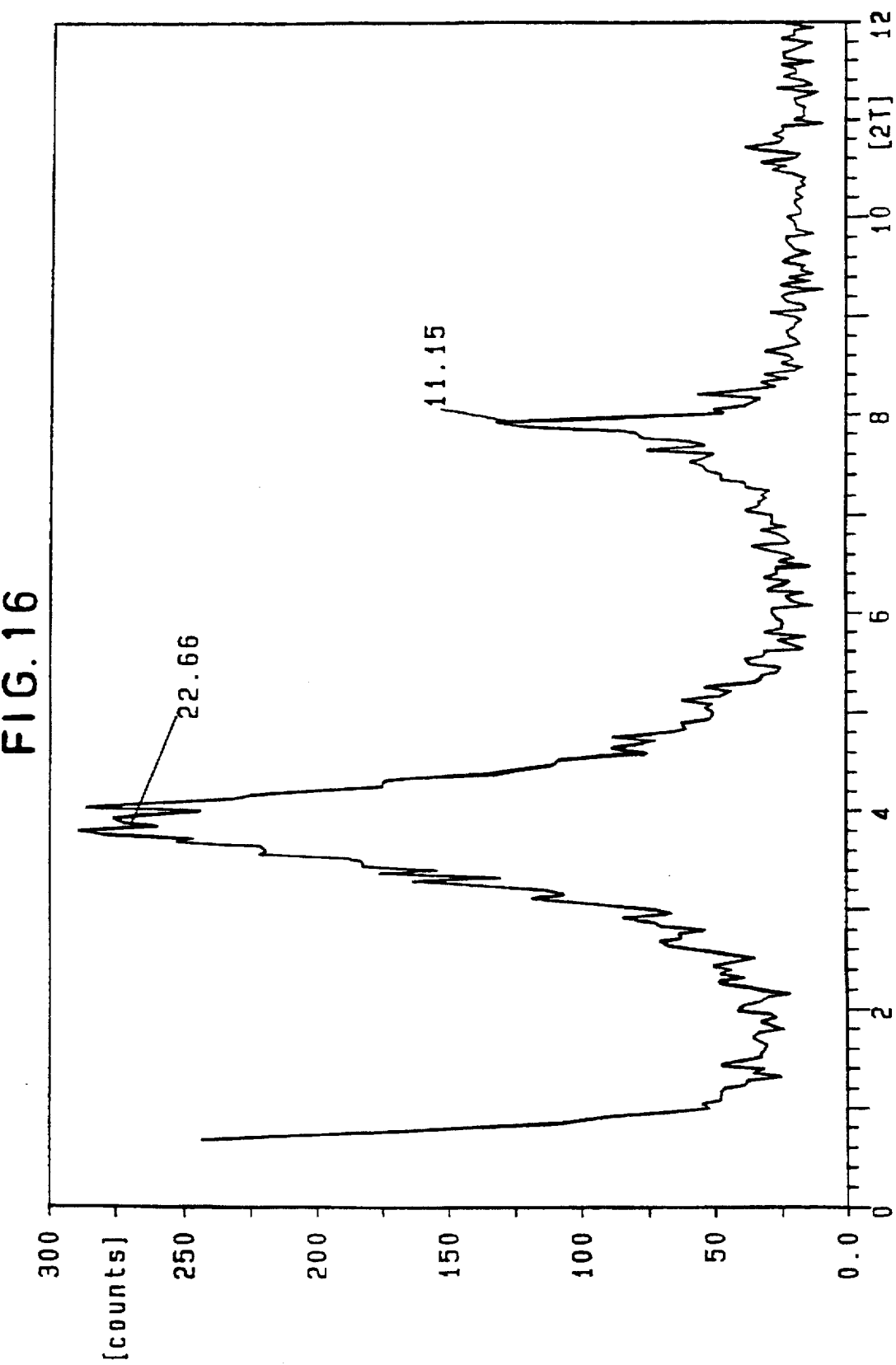

With respect to FIGS. 15 and 16 and Example #9a, the surface-treated clay, prior to intercalation has a periodicity of about 23 Å. FIG. 15 shows that periodicity increased to 34.9 Å after intercalation of trifluralin into the clay. FIG. 16 is an x-ray diffraction after drying the intercalated clay showing that trifluralin is released from the intercalated clay.

Figure 17:
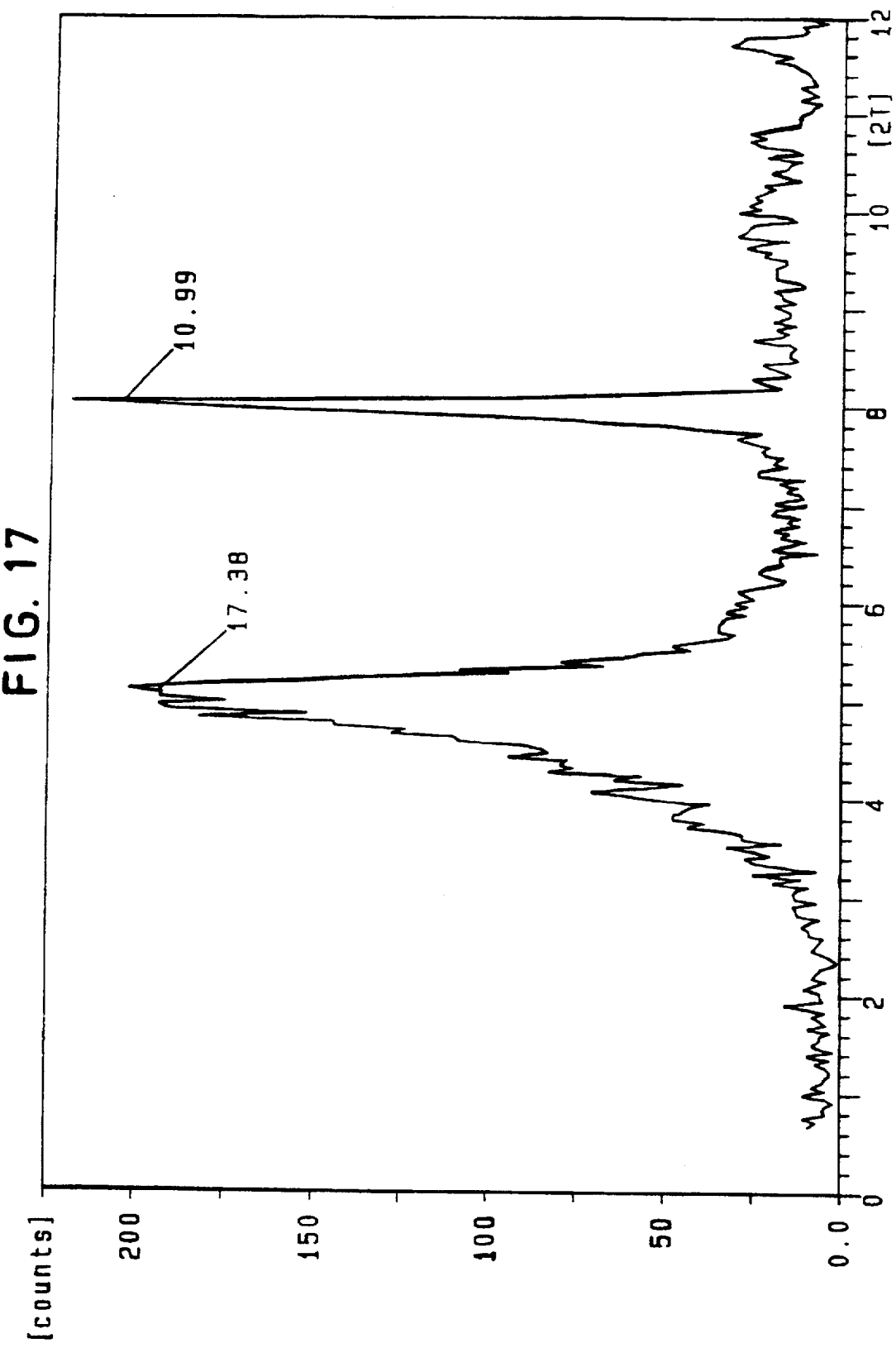
FIGS. 17 and 18 are x-ray diffraction patterns, respectively, of wet and dry samples of Example #9b.
Figure 18:
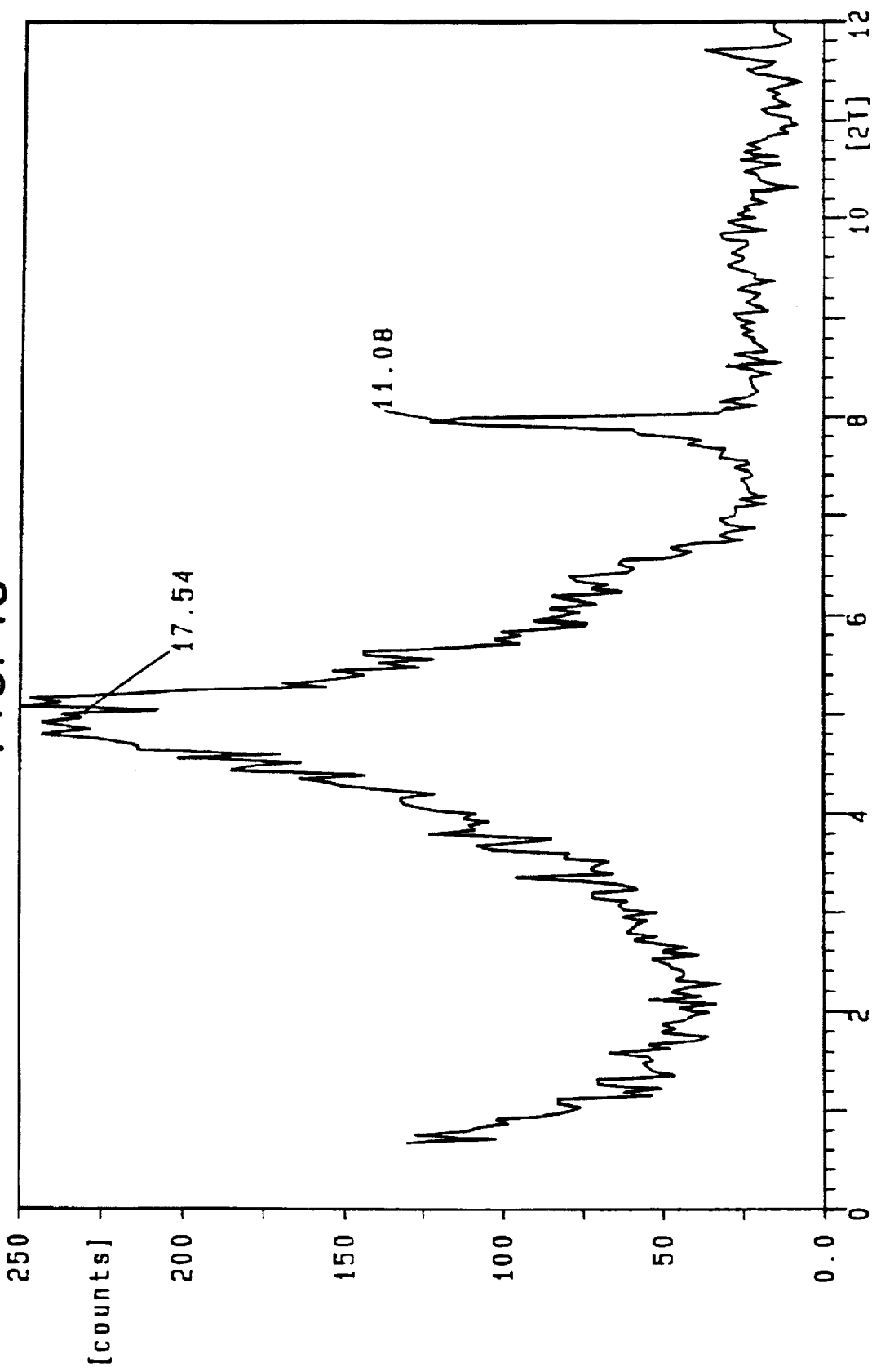
Figure 19:
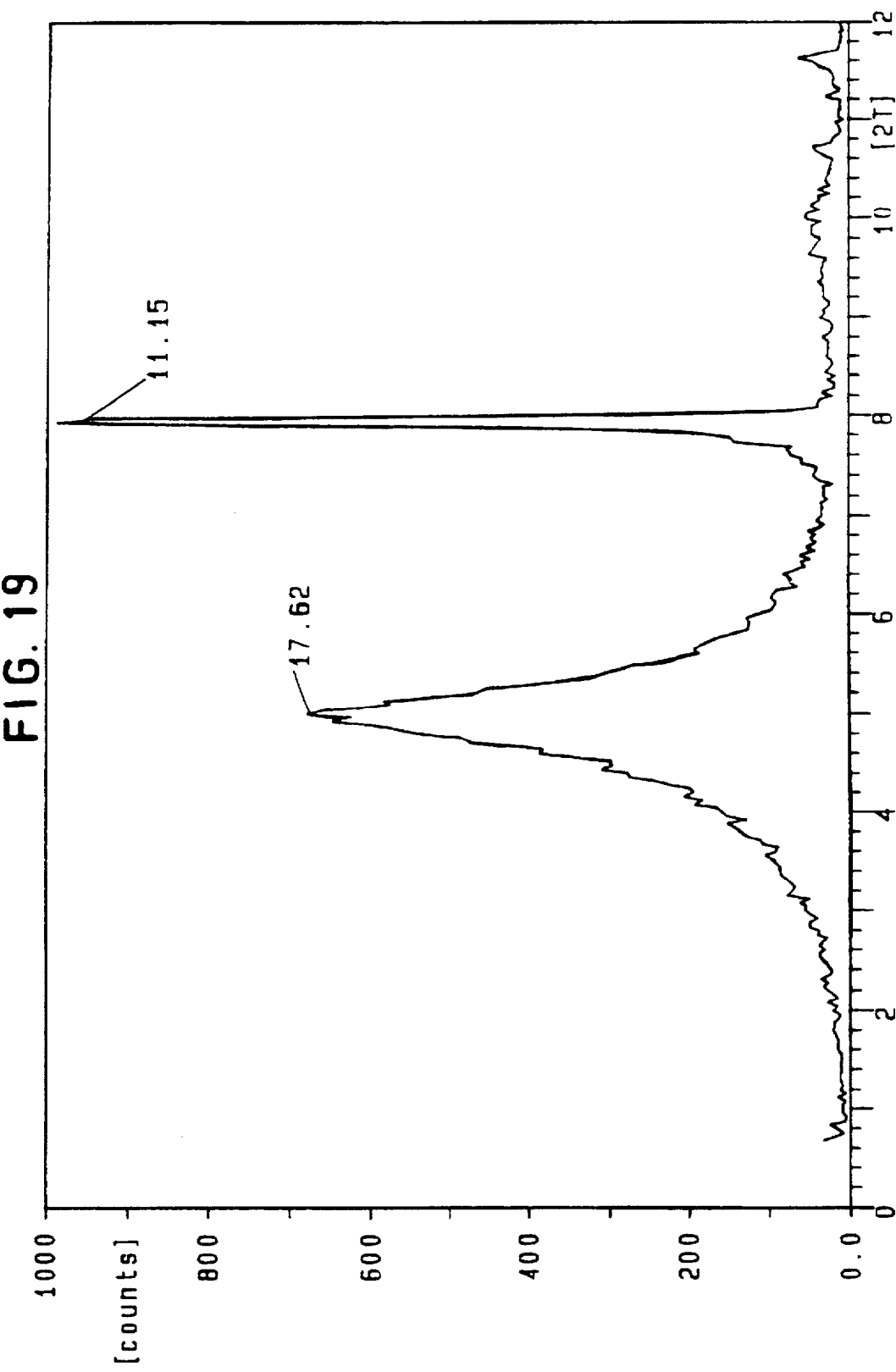
FIGS. 19 and 20 are x-ray diffraction patterns, respectively, of wet and dry samples of Example #10d.
Figure 20:
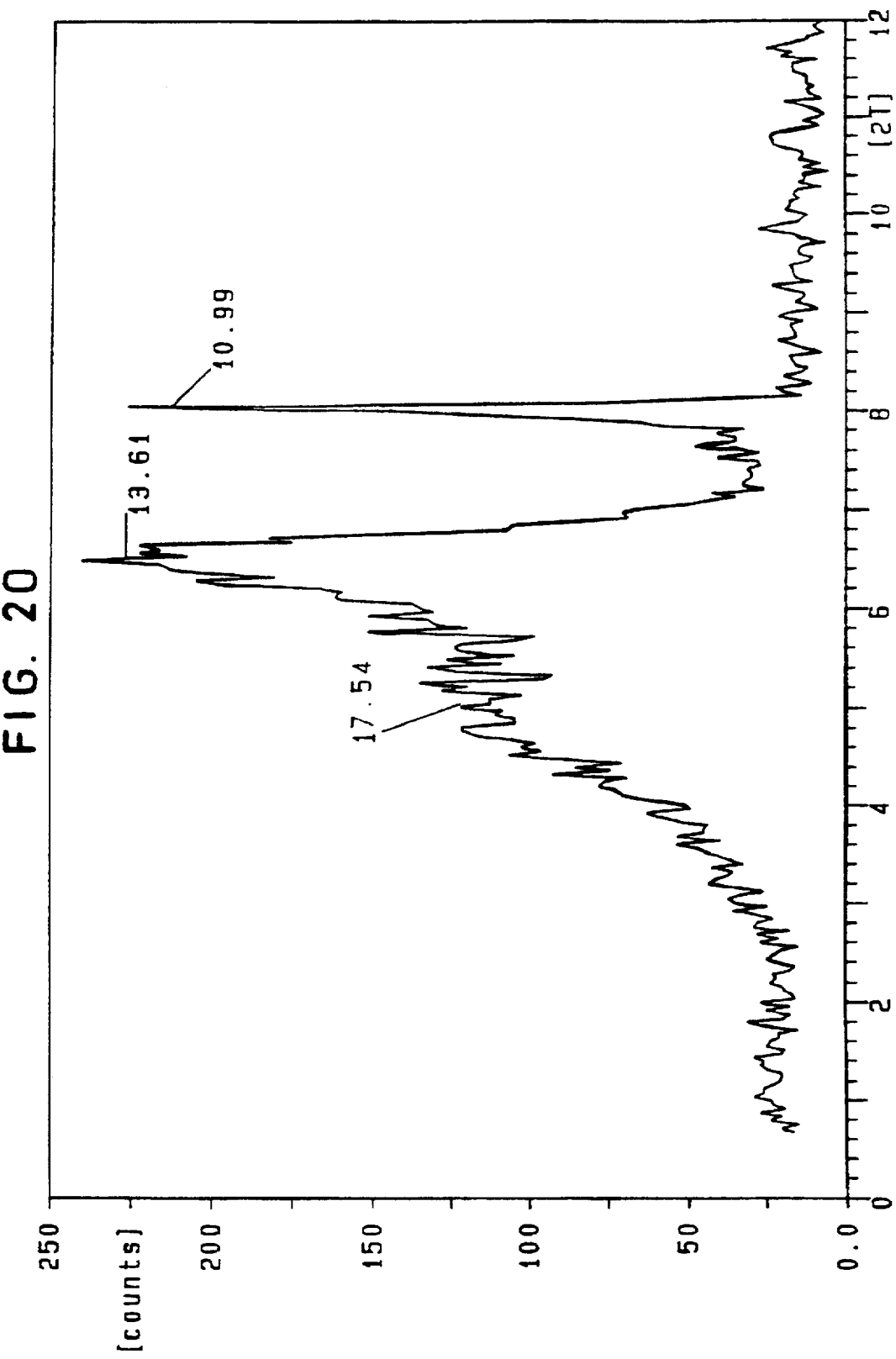
Figure 21:
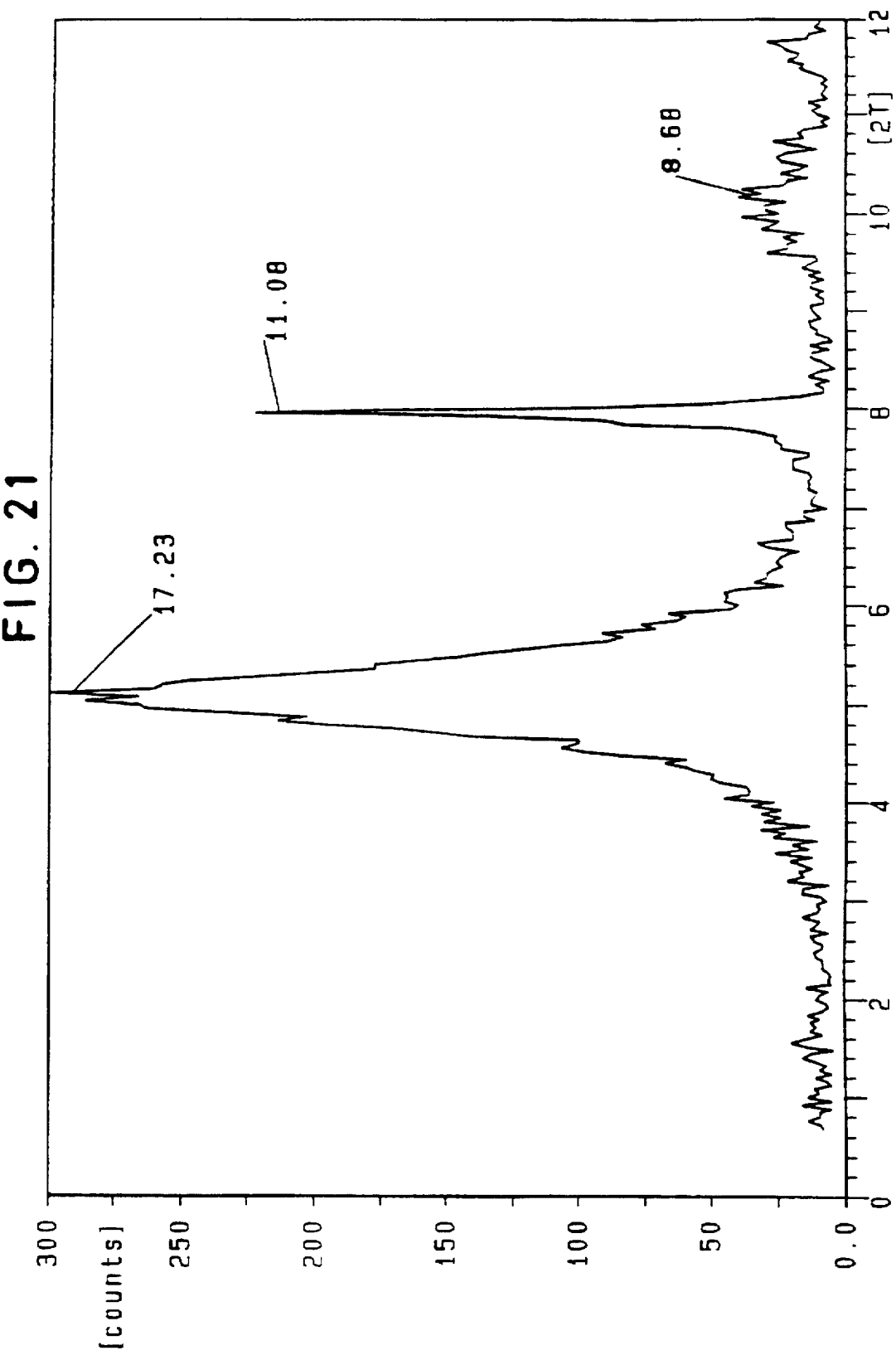
FIGS. 21 and 22 are x-ray diffraction patterns, respectively, of wet and dry samples of Example #11c.
Figure 22:
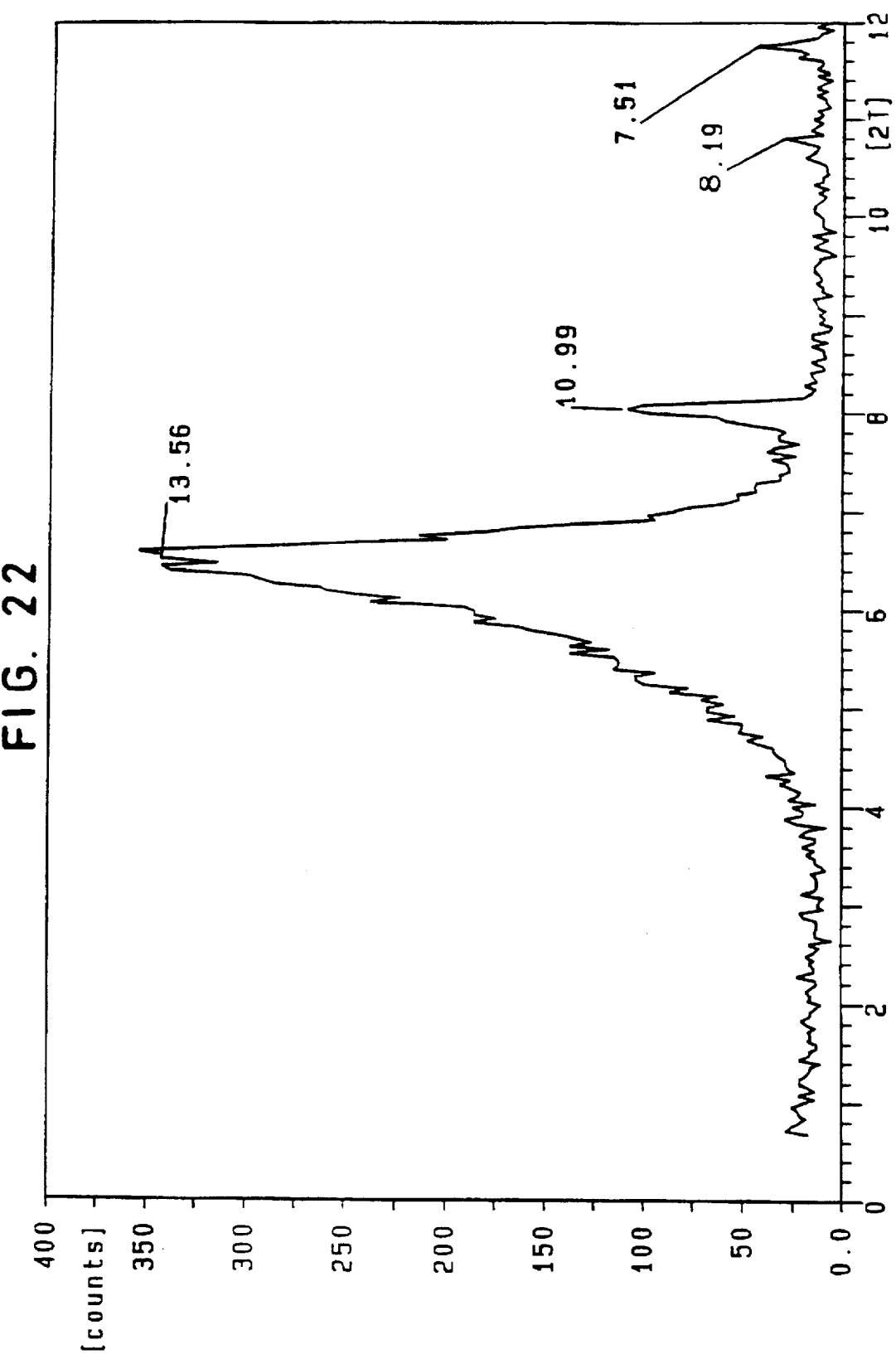

FIGS. 17 and 18 are x-ray diffraction patterns of Example #9b showing trifluralin is intercalated (i.e., periodicity of 17.38 Å), and after drying overnight at 67° C. without a vacuum remains intercalated (i.e., FIG. 18, periodicity 17.54 Å). FIGS. 19–22 show similar results, including release of the pesticide, for Examples #10d and #11c using less PVA or using PEG as the intercalant polymer.

EXAMPLE 12a 200 g Belle Yellow clay (powder)

20 g PVA (powder mixed dry in clay)

94 g Trifluralin 115 g Deionized water (normal pH)

Figure 23:
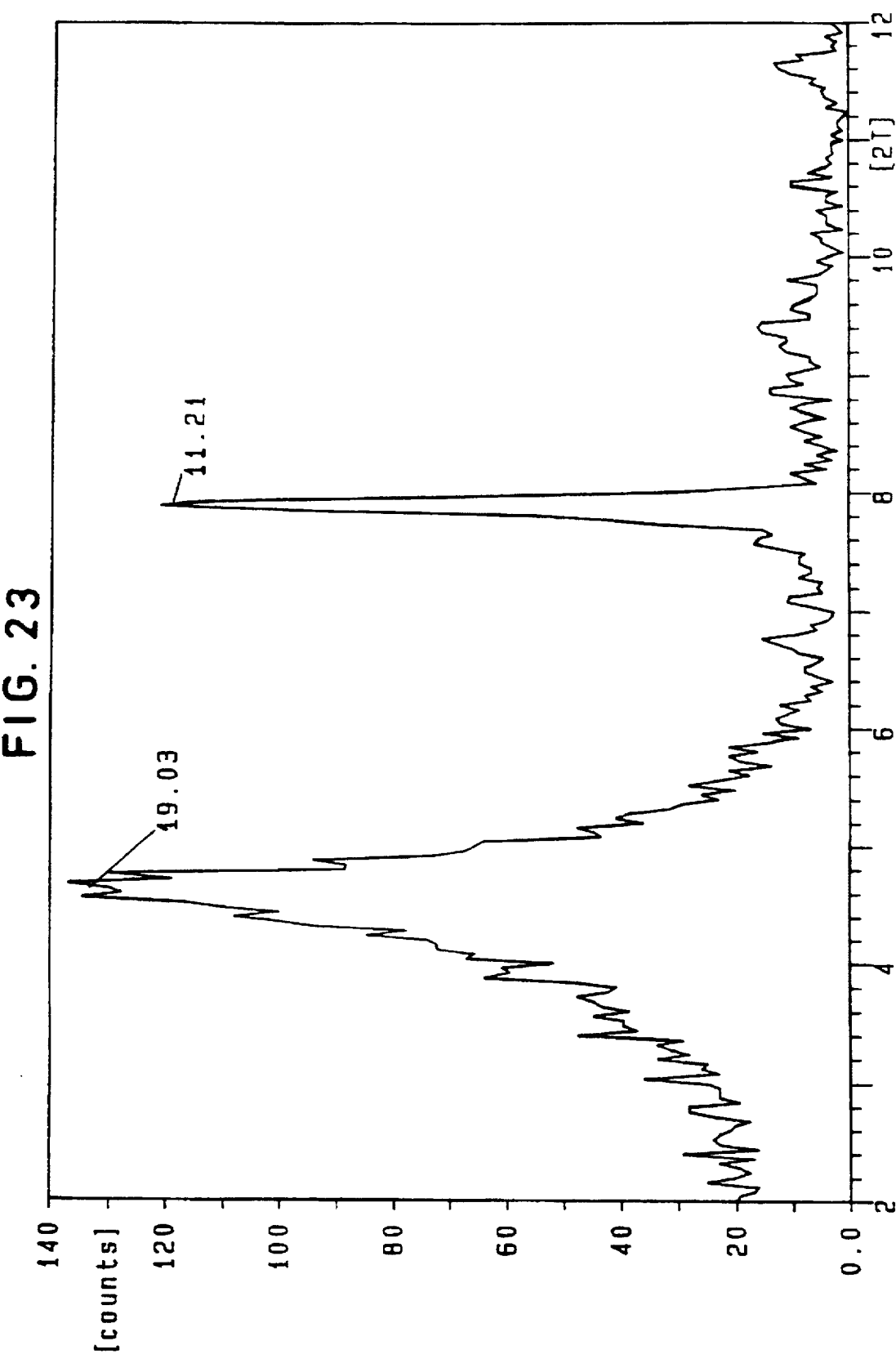
Figure 24:
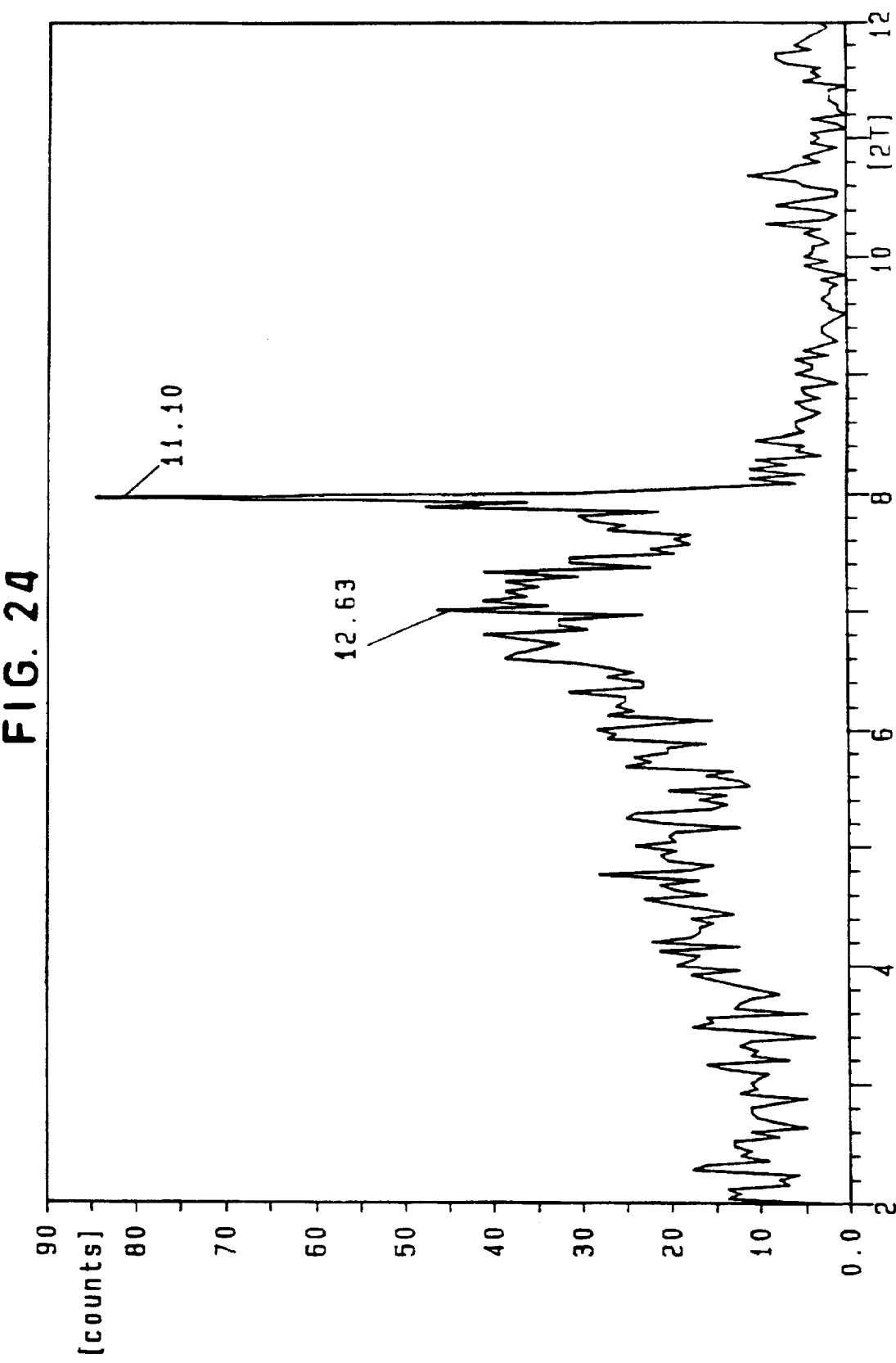

No organic solvents were used in Example 12a. The ingredients were admixed and heated at about 40° C. to about 60° C. during mixing, and the resulting mixture was extruded twice. The extruded intercalated product was dried at 29° C. Trifluralin crystallized on the sides of the mixing vessel. Small crystals of trifluralin were visible in the final product. The x-ray diffraction patterns of wet and dry samples of Example 12a are set forth in FIGS. 23 and 24. FIGS. 23 and 24 show that trifluralin intercalated between platelets of the clay (i.e., FIG. 23, periodicity is 19.03 Å) and is released from the intercalate (i.e., FIG. 24, periodicity is 12.63 Å).

EXAMPLE 12b 200 g AEG clay (granular)

20 g PVA (powder mixed dry in clay)

94 g Trifluralin 115 g Deionized water (normal pH)

Granular clay was used in Example 12b. The AEG clay is a granular sodium bentonite having a majority of the particles (i.e., at least 60% by weight) ranging from 210 to 840 microns in diameter. In particular, a maximum of 20% by weight of the particles are larger than 840 microns in diameter, and a maximum of 20% by weight of the particles are smaller than 210 microns in diameter. The granular clay absorbed water to activate the outer portion of the granular, but insufficient water was present to completely hydrate the granules. Therefore, the granules did not absorb the water evenly, causing the granules to clump. Clumping of the granules caused the trifluralin to coat the outside of the clumps and form crystals. Trifluralin crystals were observed in the finished intercalated pesticide even after two extrusions. The trifluralin, therefore, was not evenly dispersed throughout the clay. The product was dried at 33° C. The x-ray diffraction patterns of wet and dry samples of Example 12b are set forth in FIGS. 25 and 26.

Figure 25:
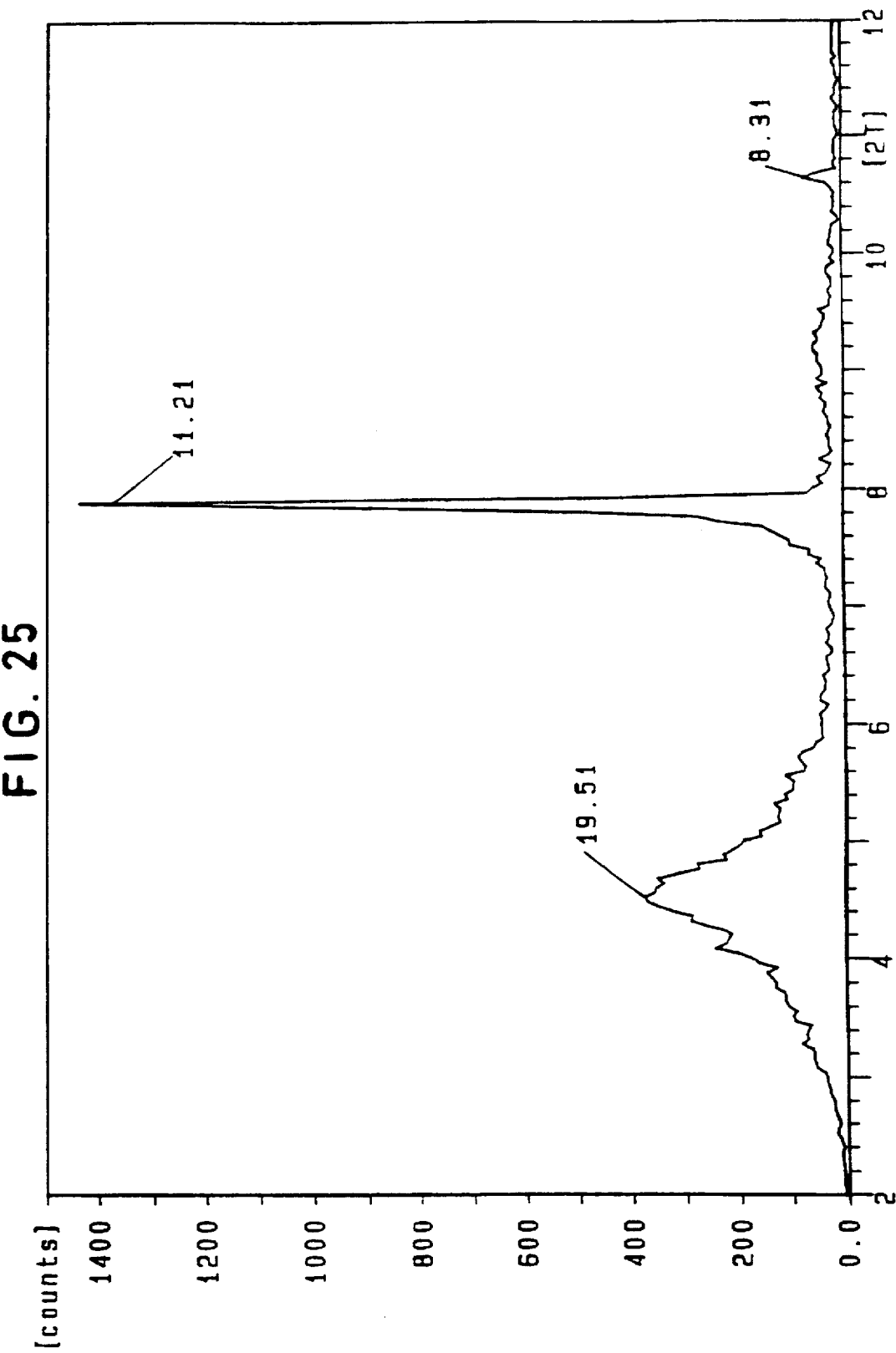
FIGS. 25 and 26 are x-ray diffraction patterns, respectively, of wet and dry samples of Example #12b.
Figure 26:
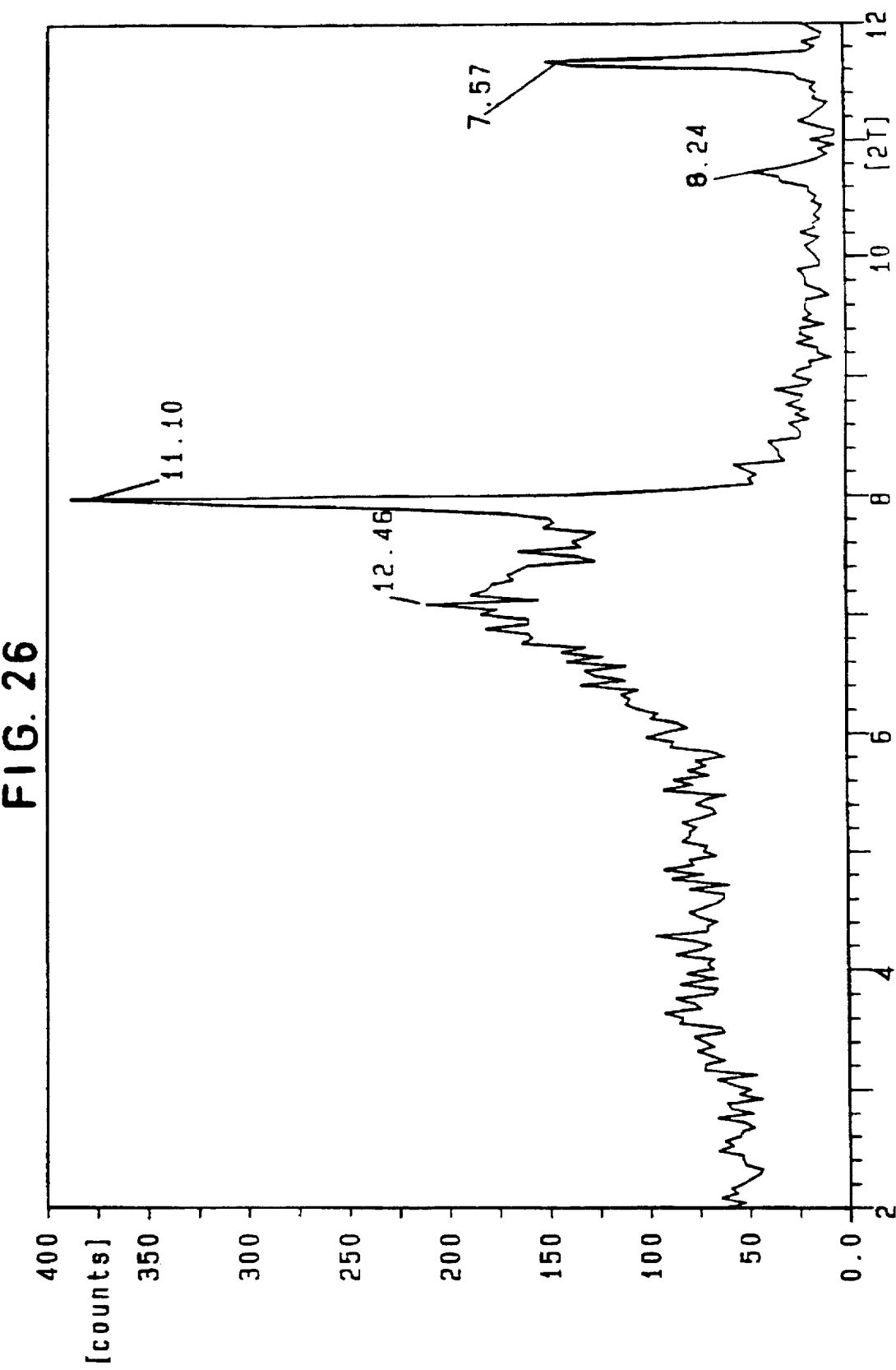
Figure 27:
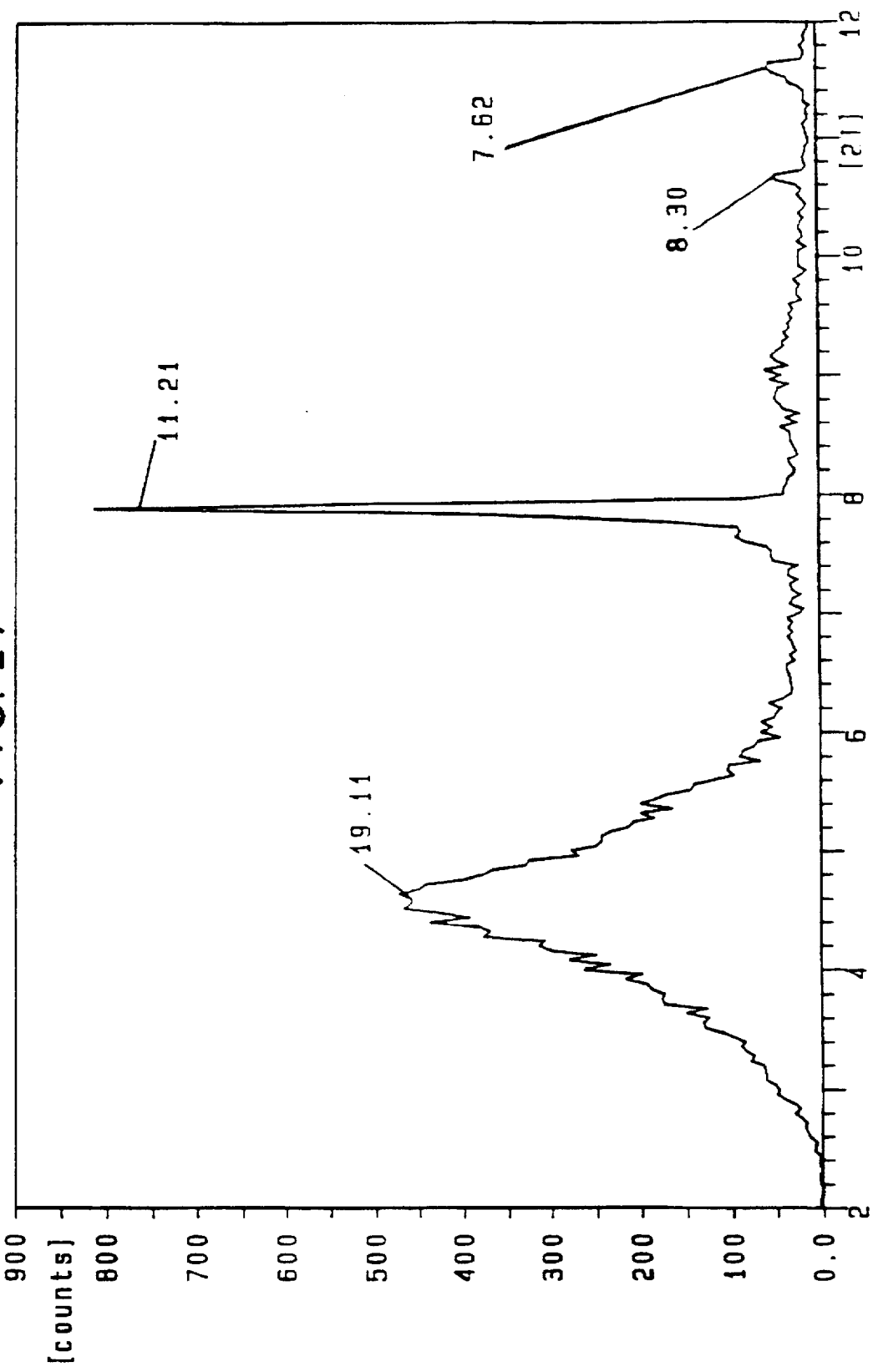
FIGS. 27 and 28 are x-ray diffraction patterns, respectively, of wet and dry samples of Example #12c.
Figure 28:
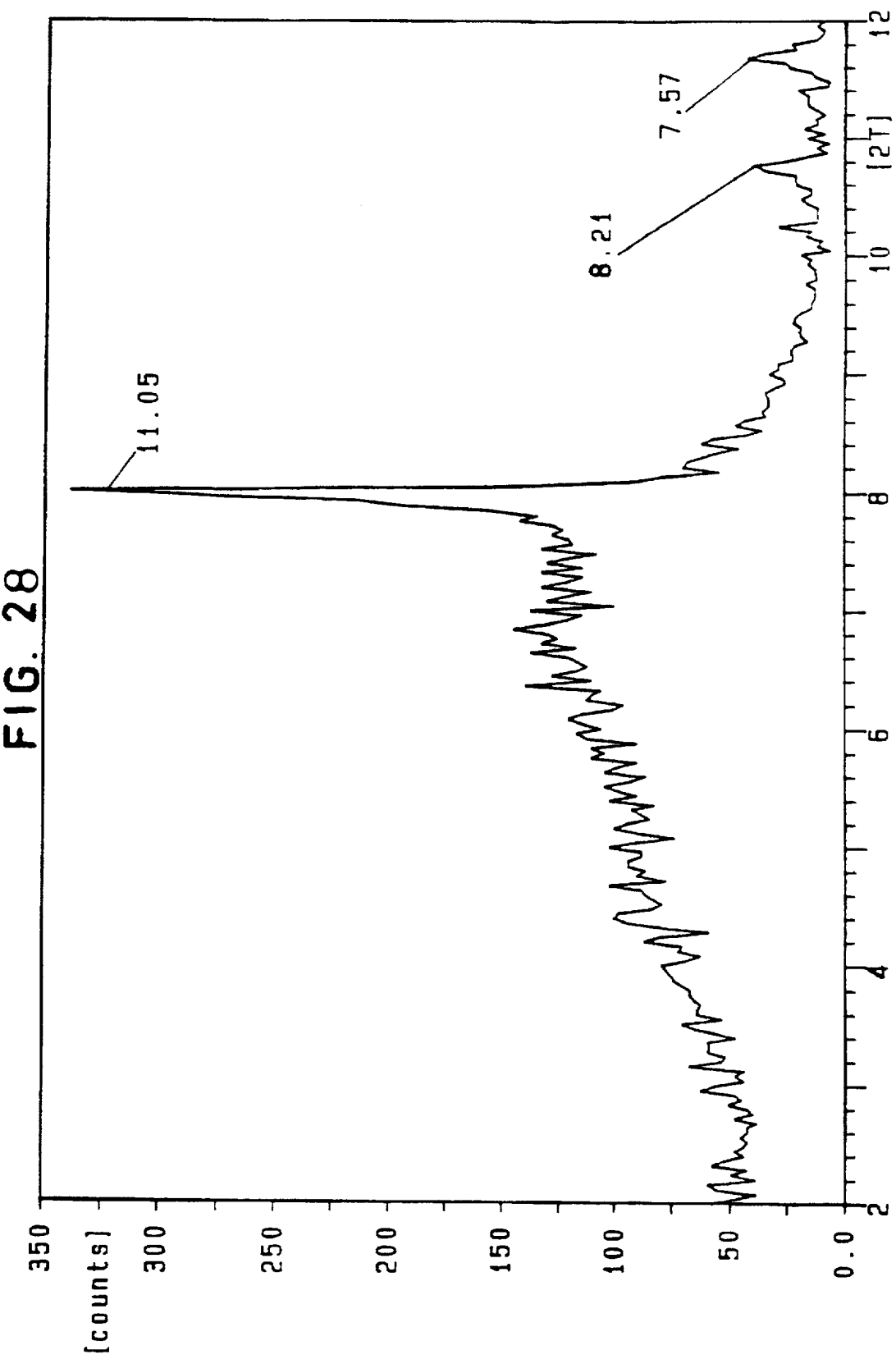
Figure 29A:
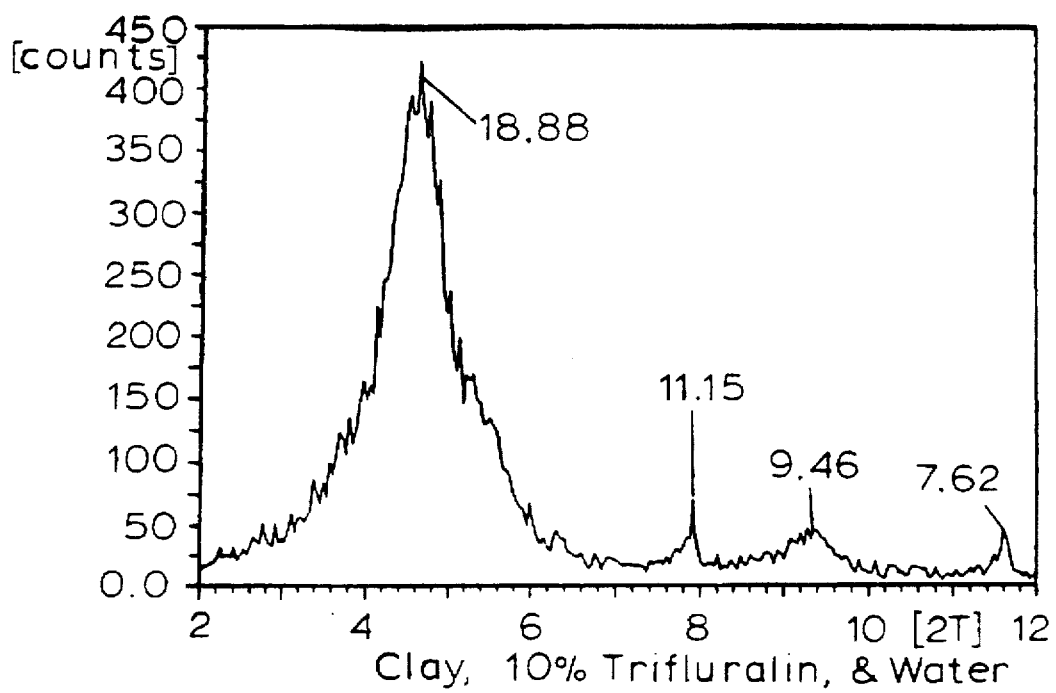
FIGS. 29 and 30 are x-ray diffraction patterns, respectively, of wet and dry samples of Examples #13a–d.
Figure 29B:
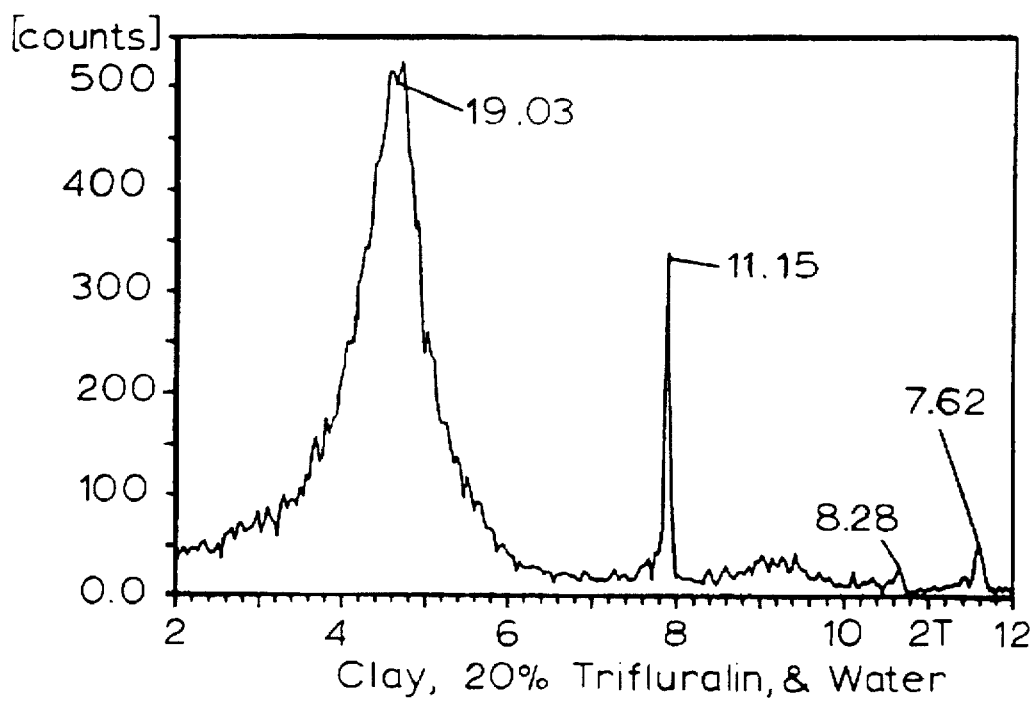
Figure 29C:
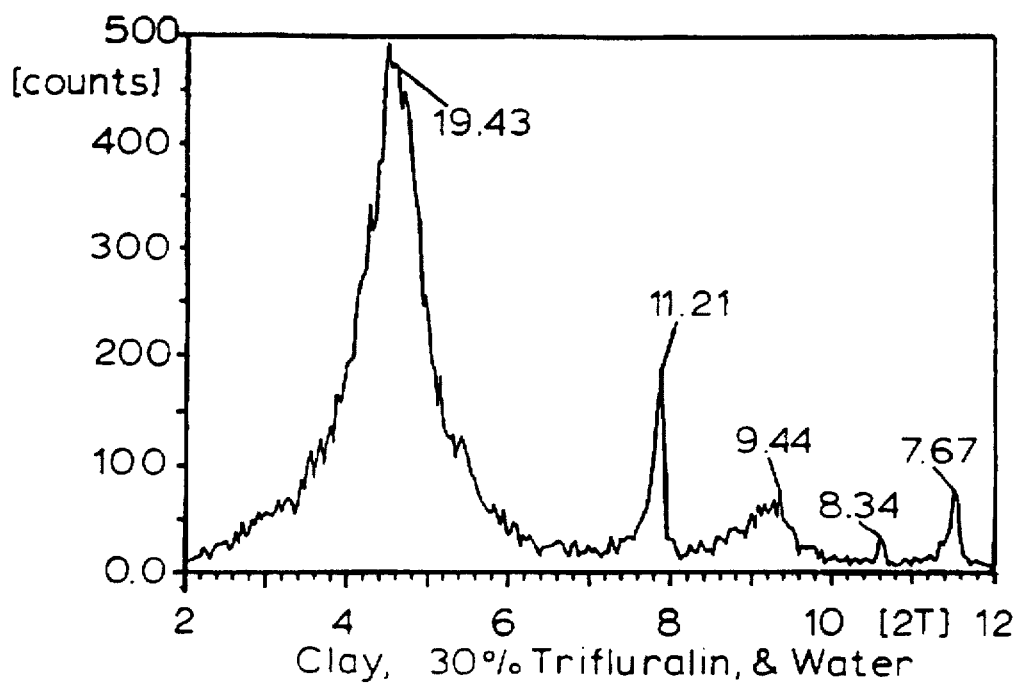
Figure 29D:
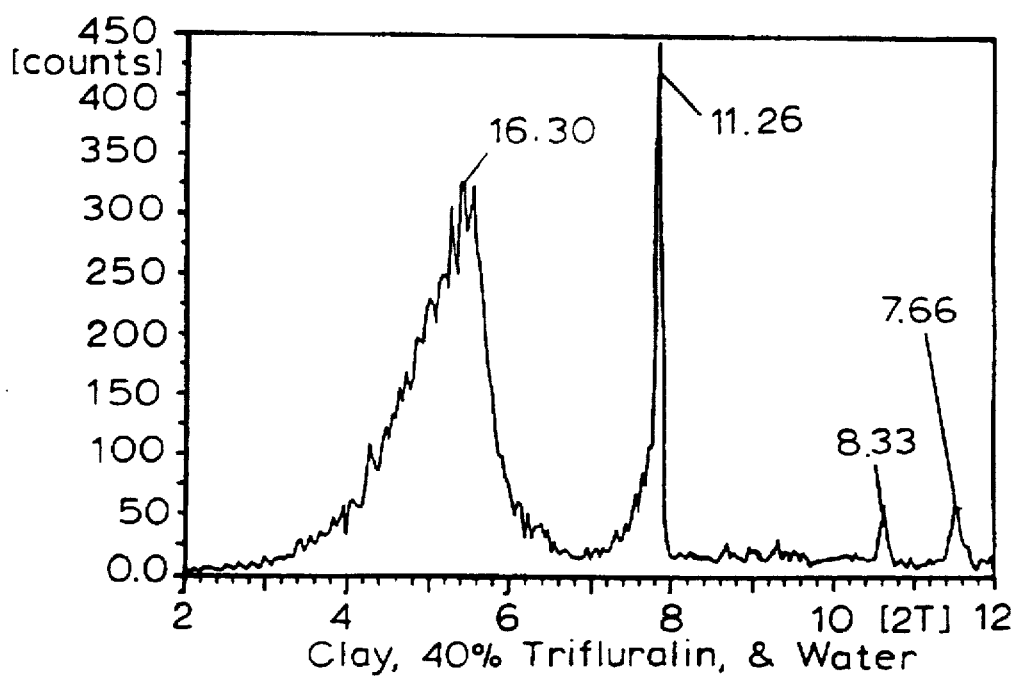
Figure 30A:
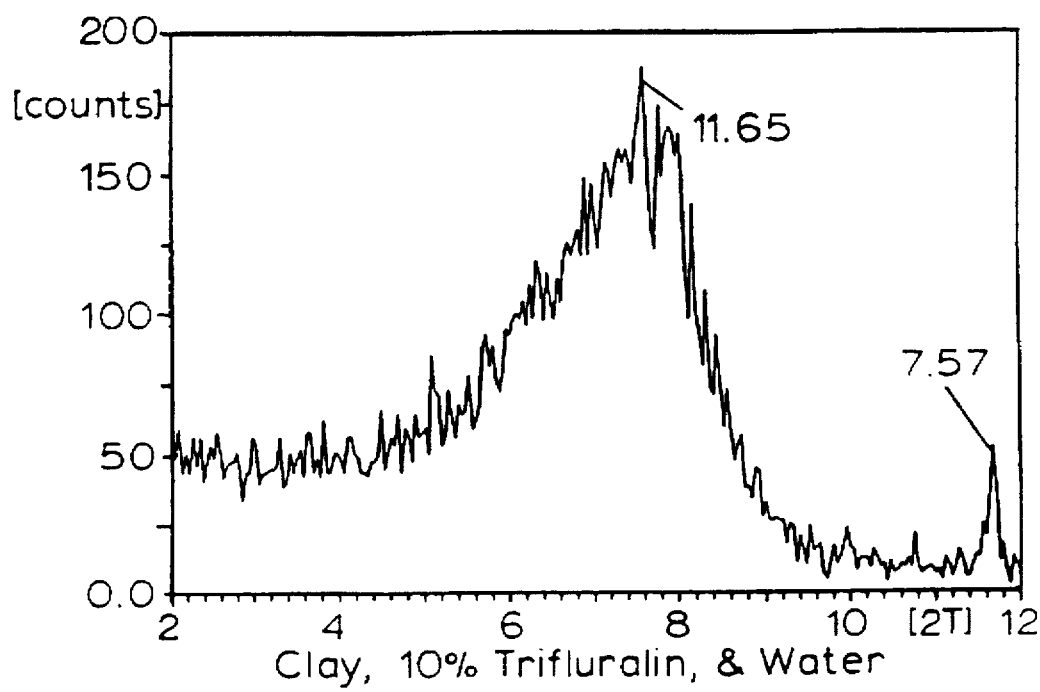
Figure 30B:
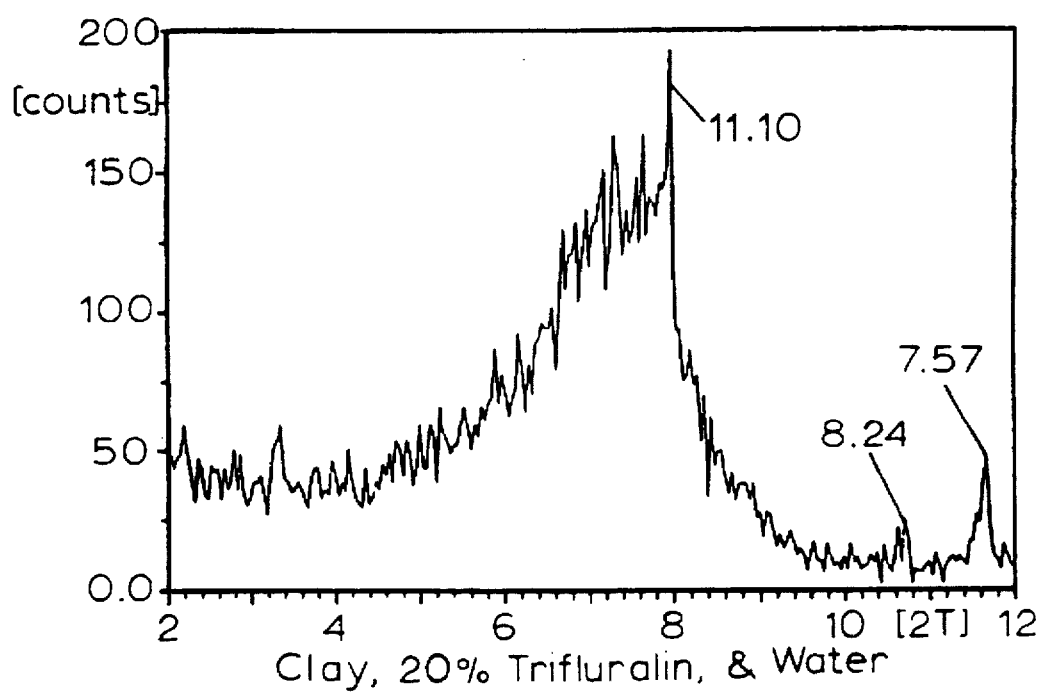
Figure 30C:
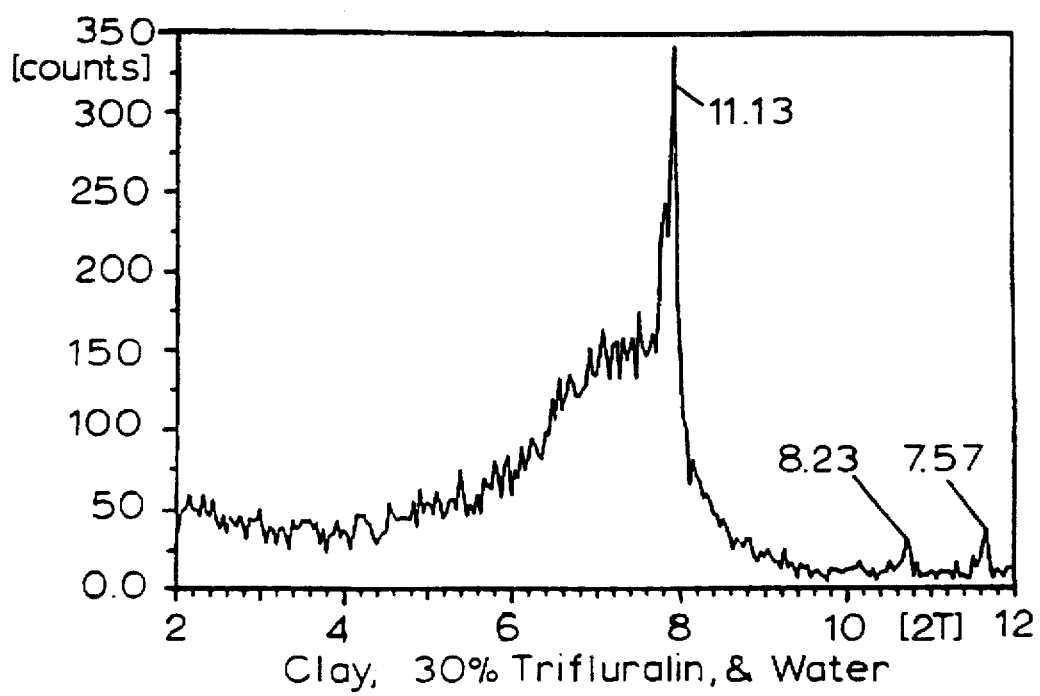
Figure 30D:
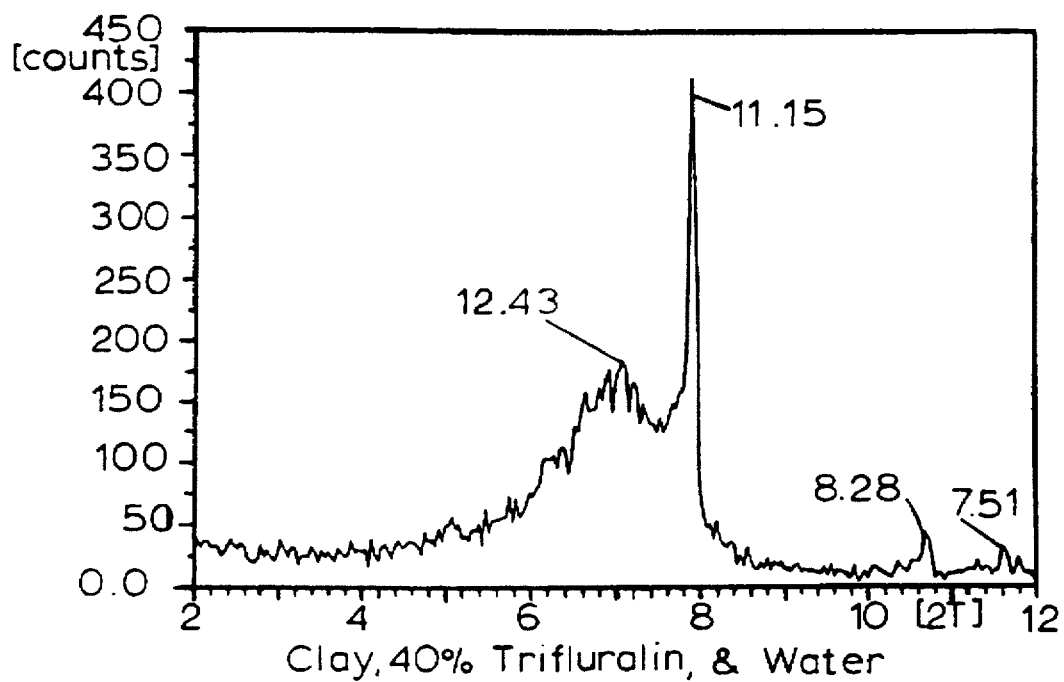

The x-ray diffraction patterns show that a minor portion of the trifluralin was intercalated, i.e., the relatively small peak at 19.51 Å and the large trifluralin peak at 11.21 Å in FIG. 25. A majority of the trifluralin, therefore, merely surface coated the clay granules. FIG. 26 further illustrates that the majority of the trifluralin surface coated the granules because the trifluralin sublimed during drying to yield essentially nonintercalated clay, i.e., periodicity of 12.46. Using an increased amount of water when using a granular clay would overcome this difficulty.

EXAMPLE 12c 200 g Belle Yellow clay (powder)

20 g PVA (powder mixed dry in clay)

94 g Trifluralin 23.5 g isopropyl alcohol 115 g Deionized water (normal pH)

Example 12c used a combination of isopropyl alcohol and PVA to activate the clay. Example #10D was similar to Example 12c, except in Example #10D only 88 g of water was used and a glycol ether was used instead of isopropyl alcohol. The intercalated products of Examples #10D and 12C differ in appearance only by color, wherein the pesticide of Example 12c is a darker orange color. The intercalated pesticide of Example 12c was dried at 38° C. X-ray diffraction patterns of wet and dry samples of the intercalated pesticide of Example 12c are set forth in FIGS. 27 and 28, which illustrate intercalation and release of trifluralin.

Examples 13a–13d illustrate the effect of adding 10%, 20%, 30%, and 40% trifluralin, by weight, to clay.

EXAMPLE 13a 200 g Belle Yellow clay
22.2 g Trifluralin (10%)
88.8 g Deionized water (normal pH) (40% by weight of clay and trifluralin)

EXAMPLE 13b 200 g Belle Yellow clay
50 g Trifluralin (20%)
87.5 g Deionized water (normal pH) (35% by weight of clay and trifluralin)

EXAMPLE 13c 200 g Belle Yellow clay
86 g Trifluralin (30%)
100 g Deionized water (normal pH) (35% by weight of clay and trifluralin)

EXAMPLES 13d 200 g Belle Yellow clay
133.3 g Trifluralin (40%)
100 g Deionized water (normal pH) (30% by weight of clay and trifluralin).

Examples 13a–13c each were extruded once. Example 13d was extruded twice. The trifluralin was easily melted in the absence of solvents, but tended to crystallize quickly. Example 13a was too wet for easy processing. X-ray diffraction patterns of wet and dry samples of Examples 13a–13d are set forth in FIGS. 29 and 30.

FIGS. 29 and 30 show that trifluralin is intercalated and is released. The large peak at 11.26 Å for Example 13d (i.e., 40% trifluralin) in FIG. 29 shows that excess trifluralin is present, and no further trifluralin can be intercalated into the clay.

As previously stated, the intercalate containing the intercalant pesticide, after drying, can be pelletized to provide a useful pesticide product. Alternatively, the pelletized intercalate can be used as a composition ingredient, and admixed with other solid ingredients to provide a solid pesticide composition. Finally, the intercalate, either as is or after exfoliation, can be dispersed in an organic liquid, to provide a viscous or a gelled pesticide composition. The viscosity of the composition formed by adding the intercalate or exfoliate thereof is dependent upon intercalate loading, as well as a temperature, pH, and water content of the composition.

It is preferred that platelet loading in a liquid carrier is less than about 10%. Platelet particle loadings within the range of about 0.01% to about 40% by weight, preferably about 0.05% to about 20%, more preferably about 0.5% to about 10%, significantly enhances viscosity of a pesticide composition containing a liquid carrier and a layered material having an intercalant pesticide incorporated therein. In general, the amount of platelet particles incorporated into a liquid carrier, such as a polar solvent, e.g., a glycol or polyol, such as glycerol, is less than about 20% by weight of the mixture, and preferably from about 0.01% to about 20% by weight of the pesticide composition mixture, more preferably from about 0.01% to about 10% by weight of the mixture, and most preferably from about 0.01% to about 5% by weight.

When an organic liquid, or solvent, is added to the intercalate or exfoliate thereof, the mixture is mixed until homogenous, and often heated, to form a more viscous gel before cooling to room temperature (i.e., 24° C.) to measure the viscosity (i.e., on a Brookfield viscometer, spindle #4, unless otherwise noted). Mixing a composition at room temperature typically results in a viscosity of about 2,000 to about 3,000 centipoises (cps), wherein heating the composition resulted in viscosities of about 3,500 to about 4,000 centipoises (80° C.) and about 7,000 to about 8,000 centipoises (100° C.), all viscosities being measured at 24° C. Heating to 145° C., then cooling to room temperature, increased the viscosity to about 200,000 to about 600,000 centipoises.

Various organic liquids can be used to provide a viscous, gelled, or thixotropic composition. Preferably, an organic liquid is added to an intercalate made using an intercalant polymer and/or that is exfoliated. Nonlimiting examples of organic solvents that can be used include methanol, isopropyl alcohol, propylene glycol, glycerol, 1-propanol, acetone, ethanol, ethylene glycol, and 1,4-butanediol. An emulsified combination of silicone oil and water also provided a gel. The organic liquid can be used alone, in combination with water, or in combination with other organic liquids.

By increasing the pH substantially outside the range of about 6 to about 10, the viscosity of the composition is increased to provide a thixotropic gel of viscosity 1,500,000 centipoises, at 24° C., without heating. The pH is adjusted by shearing all components, except an acid or base, in a blender for 3 minutes, then adding the acid or base, and shearing for an additional minute.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the process may be varied substantially without departing from the spirit of the invention, and the exclusive use of all modifications which come within the scope of the appended claims is reserved.

What is claimed is:

1. An intercalate, capable of being exfoliated, comprising a swellable layered material and an intercalant pesticide, formed by contacting the layered material, having adjacent platelets of said layered material, with a composition including a first intercalant selected from the group consisting of water; a water-miscible organic solvent; an aqueous solution of a water-soluble intercalant polymer; and a mixture thereof to form an intercalated layered material, and contacting the intercalated layered material with an intercalating composition containing an intercalant pesticide and a pesticide carrier selected from the group consisting of water; a water-miscible organic solvent; and a mixture thereof, said intercalating composition having a pesticide concentration of at least 2% by weight, based on the weight of pesticide, water and organic solvent in the intercalating composition to form the intercalate by sorption and electrostatic complexing of the intercalant pesticide between adjacent spaced layers of the layered material, without prior sorption of an onium ion or silane coupling agent, to expand the spacing between a predominance of the adjacent platelets of the activated layered material to at least about 10 Å, when measured after sorption of the intercalant pesticide and drying to a maximum of 5% by weight water in said intercalate, based on the dry weight of the layered material, said pesticide selected from the group consisting of the following, including salts thereof, esters thereof and mixtures thereof:

allyl alcohol, anilazine, triadimenol, benomyl, benquinox, bunema, captafol, captan, carbendazim, carboxin, chinosol, chloroneb, chlorothalonil, cycloheximide, dazomet, dicloran, dichlofluanid, dichlone, dimethirimol, dinocap, manzeb, dithianon, dodemorph, dodine, drazoxolon, edinfenphos, fenaminosulf, fenapanil, fentiazon, ferbam, folpet, fongarid, guazatine, hymexazol, iprodione, kasugamycin, maneb, 2-methoxyethylmercurychloride chloro (-2-methoxyethyl) mercury, methylthiophenate, metiram, nabam, neo-asozin, o-phenylphenol, phenylmercury acetate, oxycarboxin, parinol, quintozene, phosethyl, piperalin, polyoxin, procymidone, propineb, propazine, propionic acid, prothiocarb, pyracarbolid, pyrazophos, thiabendazole, thiophanate, thiram, tolylfluanid, triadimefon, tridemorph, triforine, triphenyltin acetate, validamycin A, vinclozolin, vondozeb, zineb, chloranil, ziram, 8-quinolinol, sulfallate, metam, glyodin, 2,6-bis [dimethylaminomethyl]cyclohexanone, hexachloroacetone, bromoacetyl bromide, picloram, benalaxyl, blasticidin S, bupirimate, buthiobate, chinomethionate, chlozolinate, cymoxanil, cyproconazole, dithianon, ethirimol, etridazole, fenarimol, fenpiclonil, fenpropidin, fenpropimorph, fentin, flusilazole, flutriafol, flutolanl, fuberidazole, furalaxyl, imazalil, imibenconazole, iprobenphos, isoprothiolane, mancozeb, mepronil, methfuroxam, metsulfovax, myclobutanil, nuarimol, ofurace, oxadixyl, polyoxin B, polyoxin D, prochloraz, procymidone, propiconazole, pyroquilon, quintozene, tebucanazole, tetraconazole, triarimol, tricyclazole, triforine, acifluorfen, alachlor, alanap, alloxydim, ametryn, amitrol, asulam, atrazine, azide, barban, benazolin, benefin, bensulide, bentazone, benthiocarb, benzoylprop, benzthiazuron, bifenox, acetochlor, acrolein, benazolin, buthidazole, allidochlor, bromacil, bromofenoxin, bromoxynil, butachlor, butralin, buturon, butylate, chlometoxynil, chloramben, chlorbromuron, chlorfenprop, chloridazon, chlorotoluron, chloroxuron, chlorpropham, chlorthiamid, 2,4,6-trichlorophenyl-4-nitrophenyl ether, crotoxyphos, cycloate, cyprazine, 2,4-dichlorophenoxyacetic acid, dalapon, 4-(2,4-dichlorophenoxy) butyric acid, dimethyl tetrachloroterephthalate, a mixture of tris (2,4-dichlorophenoxyethyl) phosphite, and bis (2,4-dichlorophenoxyethyl) phosphite, desmedipham, 2-(2, 4-dichlorophenoxy)propionic acid, desmetryn, diallate, dicamba, dichlobenil, dichlorprop, diethatyl, difenoxuron, diclofop, dimexano, dinitramine, dinoseb, dinoterb, diphenamid, dipropetryn, diquat, diuron, endothall, erbon, ethofumesate, fenac, fenuron, flamprop, fluchloralin, S-ethyl dipropylthiocarbamate, pentachlorophenol, fluometuron, fluorodifen, flurecol, glyphosate, glyphosine, hexazinone, ioxynil, isopropalin, isoproturon, karbutilate, lenacil, linuron, mecoprop, medinoterb, methazole, methoprotryne, metobromuron, metolachlor, metoxuron, metribuzin, molinate, monalide, monlinuron, monuron, naptalam, neburon, nitralin, nitrofen, norea, norflurazon, oryzalin, oxadiazon, paraquat, pebulate, penoxalin, perfluidone, phenisopham, phenmedipham, picloram, procyazine, profluralin, prometon, prometryn, pronamide, propachlor, propanil, propazine, propham, secbumeton, siduron, silvex, simazine, swep, 2,4,5-trichlorophenoxy acetic acid, 2,3,6-trichlorobenzoic acid, tebuthiuron, terbacil, terbumeton, terbuthylazine, terbutol, terbutryn, tetrafluoron, triallate, trietazine, trifluralin, vernolate, 1-naphthaleneacetic acid, N-m-tolylphthalamic acid, ethyl-1-naphthalene acetate, chloroacetic acid, trichloroacetic acid, p-chloromandelic acid, dimethylamino-2,3,5-triiodobenzoate, 2-naphthoxyacetic acid, phenoxyacetic acid, 2-phenoxypropionic acid, o-chlorophenoxy acetic acid, p-chlorophenoxy acetic acid, 4-chloro-2-methyl phenoxyacetic acid, silvex, 4-[(4-chloro-o-tolyl)oxy]butyric acid, p-bromophenoxy acetic acid, dimethylamino-4[2,4-dichlorophenoxy]butyrate, 3-indolebutyric acid, 3-indoleacetic acid, 3-indolepropionic acid, gibberellic acid, N,N-dimethylsuccinamic acid, 2-furanacrylic acid, endothal, 1-naphthaleneacetamide, allidochlor, N-methyl-N-1-naphthylacetamide, N-1-naphthyl acetamide, 2-[3-chlorophenoxy]propionamide, noruron, siduron, metobromuron, terbacil, chloroxuron, aminotriazole, cyanazine, chlorflurenol, chlorsulfuron, cyanazine, cyometrinil, 3,6-dichloropicolinic acid, dichlofop, difenzoquat, diphenamid, ethaflualin, ethepon, flurazole, flurenol, fluridone, fosamine, isouron, mefluidide, 1,8-naphthalic anhydride, napropamide, pyrazon, thoibencarb, anilazine, diphenatrile, N-[2,4-dichlorophenoxyl)acetyl-DL-methionine, daminozide, pyrazon, ethoxyquin, propham, S-carboxymethyl-N,N-dimethyldicarbamate, phosphan, merphos, ethephon, tricamba, amiben, glufosinate, indole-3-butyric acid, β-naphthoxyacetic acid, triclopyr, 9-undecylenic acid, oxyflurofen, dinitrocresol, flurtamone, diflufenican, difunon, fomesafen, clethodim, sethoxydim, haloxyfop, tralkoxydim, fenoxaprop, fluazifop, phaseolotoxin, rhizobitoxine, barban, ethephon, tetcyclacis, mepiquat chloride, ancymidol, uniconzaole, paclobutrazol, diquatop, pendimethalin, karbutilate, asulam, clopyralid, fluroxypyr, chlorimuron, chlorsulfuron, metsulfuron, buthidazole, imazamethabenz, imazapyr, imazaquin, imazethapry, isoxaben, cinmethylin, ethofumesate, acephate, aldicarb, aldoxycarb, aldrin, d-trans allethrin, allyxycarb, aminocarb, amitraz, azinphos, azinphos, azocyclotin, azothoate, bendiocarb, benzomate, binapacryl, bomyl, 2-sec-butylphenyl N-methylcarbamate, bromophos, bromophos-ethyl, bromopropylate, butacarb, butocarboxim, chlordane, chlordecone, heptachlor, lindane, methoxychlor, toxaphene, butoxicarboxim, carbaryl, carbofuran, carbophenothion, cartap, chloridimeform, chlorfenethol, chlorfenvinphos, chlormephos, chlorobenzilate, chloropropylate, chlorphoxim, chlorpyrifos, chlorthiophos, coumaphos, 2-chlorophenyl-N-methylcarbamate, crufomate, cryolite, cyanofenphos, cyanophos, cyhexatin, cypermethrin, cythioate, dichloro diphenyl trichloroethane, 2,2-dichlorovinyl o,o-dimethyl phosphate, demeton, demeton-S-methyl, dialifor, diazinon, dicofol, dicrotophos, dieldrin, dienochlor, diflubenzuron, dimefox, dimethoate, dimethrin, dinobuton, dioxacarb, dioxathion, disulfoton, 2-methyl-4,6-dinitrophenol, d-phenothrin, endosulfan, enfrin, o-ethyl o(4-nitrophenyl) phenylphosphonothioate, ethyl p-nitrophenyl thionobenzenephosphonate, ethiofencarb, ethion, ethoate, ethoprop, etrimfos, famphur, feributatin-oxide, fenitrothion, fenson, fensulfothion, fenthion, fenvalerate, fonofos, formetanate hydrochloride, formothion, fosthietan, hydroprene, isofenphos, isoxathion, isothioate, malathion, mecarbam, mecarphon, menazon, meobal, mephosfolan, mercaptodimethur, methamidophos, methidathion, methomyl, methoprene, isoprocarb, mirex, monocrotophos, m-tolyl-N-methylcarbamate, naled, nicotine, omethoate, oxamyl, oxydemeton-methyl, oxydisulfoton, parathion, permethrin, phenthoate, phorate, phosalone, phosmet, phosphamidon, phoxim, pirimicarb, pirimiphos, plifenate, profenofos, promecarb, propargite, propetamphos, propoxur, prothiophos, prothoate, quinalphos, resmethrin, ronnel, ryania, salithion, schradan, sulfotepp, sulprofos, temephos, tetraethyl diphosphate, terbufos, tetrachlorvinphos, tetradifon, tetramethrin, tetrasul, thiocyclamhydrogenoxalate, thiometon, thioquinox, triazophos, trichloronate, trichloron, vamidothion, melvinphos, trichlorofon, O,O-dimethyl phosphorochloriodothioate, methyl parathion, demeton O, dicapthon, O,O-diethylphosphorochloridothioate, propham, matacil, a mixture of m[1-ethylpropyl] phenylmethylcarbamate and m[1-ethylpropyl] phenylmethylcarbamate, pyrethrum, benzyl thiocyanate, rotenone, eugenol, aminozide, ancymidol, anthraquinone, brodifacoum, bromadiolone, butoxy polypropylene glycol, carbon tetrachloride, chloflurecol-methyl ester, chlormequat chloride, chlorophacinone, chloropicrin, chlorphonium, chlonitralid, coumachlor, coumafuryl, crimidine, cyoxmetril, deet, diazacosterol hydrochloride, dibutyl phthalate, ethyl hexanediol, dichlofenthion, difenacoum, dikegulac sodium, diphenylamine, ethephone, fenamiphos, fluoroacetamide, glyoxime, gossyplure, heliotropin acetal, kinoprene, maleic hydrazine, metaldehyde, metam-sodium, naphthalene acetamide, 1-naphthaleneacetic acid, nitrapyrin, pyriminal, scillirosid, sesamex, sulfoxide, trifenmorph, triprene, and warfarin, and wherein said intercalant polymer, when included in the frist intercalant composition, is selected from the following, salts thereof and mixtures thereof:

polyvinylpyrrolidone having a repeating structure (I):

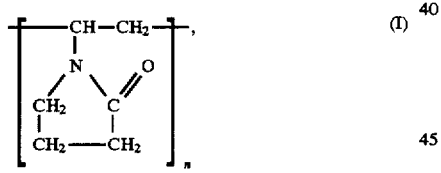

wherein n is in the range of 2 to about 1500; metal salts of polyvinylpyrrolidone; hydrolyzed polyvinylpyrrolidone of structure (II):

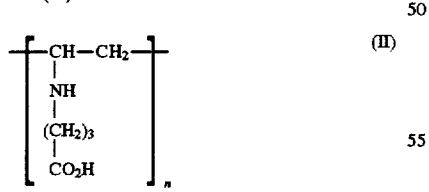

wherein n is in the range of 2 to about 1500; copolymers of vinylpyrrolidone and a vinyl amide of γ-amine butyric acid; polyvinyl alcohol having 5% or less acetyl groups; polyvinyl alcohol having 1% or less acetyl groups; polyacrylic acid polymers; polyacrylic acid copolymers; partially or fully neutralized salts of polyacrylic acid polymers and polyacrylic acid copolymers; poly(methacrylic acid); poly(methacrylamide); poly(N,N-dimethylacrylamide); poly(N-isopropylacrylamide); poly(N-acetamidoacrylamide); poly(N-acetmidomethacrylamide); acrylic interpolymers of polyacrylic acid with poly(methacrylic acid), polyacrylic acid with poly(methacrylamide), and polyacrylic acid with methacrylic acid, polyvinyloxazolidone; polyvinylmethyloxazolidone; polyoxypropylene-polyoxyethylene block polymers having one of the following structures:

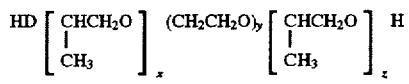

and

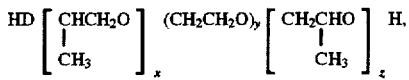

wherein x and z are each an integer in the range of about 4 to about 30, and y is an integer in the range of about 4 to about 100; polyacrylamide; copolymers of acrylamide; acrylamide/sodium acrylate copolymers; acrylate/acrylamide copolymers; acrylate/ammonium methacrylate copolymers; acrylate/diacetoneacrylamide copolymers; acrylic/acrylate copolymers; adipic acid/dimethylaminohydroxypropyl diethylenetriamine copolymers; ammonium acrylate copolymers; ammonium styrene/acrylate copolymers; ammonium vinyl acetate/acrylate copolymers; aminomethylpropanol acrylate/diacetoneacrylamide copolymers; aminomethylpropanediol acrylate/diacetoneacrylamide copolymers; butyl benzoic acid/phthalic anhydride/trimethylolethane copolymers; cornstarch/acrylamide/sodium acrylate copolymers; diethylene glycolamine/epichlorohydrin/piperazine copolymers; dodecanedioic acid/cetearyl alcohol/glycol copolymers; ethylene/vinyl alcohol copolymers; ethyl esters of polyethylenimines; isopropyl ester of methyl vinyl ether/maleic anhydride copolymers; melamine/formaldehyde resin; methacryloyl ethyl betaine/methacrylate copolymers; methoxyethylene glycol/dodecyl glycol copolymers; octadecene/maleic anhydride copolymers; octylacrylamide/acrylate/butylaminoethyl methacrylate copolymers; octylacrylamide/acrylate copolymers; polyethylene glycol/dodecyl glycol copolymers; polyethyleneimine; phthalic anhydride/glycerin/glycidyl decanoate copolymers; metal salts of acrylic and polyacrylic acid; polyaminopropyl biguanide; polymeric quaternary ammonium salts; polyvinyl imidazolinium acetate; potassium polyacrylate; sodium polyacrylate; metal salts of methyl vinyl ether/maleic anhydride copolymers; vinylpyrrolidone/eicosene copolymers; vinylpyrrolidone/ethyl methacrylate/methacrylic acid copolymers; vinylpyrrolidone/hexadecene copolymers; vinylpyrrolidone/vinyl acetate copolymers; polyvinylpyrrolidone/vinyl acetate/itaconic acid copolymers; sodium acrylate/vinyl alcohol copolymers; $C_4$-$C_{12}$ metal salts of olefin/maleic acid copolymers; sodium polymethacrylate; sodium polystyrene sulfonate; sodium styrene/acrylate/polyethylene glycol-10 dimaleate copolymers; water-soluble esters and ethers of cellulose; sodium styrene/polyethylene glycol-10 maleate/nonoxynol-10 maleate/acrylate copolymers; starch/acrylate/acrylamide copolymers; styrene/acrylamide copolymers; styrene/acrylate/ammonium methacrylate copolymers; styrene/maleic anhydride copolymers; styrene/polyvinyloxazolidone copolymers; sucrose benzoate/sucrose acetate isobutyrate/butyl benzyl phthalate copolymers; sucrose benzoate/sucrose acetate isobutyrate/butyl benzylphthalate/methyl methacrylate copolymers; urea formaldehyde polymers; urea/melamine/formaldehyde polymers; vinyl acetate/crotonic acid copolymers; vinyl alcohol copolymers; and polysaccharides.

2. A pesticide composition comprising the intercalate of claim 1, in a concentration of about 0.05% to about 99.5% by weight, and an inert carrier.

3. The pesticide composition of claim 2 wherein the inert carrier is a solid selected from the group consisting of calcined clay, ground corn cobs, sawdust, silica, wood chips, sand, and mixtures thereof.

4. A pesticide composition comprising an intercalate, together with an organic solvent, said intercalate formed by contacting a layered material, having a moisture content of at least about 4% by weight, with a composition comprising an aqueous solution of an intercalant polymer, said intercalant polymer having a concentration of at least 2% by weight based on the total weight of water and intercalant polymer in said composition, to form a polymer intercalated layered material by sorption and complexing of the intercalant polymer between adjacent spaced layers of the layered material to expand the spacing between a predominance of the adjacent platelets of said layered material to at least about 10 Å, when measured after sorption of the intercalant polymer and drying to a maximum of 5% by weight water, based on the dry weight of the layered material; and then contacting the polymer intercalated layered material with an intercalating composition comprising an intercalant pesticide and a carrier for said intercalant pesticide to provide the intercalate, wherein the intercalant pesticide is sorbed and electrostatically complexed between adjacent spaced layers of the layered material, said pesticide selected from the group consisting of the following, including salts thereof, esters thereof and mixtures thereof:

allyl alcohol, anilazine, triadimenol, benomyl, benquinox, bunema, captafol, captan, carbendazim, carboxin, chinosol, chloroneb, chlorothalonil, cycloheximide, dazomet, dicloran, dichlofluanid, dichlone, dimethirimol, dinocap, manzeb, dithianon, dodemorph, dodine, drazoxolon, edinfenphos, fenaminosulf, fenapanil, fentiazon, ferbam, folpet, fongarid, guazatine, hymexazol, iprodione, kasugamycin, maneb, 2-methoxyethylmercurychloride chloro(-2-methoxyethyl) mercury, methylthiophenate, metiram, nabam, neo-asozin, o-phenylphenol, phenylmercury acetate, oxycarboxin, parinol, quintozene, phosethyl, piperalin, polyoxin, procymidone, propineb, propazine, propionic acid, prothiocarb, pyracarbolid, pyrazophos, thiabendazole, thiophanate, thiram, tolylfluanid, triadimefon, tridemorph, triforine, triphenyltin acetate, validamycin A, vinclozolin, vondozeb, zineb, chloranil, ziram, 8-quinolinol, sulfallate, metam, glyodin, 2,6-bis [dimethylaminomethyl]cyclohexanone, hexachloroacetone, bromoacetyl bromide, picloram, benalaxyl, blasticidin S, bupirimate, buthiobate, chinomethionate, chlozolinate, cymoxanil, cyproconazole, dithianon, ethirimol, etridazole, fenarimol, fenpiclonil, fenpropidin, fenpropimorph, fentin, flusilazole, flutriafol, flutolanl, fuberidazole, furalaxyl, imazalil, imibenconazole, iprobenphos, isoprothiolane, mancozeb, mepronil, methfuroxam, metsulfovax, myclobutanil, nuarimol, ofurace, oxadixyl, polyoxin B, polyoxin D, prochloraz, procymidone, propiconazole, pyroquilon, quintozene, tebucanazole, tetraconazole, triarimol, tricyclazole, triforine, acifluorfen, alachlor, alanap, alloxydim, ametryn, amitrol, asulam, atrazine, azide, barban, benazolin, benefin, bensulide, bentazone, benthiocarb, benzoylprop, benzthiazuron, bifenox, acetochlor, acrolein, benazolin, buthidazole, allidochlor, bromacil, bromofenoxin, bromoxynil, butachlor, butralin, buturon, burylate, chlometoxynil, chloramben, chlorbromuron, chlorfenprop, chloridazon, chlorotoluron, chloroxuron, chlorpropham, chlorthiamid, 2,4,6-trichlorophenyl-4-nitrophenyl ether, crotoxyphos, cycloate, cyprazine, 2,4-dichlorophenoxyacetic acid, dalapon, 4-(2,4-dichlorophenoxy) butyric acid, dimethyl tetrachloroterephthalate, a mixture of tris (2,4-dichlorophenoxyethyl) phosphite, and bis dichlorophenoxyethyl) phosphite, desmedipham, 2-(2, 4-dichlorophenoxy)propionic acid, desmetryn, diallate, dicamba, dichlobenil, dichlorprop, diethatyl, difenoxuron, diclofop, dimexano, dinitramine, dinoseb, dinoterb, diphenamid, dipropetryn, diquat, diuron, endothall, erbon, ethofumesate, fenac, fenuron, flamprop, fluchloralin, S-ethyl dipropylthiocarbamate, pentachlorophenol, fluometuron, fluorodifen, flurecol, glyphosate, glyphosine, hexazinone, ioxynil, isopropalin, isoproturon, karbutilate, lenacil, linuron, mecoprop, medinoterb, methazole, methoprotryne, metobromuron, metolachlor, metoxuron, metribuzin, molinate, monalide, monlinuron, monuron, naptalam, neburon, nitralin, nitrofen, norea, norflurazon, oryzalin, oxadiazon, paraquat, pebulate, penoxalin, perfluidone, phenisopham, phenmedipham, picloram, procyazine, profluralin, prometon, prometryn, pronamide, propachlor, propanil, propazine, propham, secbumeton, siduron, silvex, simazine, swep, 2,4,5-trichlorophenoxy acetic acid, 2,3,6-trichlorobenzoic acid, tebuthiuron, terbacil, terbumeton, terbuthylazine, terbutol, terbutryn, tetrafluoron, triallate, trietazine, trifluralin, vernolate, 1-naphthaleneacetic acid, N-m-tolylphthalamic acid, ethyl-1-naphthalene acetate, chloroacetic acid, trichloroacetic acid, p-chloromandelic acid, dimethylamino-2,3,5-triiodobenzoate, 2-naphthoxyacetic acid, phenoxyacetic acid, 2-phenoxypropionic acid, o-chlorophenoxy acetic acid, p-chlorophenoxy acetic acid, 4-chloro-2-methyl phenoxyacetic acid, silvex, 4-[(4-chloro-o-tolyl)oxy]butyric acid, p-bromophenoxy acetic acid, dimethylamino-4[2,4-dichlorophenoxy]butryate, 3-indolebutyric acid, 3-indoleacetic acid, 3-indolepropionic acid, gibberellic acid, N,N-dimethylsuccinamic acid, 2-furanacrylic acid, endothal, 1-naphthaleneacetamide, allidochlor, N-methyl-N-1-naphthylacetamide, N-1-naphthyl acetamide, 2-[3-chlorophenoxy]propionamide, noruron, siduron, metobromuron, terbacil, chloroxuron, aminotriazole, cyanazine, chlorflurenol, chlorsulfuron, cyanazine, cyometrinil, 3,6-dichloropicolinic acid, dichlofop, difenzoquat, diphenamid, ethaflualin, ethepon, flurazole, flurenol, fluridone, fosamine, isouron, mefluidide, 1,8-naphthalic anhydride, napropamide, pyrazon, thoibencarb, anilazine, diphenatrile, N-[2,4-dichlorophenoxyl)acetyl-DL-methionine, daminozide, pyrazon, ethoxyquin, propham, S-carboxymethyl-N,N-dimethyldicarbamate, phosphan, merphos, ethephon, tricamba, amiben, glufosinate, indole-3-butyric acid, β-naphthoxyacetic acid, triclopyr, 9-undecylenic acid, oxyflurofen, dinitrocresol, flurtamone, diflufenican, difunon, fomesafen, clethodim, sethoxydim, haloxyfop, tralkoxydim, fenoxaprop, fluazifop, phaseolotoxin, rhizobitoxine, barban, ethephon, tetcyclacis, mepiquat chloride, ancymidol, uniconzaole, paclobutrazol, diquatop, pendimethalin, karbutilate, asulam, clopyralid, fluroxypyr, chlorimuron, chlorsulfuron, metsulfuron, buthidazole, imazamethabenz, imazapyr, imazaquin, imazethapry, isoxaben, cinmethylin, ethofumesate, acephate, aldicarb, aldoxycarb, aldrin, d-trans allethrin, allyxycarb, aminocarb, amitraz, azinphos, azinphos, azocyclotin, azothoate, bendiocarb, benzomate, binapacryl, bomyl, 2-sec-butylphenyl N-methylcarbamate, bromophos, bromophos-ethyl, bromopropylate, butacarb, butocarboxim, chlordane, chlordecone, heptachlor, lindane, methoxychlor, toxaphene, butoxicarboxim, carbaryl, carbofuran, carbophenothion, cartap, chloridimeform, chlorfenethol, chlorfenvinphos, chlormephos, chlorobenzilate, chloropropylate, chlorphoxim, chlorpyrifos, chlorthiophos, coumaphos, 2-chlorophenyl-N-methylcarbamate, crufomate, cryolite, cyanofenphos, cyanophos, cyhexatin, cypermethrin, cythioate, dichloro diphenyl trichloroethane, 2,2-dichlorovinyl o,o-dimethyl phosphate, demeton, demeton-S-methyl, dialifor, diazinon, dicofol, dicrotophos, dieldrin, dienochlor, diflubenzuron, dimefox, dimethoate, dimethrin, dinobuton, dioxacarb, dioxathion, disulfoton, 2-methyl-4,6-dinitrophenol, d-phenothrin, endosulfan, enfrin, o-ethyl o(4-nitrophenyl) phenylphosphonothioate, ethyl p-nitrophenyl thionobenzenephosphonate, ethiofencarb, ethion, ethoate, ethoprop, etrimfos, famphur, fenbutatin-oxide, fenitrothion, fenson, fensulfothion, fenthion, fenvalerate, fonofos, formetanate hydrochloride, formothion, fosthietan, hydroprene, isofenphos, isoxathion, isothioate, malathion, mecarbam, mecarphon, menazon, meobal, mephosfolan, mercaptodimethur, methamidophos, methidathion, methomyl, methoprene, isoprocarb, mirex, monocrotophos, m-tolyl-N-methylcarbamate, naled, nicotine, omethoate, oxamyl, oxydemeton-methyl, oxydisulfoton, parathion, permethrin, phenthoate, phorate, phosalone, phosmet, phosphamidon, phoxim, pirimicarb, pirimiphos, plifenate, profenofos, promecarb, propargite, propetamphos, propoxur, prothiophos, prothoate, quinalphos, resmethrin, ronnel, ryania, salithion, schradan, sulfotepp, sulprofos, temephos, tetraethyl diphosphate, terbufos, tetrachlorvinphos, tetradifon, tetramethrin, tetrasul, thiocyclamhydrogenoxalate, thiometon, thioquinox, triazophos, trichloronate, trichloron, vamidothion, melvinphos, trichlorofon, O,O-dimethyl phosphorochloriodothioate, methyl parathion, demeton O, dicapthon, O,O-diethylphosphorochloridothioate, propham, matacil, a mixture of m[1-ethylpropyl] phenylmethylcarbamate and m[1-ethylpropyl] phenylmethylcarbarnate, pyrethrum, benzyl thiocyanate, rotenone, eugenol, aminozide, ancymidol, anthraquinone, brodifacoum, bromadiolone, butoxy polypropylene glycol, carbon tetrachloride, chloflurecolmethyl ester, chlormequat chloride, chlorophacinone, chloropicrin, chlorphonium, chlonitralid, coumachlor, coumafuryl, crimidine, cyoxmetril, deet, diazacosterol hydrochloride, dibutyl phthalate, ethyl hexanediol, dichlofenthion, difenacoum, dikegulac sodium, diphenylamine, ethephone, fenamiphos, fluoroacetamide, glyoxime, gossyplure, heliotropin acetal, kinoprene, maleic hydrazine, metaldehyde, metam-sodium, naphthalene acetamide, 1-naphthaleneacetic acid, nitrapyrin, pyriminal, scillirosid, sesamex, sulfoxide, trifenmorph, triprene, and warfarin; and wherein said intercalant polymer is selected from the group consisting of the following, salts thereof and mixtures thereof:

polyvinylpyrrolidone having a repeating structure (I):

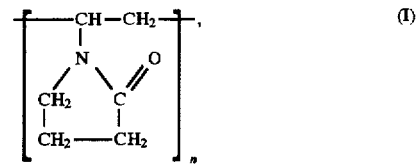

wherein n is in the range of 2 to about 1500; metal salts of polyvinylpyrrolidone; hydrolyzed polyvinylpyrrolidone of structure (II):

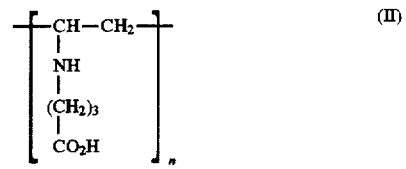

wherein n is in the range of 2 to about 1500; copolymers of vinylpyrrolidone and a vinyl amide of γ-amine butyric acid; polyvinyl alcohol having 5% or less acetyl groups; polyvinyl alcohol having 1% or less acetyl groups; polyacrylic acid polymers; polyacrylic acid copolymers; partially or fully neutralized salts of polyacrylic acid polymers and polyacrylic acid copolymers; poly(methacrylic acid); poly(methacrylamide); poly(N, N-dimethylacrylamide); poly(N-isopropylacrylamide); poly(N-acetamidoacrylamide); poly(N-acetmidomethacrylamide); acrylic interpolymers of polyacrylic acid with poly(methacrylic acid), polyacrylic acid with poly(methacrylamide), and polyacrylic acid with methacrylic acid, polyvinyloxazolidone; polyvinylmethyloxazolidone; polyoxypropylene-polyoxyethylene block polymers having one of the following structures:

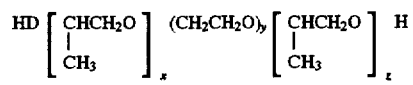

and

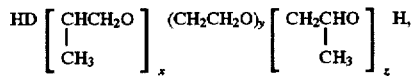

wherein x and z are each an integer in the range of about 4 to about 30, and y is an integer in the range of about 4 to about 100; polyacrylamide; copolymers of acrylamide; acrylamide/sodium acrylate copolymers; acrylate/acrylamide copolymers; acrylate/ammonium methacrylate copolymers; acrylate/diacetoneacrylamide copolymers; acrylic/acrylate copolymers; adipic acid/dimethylaminohydroxypropyl diethylenetriamine copolymers; ammonium acrylate copolymers; ammonium styrene/acrylate copolymers; ammonium vinyl acetate/acrylate copolymers; aminomethylpropanol acrylate/diacetoneacrylamide copolymers; aminomethylpropanediol acrylate/diacetoneacrylamide copolymers; butyl benzoic acid/phthalic anhydride/trimethylolethane copolymers; cornstarch/acrylamide/sodium acrylate copolymers; diethylene glycolamine/epichlorohydrin/piperazine copolymers; dodecanedioic acid/cetearyl alcohol/glycol copolymers; ethylene/vinyl alcohol copolymers; ethyl esters of polyethylenimines; isopropyl ester of methyl vinyl ether/maleic anhydride copolymers; melamine/formaldehyde resin; methacryloyl ethyl betaine/methacrylate copolymers; methoxyethylene glycol/dodecyl glycol copolymers; octadecene/maleic anhydride copolymers; octylacrylamide/acrylate/butylaminoethyl methacrylate copolymers; octylacrylamide/acrylate copolymers; polyethylene glycol/dodecyl glycol copolymers; polyethyleneimine; phthalic anhydride/glycerin/glycidyl decanoate copolymers; metal salts of acrylic and polyacrylic acid; polyaminopropyl biguanide; polymeric quaternary ammonium salts; polyvinyl imidazolinium acetate; potassium polyacrylate; sodium polyacrylate; metal salts of methyl vinyl ether/maleic anhydride copolymers; vinylpyrrolidone/eicosene copolymers; vinylpyrrolidone/ethyl methacrylate/methacrylic acid copolymers; vinylpyrrolidone/hexadecene copolymers; vinylpyrrolidone/vinyl acetate copolymers; polyvinylpyrrolidone/vinyl acetate/itaconic acid copolymers; sodium acrylate/vinyl alcohol copolymers; $C_4$–$C_{12}$ metal salts of olefin/maleic acid copolymers; sodium polymethacrylate; sodium polystyrene sulfonate; sodium styrene/acrylate/polyethylene glycol-10 dimaleate copolymers; water-soluble esters and ethers of cellulose; sodium styrene/polyethylene glycol-10 maleate/nonoxynol-10 maleate/acrylate copolymers; starch/acrylate/acrylamide copolymers; styrene/acrylamide copolymers; styrene/acrylate/ammonium methacrylate copolymers; styrene/maleic anhydride copolymers; styrene/polyvinyloxazolidine copolymers; sucrose benzoate/sucrose acetate isobutyrate/butyl benzyl phthalate copolymers; sucrose benzoate/sucrose acetate isobutyrate/butyl benzylphthalate/methyl methacrylate copolymers; urea formaldehyde polymers; urea/melamine/formaldehyde polymers; vinyl acetate/crotonic acid copolymers; vinyl alcohol copolymers; and polysaccharides.

5. The intercalate of claim 1 wherein the first intercalant comprises water.

6. The intercalate of claim 5 wherein the first intercalant comprises water and an organic solvent.

7. The intercalate of claim 1 wherein the first intercalant is an aqueous solution of a water-soluble intercalant polymer.

8. The intercalate of claim 1 wherein the concentration of intercalant pesticide is about 0.01% to about 40% by weight, based on the dry weight of the layered material.

9. The intercalate of claim 8 wherein the concentration of intercalant pesticide is about 0.1% to about 35% by weight, based on the dry weight of the layered material.

10. The intercalate of claim 9 wherein the concentration of intercalant pesticide is about 5% to about 30% by weight, based on the dry weight of the layered material.

11. The intercalate of claim 1 wherein the concentration of intercalant pesticide is at least about 8% by weight, based on the dry weight of the layered material.

12. The intercalate of claim 7 wherein the concentration of the intercalant polymer is at least about 16% by weight, based on the dry weight of the layered material, to achieve spacing between adjacent platelets of said activated layered material of at least about 10 Å.

13. The intercalate of claim 7 wherein the concentration of the intercalant polymer is at least about 35% by weight, based on the dry weight of the layered material, to achieve spacing between adjacent platelets of said activated layered material of at least about 20 Å.

14. The intercalate of claim 7 wherein the concentration of the intercalant polymer is at least about 55% by weight, based on the dry weight of the layered material, to achieve spacing between adjacent platelets of said activated layered material of at least about 30 Å.

15. The intercalate of claim 1 wherein the intercalant pesticide contains at least one polar moiety.

16. The intercalate of claim 6 wherein the intercalant pesticide lacks a polar moiety.

17. The intercalate of claim 15 wherein the polar moiety is selected from the group consisting of a carboxylic acid, a salt of a carboxylic acid, an ester, an amide, an anhydride, a ketone, an aldehyde, cyano, nitro, thiocarbamate, amino, carbamic, phosphate, thiophosphate, sulfoxide, carboximide, urea, sulfone, phosphorothioate, phosphorodithioate, thiourea, dithiocarbamate, phosphoramidodithioate, methylsulfonyl, phosphonate, sulfamide, phosphoramide, sulfonate, dithiocarbonate, hydroxyl, sulfate, sulfinate, sulfamate, and phosphinate.

18. The intercalate of claim 15 wherein the polar moiety has two adjacent atoms that are covalently bonded, and the two atoms have a difference in electronegativity of at least about 0.5 electronegativity units.

19. The intercalate of claim 1 wherein the pesticide is selected from the group consisting of fungicides, insecticides, herbicides, acaricides, nematocides, rodenticides, miticides, repellents, growth regulators, larvacides, and mixtures thereof.

20. The intercalate of claim 1 wherein the pesticide comprises an herbicide.

21. The intercalate of claim 20 wherein the herbicide is selected from the group consisting of trifluralin, 2,4-dichlorophenoxyacetic acid, dicamba, and mixtures thereof.

22. The intercalate of claim 1 wherein the pesticide comprises an insecticide.

23. The intercalate of claim 22 wherein the insecticide is chlorpyrifos.

24. The intercalate of claim 7 wherein the weight ratio of intercalant polymer to layered material is at least 1:20.

25. The intercalate of claim 7 wherein the weight ratio of intercalant polymer to layered material is at least 1:4.

26. The intercalate of claim 1 wherein the weight ratio of intercalant pesticide to layered material is at least about 1:2.

27. The intercalate of claim 7 wherein the concentration of intercalant polymer is at least about 0.1% by weight, based on the weight of water and intercalant polymer.

28. The intercalate of claim 27 wherein the concentration of intercalant polymer is at least about 2% by weight.

29. The intercalate of claim 7 wherein the concentration of intercalant polymer in said intercalate is at least about 2% by weight, based on the dry weight of layered material, and wherein said intercalant polymer has a functionality selected from the group consisting of an aromatic ring, a carboxyl, a hydroxyl, a carbonyl, an ether, an ester, an amine, an amide, an SOx, a POx, wherein x=2, 3, or 4, and mixtures thereof.

30. The intercalate of claim 7 wherein the intercalant polymer is selected from the group consisting of polyvinylpyrrolidone, poly(vinyl alcohol), polyvinylimine, polyacrylic acid, poly(methacrylic acid), poly (methacrylamide), poly(N,N-dimethylacrylamide), poly(N-acetamideacrylamide), poly(N-acetomethamido-acrylamide), polyvinyloxazolidone, polyvinylmethyloxazolidone, poly-oxyethylene-polyoxypropylene block copolymers, polyethylenimine, and copolymers and mixtures thereof.

31. The intercalate of claim 30 wherein the intercalant polymer is polyvinyl alcohol.

32. The intercalate of claim 30 wherein the intercalant polymer is polyvinylpyrrolidone.

33. The intercalate of claim 30 wherein the intercalant polymer has a weight average molecular weight in the range of about 100 to about 100,000.

34. The intercalate of claim 1 wherein the concentration of intercalant pesticide in the intercalating composition is at least about 5% by weight, based on the dry weight of the layered material.

35. The intercalate of claim 34 wherein the concentration of intercalant pesticide in the intercalating composition is at least about 30% by weight, based on the dry weight of the layered material.

36. A pesticide composition comprising an organic liquid carrier in an amount of about to about 99.95% by weight of the composition, and about 0.05% to about 60% by weight of an intercalated phyllosilicate material, said intercalated phyllosilicate material formed by contacting a phyllosilicate, having adjacent phyllosilicate platelets, with a composition selected from the group consisting of water; a water-soluble intercalant polymer; a water-miscible organic solvent; and a mixture thereof, to form an intercalated phyllosilicate, and contacting the intercalated phyllosilicate with an intercalating composition, without prior sorption of an onium ion or silane coupling agent, comprising a pesticide and a pesticide carrier selected from the group consisting of water; a water-miscible organic solvent; and a mixture thereof, said intercalating composition having an intercalant pesticide concentration of at least 2% based on the weight of pesticide, water and organic solvent to achieve sorption of the intercalant pesticide between adjacent spaced layers of the phyllosilicate sufficient to expand the spacing between a predominance of the adjacent phyllosilicate platelets to at least about 10 Å, when measured after sorption of the intercalant pesticide and at a maximum water content of about 5% by weight, based on the dry weight of the phyllosilicate, said pesticide selected from the group consisting of the following, including salts thereof, esters thereof and mixtures thereof:

allyl alcohol, anilazine, triadimenol, benomyl, benquinox, bunema, captafol, captan, carbendazim, carboxin, chinosol, chloroneb, chlorothalonil, cycloheximide, dazomet, dicloran, dichlofluanid, dichlone, dimethirimol, dinocap, manzeb, dithianon, dodemorph, dodine, drazoxolon, edinfenphos, fenaminosulf, fenapanil, fentiazon, ferbam, folpet, fongarid, guazatine, hymexazol, iprodione, kasugamycin, maneb, 2-methoxyethylmercurychloride chloro(-2-methoxyethyl) mercury, methylthiophenate, metiram, nabam, neo-asozin, o-phenylphenol, phenylmercury acetate, oxycarboxin, parinol, quintozene, phosethyl, piperalin, polyoxin, procymidone, propineb, propazine, propionic acid, prothiocarb, pyracarbolid, pyrazophos, thiabendazole, thiophanate, thiram, tolylfluanid, triadimefon, tridemorph, triforine, triphenyltin acetate, validamycin A, vinclozolin, vondozeb, zineb, chloranil, ziram, 8-quinolinol, sulfallate, metam, glyodin, 2,6-bis [dimethylaminomethyl]cyclohexanone, hexachloroacetone, bromoacetyl bromide, picloram, benalaxyl, blasticidin S, bupirimate, buthiobate, chinomethionate, chlozolinate, cymoxanil, cyproconazole, dithianon, ethirimol, etridazole, fenarimol, fenpiclonil, fenpropidin, fenpropimorph, fentin, flusilazole, flutriafol, flutolanl, fuberidazole, furalaxyl, imazalil, imibenconazole, iprobenphos, isoprothiolane, mancozeb, mepronil, methfuroxam, metsulfovax, myclobutanil, nuarimol, ofurace, oxadixyl, polyoxin B, polyoxin D, prochloraz, procymidone, propiconazole, pyroquilon, quintozene, tebucanazole, tetraconazole, triarimol, tricyclazole, triforine, acifluorfen, alachlor, alanap, alloxydim, ametryn, amitrol, asulam, atrazine, azide, barban, benazolin, benefin, bensulide, bentazone, benthiocarb, benzoylprop, benzthiazuron, bifenox, acetochlor, acrolein, benazolin, buthidazole, allidochlor, bromacil, bromofenoxin, bromoxynil, butachlor, butralin, buturon, burylate, chlometoxynil, chloramben, chlorbromuron, chlorfenprop, chloridazon, chlorotoluron, chloroxuron, chlorpropham, chlorthiamid, 2,4,6-trichlorophenyl-4-nitrophenyl ether, crotoxyphos, cycloate, cyprazine, 2,4-dichlorophenoxyacetic acid, dalapon, 4-(2,4-dichlorophenoxy) butyric acid, dimethyl tetrachloroterephthalate, a mixture of tris (2,4-dichlorophenoxyethyl) phosphite, and bis (2,4-dichlorophenoxyethyl) phosphite, desmedipham, 2-(2, 4-dichlorophenoxy)propionic acid, desmetryn, diallate, dicamba, dichlobenil, dichlorprop, diethatyl, difenoxuron, diclofop, dimexano, dinitramine, dinoseb, dinoterb, diphenamid, dipropetryn, diquat, diuron, endothall, erbon, ethofumesate, fenac, fenuron, flamprop, fluchloralin, S-ethyl dipropylthiocarbamate, pentachlorophenol, fluometuron, fluorodifen, flurecol, glyphosate, glyphosine, hexazinone, ioxynil, isopropalin, isoproturon, karbutilate, lenacil, linuron, mecoprop, medinoterb, methazole, methoprotryne, metobromuron, metolachlor, metoxuron, metribuzin, molinate, monalide, monlinuron, monuron, naptalam, neburon, nitralin, nitrofen, norea, norflurazon, oryzalin, oxadiazon, paraquat, pebulate, penoxalin, perfluidone, phenisopham, phenmedipham, picloram, procyazine, profluralin, prometon, prometryn, pronamide, propachlor, propanil, propazine, propham, secbumeton, siduron, silvex, simazine, swep, 2,4,5-trichlorophenoxy acetic acid, 2,3,6-trichlorobenzoic acid, tebuthiuron, terbacil, terbumeton, terbuthylazine, terbutol, terbutryn, tetrafluoron, triallate, trietazine, trifluralin, vernolate, 1-naphthaleneacetic acid, N-m-tolylphthalamic acid, ethyl-1-naphthalene acetate, chloroacetic acid, trichloroacetic acid, p-chloromandelic acid, dimethylamino-2,3,5-triiodobenzoate, 2-naphthoxyacetic acid, phenoxyacetic acid, 2-phenoxypropionic acid, o-chlorophenoxy acetic acid, p-chlorophenoxy acetic acid, 4-chloro-2-methyl phenoxyacetic acid, silvex, 4-[(4-chloro-o-tolyl)oxy]butyric acid, p-bromophenoxy acetic acid, dimethylamino-4[2,4-dichlorophenoxy]butryate, 3-indolebutyric acid, 3-indoleacetic acid, 3-indolepropionic acid, gibberellic acid, N,N-dimethylsuccinamic acid, 2-furanacrylic acid, endothal, 1-naphthaleneacetamide, allidochlor, N-methyl-N-1-naphthylacetamide, N-1-naphthyl acetamide, 2-[3-chlorophenoxy]propionamide, noruron, siduron, metobromuron, terbacil, chloroxuron, aminotriazole, cyanazine, chlorflurenol, chlorsulfuron, cyanazine, cyometrinil, 3,6-dichloropicolinic acid, dichlofop, difenzoquat, diphenamid, ethaflualin, ethepon, flurazole, flurenol, fluridone, fosamine, isouron, mefluidide, 1,8-naphthalic anhydride, napropamide, pyrazon, thoibencarb, anilazine, diphenatrile, N-[2,4-dichlorophenoxy)acetyl-DL-methionine, daminozide, pyrazon, ethoxyquin, propham, S-carboxymethyl-N,N-dimethyldicarbamate, phosphan, merphos, ethephon, tricamba, amiben, glufosinate, indole-3-butyric acid, β-naphthoxyacetic acid, triclopyr, 9-undecylenic acid, oxyflurofen, dinitrocresol, flurtamone, diflufenican, difunon, fomesafen, clethodim, sethoxydim, haloxyfop, tralkoxydim, fenoxaprop, fluazifop, phaseolotoxin, rhizobitoxine, barban, ethephon, tetcyclacis, mepiquat chloride, ancymidol, uniconzaole, paclobutrazol, diquatop, pendimethalin, karbutilate, asulam, clopyralid, fluroxypyr, chlorimuron, chlorsulfuron, metsulfuron, buthidazole, imazamethabenz, imazapyr, imazaquin, imazethapry, isoxaben, cinmethylin, ethofumesate, acephate, aldicarb, aldoxycarb, aldrin, d-trans allethrin, allyxycarb, aminocarb, amitraz, azinphos, azinphos, azocyclotin, azothoate, bendiocarb, benzomate, binapacryl, bomyl, 2-sec-butylphenyl N-methylcarbamate, bromophos, bromophos-ethyl, bromopropylate, butacarb, butocarboxim, chlordane, chlordecone, heptachlor, lindane, methoxychlor, toxaphene, butoxicarboxim, carbaryl, carbofuran, carbophenothion, cartap, chloridimeform, chlorfenethol, chlorfenvinphos, chlormephos, chlorobenzilate, chloropropylate, chlorphoxim, chlorpyrifos, chlorthiophos, coumaphos, 2-chlorophenyl-N-methylcarbamate, crufomate, cryolite, cyanofenphos, cyanophos, cyhexatin, cypermethrin, cythioate, dichloro diphenyl trichloroethane, 2,2-dichlorovinyl o,o-dimethyl phosphate, demeton, demeton-S-methyl, dialifor, diazinon, dicofol, dicrotophos, dieldrin, dienochlor, diflubenzuron, dimefox, dimethoate, dimethrin, dinobuton, dioxacarb, dioxathion, disulfoton, 2-methyl-4,6-dinitrophenol, d-phenothrin, endosulfan, enfrin, o-ethyl o(4-nitrophenyl) phenylphosphonothioate, ethyl p-nitrophenyl thionobenzenephosphonate, ethiofencarb, ethion, ethoate, ethoprop, etrimfos, famphur, fenbutatin-oxide, fenitrothion, fenson, fensulfothion, fenthion, fenvalerate, fonofos, formetanate hydrochloride, formothion, fosthietan, hydroprene, isofenphos, isoxathion, isothioate, malathion, mecarbam, mecarphon, menazon, meobal, mephosfolan, mercaptodimethur, methamidophos, methidathion, methomyl, methoprene, isoprocarb, mirex, monocrotophos, m-tolyl-N-methylcarbamate, naled, nicotine, omethoate, oxamyl, oxydemeton-methyl, oxydisulfoton, parathion, permethrin, phenthoate, phorate, phosalone, phosmet, phosphamidon, phoxim, pirimicarb, pirimiphos, plifenate, profenofos, promecarb, propargite, propetamphos, propoxur, prothiophos, prothoate, quinalphos, resmethrin, ronnel, ryania, salithion, schradan, sulfotepp, sulprofos, temephos, tetraethyl diphosphate, terbufos, tetrachlorvinphos, tetradifon, tetramethrin, tetrasul, thiocyclamhydrogenoxalate, thiometon, thioquinox, triazophos, trichloronate, trichloron, vamidothion, melvinphos, trichlorofon, O,O-dimethyl phosphorochloriodothioate, methyl parathion, demeton O, dicapthon, O,O-diethylphosphorochloridothioate, propham, matacil, a mixture of m[1-ethylpropyl] phenylmethylcarbamate and m[1-ethylpropyl] phenylmethylcarbamate, pyrethrum, benzyl thiocyanate, rotenone, eugenol, aminozide, ancymidol, anthraquinone, brodifacoum, bromadiolone, butoxy polypropylene glycol, carbon tetrachloride, chloflurecolmethyl ester, chlormequat chloride, chlorophacinone, chloropicrin, chlorphonium, chlonitralid, coumachlor, coumafuryl, crimidine, cyoxmetril, deet, diazacosterol hydrochloride, dibutyl phthalate, ethyl hexanediol, dichlofenthion, difenacoum, dikegulac sodium, diphenylamine, ethephone, fenamiphos, fluoroacetamide, glyoxime, gossyplure, heliotropin acetal, kinoprene, maleic hydrazine, metaldehyde, metam-sodium, naphthalene acetamide, 1-naphthaleneacetic acid, nitrapyrin, pyriminal, scillirosid, sesamex, sulfoxide, trifenmorph, triprene, and warfarin.

37. The composition of claim 36 wherein the intercalated phyllosilicate is exfoliated into a predominance of single platelets having said intercalant pesticide complexed onto said platelet surfaces.

38. The composition of claim 36 wherein the pesticide carrier comprises a water-miscible organic solvent selected from the group consisting of alcohols, ketones, aldehydes, esters, glycols, glycerols, ethers, and mixtures thereof.

39. The composition of claim 36 wherein the organic liquid carrier is a monohydric alcohol having 1 to about 5 carbon atoms.

40. The composition of claim 36 wherein the organic liquid carrier is a polyhydric alcohol selected from the group consisting of glycols, glycerols, and mixtures thereof.

41. The composition of claim 36 wherein the intercalated phyllosilicate material is free of a compound having an onium ion or a silane coupling agent.

42. The composition of claim 36 having a viscosity of at least 5000 centipoise.

43. The composition of claim 36 wherein the composition is a thixotropic gel.

44. The composition of claim 4 wherein said layered material has a moisture content of about 4% to about 5000% by weight, based on the dry weight of said layered material and said water is capable of dissolving said intercalant polymer.

45. The composition of claim 4 wherein the moisture content of said layered material is about 30% to about 40% by weight based on the dry weight of said layered material.

46. The composition of claim 4 wherein the moisture content of said layered material is about 35% to about 40% by weight based on the dry weight of said layered material.

47. The composition of claim 4 wherein the moisture content of said layered material is about 5% to about 50% by weight water, based on the dry weight of said layered material.

48. The composition of claim 47 wherein the moisture content of said layered material is about 7% to about 100% by weight, based on the dry weight of said layered material.

* * * * *